(12) United States Patent
Van Meter et al.

(10) Patent No.: US 11,197,779 B2
(45) Date of Patent: Dec. 14, 2021

(54) OCULAR IMPLANT WITH PRESSURE SENSOR AND DELIVERY SYSTEM

(71) Applicant: IVANTIS, INC., Irvine, CA (US)

(72) Inventors: David Theodore Van Meter, Laguna Beach, CA (US); Kenneth M. Galt, Laguna Hills, CA (US)

(73) Assignee: IVANTIS, INC., Irvine, CA (US)

( * ) Notice: Subject to any disclaimer, the term of this patent is extended or adjusted under 35 U.S.C. 154(b) by 559 days.

(21) Appl. No.: 15/751,886

(22) PCT Filed: Aug. 12, 2016

(86) PCT No.: PCT/US2016/046652
§ 371 (c)(1),
(2) Date: Feb. 12, 2018

(87) PCT Pub. No.: WO2017/030917
PCT Pub. Date: Feb. 23, 2017

(65) Prior Publication Data
US 2019/0076296 A1    Mar. 14, 2019

Related U.S. Application Data

(60) Provisional application No. 62/205,588, filed on Aug. 14, 2015.

(51) Int. Cl.
*A61F 9/007* (2006.01)
*A61B 3/16* (2006.01)
*A61F 9/00* (2006.01)

(52) U.S. Cl.
CPC ............ *A61F 9/00781* (2013.01); *A61B 3/16* (2013.01); *A61F 9/0017* (2013.01); *A61F 2250/0002* (2013.01); *A61F 2250/0013* (2013.01)

(58) Field of Classification Search
CPC ................ A61F 9/00781; A61F 9/0017; A61F 2250/0002; A61F 2250/0013; A61B 3/16
See application file for complete search history.

(56) References Cited

U.S. PATENT DOCUMENTS 703,296 A    6/1902   Arnold
1,601,709 A  10/1926  Windom
(Continued)

FOREIGN PATENT DOCUMENTS

AU    1998/76197 B2    2/1999
DE        4226476 C1    8/1993
(Continued)

OTHER PUBLICATIONS

Wardle et al.; U.S. Appl. No. 16/668,458 entitled "Single operator device for delivering an ocular implant," filed Oct. 30, 2019.
(Continued)

*Primary Examiner* — Tatyana Zalukaeva
*Assistant Examiner* — Heather K Barnwell
(74) *Attorney, Agent, or Firm* — Shay Glenn LLP

(57) ABSTRACT

An ocular implant including an intraocular pressure sensor and having an inlet portion and a Schlemm's canal portion distal to the inlet portion, the inlet portion being disposed at a proximal end of the implant and sized and configured to be placed within an anterior chamber of a human eye, the Schlemm's canal portion being arranged and configured to be disposed within Schlemm's canal of the eye when the inlet portion is disposed in the anterior chamber.

7 Claims, 33 Drawing Sheets

(56) References Cited

U.S. PATENT DOCUMENTS

| | | |
|---|---|---|
| 2,716,983 A | 9/1955 | George et al. |
| 3,071,135 A | 1/1963 | Baldwin et al. |
| 3,788,327 A | 1/1974 | Donowitz et al. |
| 3,811,442 A | 5/1974 | Maroth |
| 3,858,577 A | 1/1975 | Bass et al. |
| 3,884,236 A | 5/1975 | Krasnov |
| 3,948,271 A | 4/1976 | Akiyama |
| 3,958,558 A | 5/1976 | Dunphy et al. |
| 3,982,541 A | 9/1976 | L'Esperance |
| 4,037,604 A | 7/1977 | Newkirk |
| 4,127,110 A | 11/1978 | Bullara |
| 4,134,405 A | 1/1979 | Smit |
| 4,273,109 A | 6/1981 | Enderby |
| 4,391,275 A | 7/1983 | Fankhauser et al. |
| 4,428,746 A | 1/1984 | Mendez |
| 4,457,757 A | 7/1984 | Molteno |
| 4,461,294 A | 7/1984 | Baron |
| 4,470,407 A | 9/1984 | Hussein |
| 4,497,319 A | 2/1985 | Sekine et al. |
| 4,501,274 A | 2/1985 | Skjaerpe |
| 4,517,973 A | 5/1985 | Sunago et al. |
| 4,538,608 A | 9/1985 | L'Esperance |
| 4,548,205 A | 10/1985 | Armeniades et al. |
| 4,551,129 A | 11/1985 | Coleman et al. |
| 4,558,698 A | 12/1985 | O'Dell |
| 4,559,942 A | 12/1985 | Eisenberg |
| 4,566,438 A | 1/1986 | Liese et al. |
| 4,580,559 A | 4/1986 | L'Esperance |
| 4,583,539 A | 4/1986 | Karlin et al. |
| 4,601,713 A | 7/1986 | Fuquo |
| 4,604,087 A | 8/1986 | Joseph |
| 4,633,866 A | 1/1987 | Peyman et al. |
| 4,658,816 A | 4/1987 | Ector |
| 4,660,546 A | 4/1987 | Herrick et al. |
| 4,671,273 A | 6/1987 | Lindsey |
| 4,689,040 A | 8/1987 | Thompson |
| 4,699,140 A | 10/1987 | Holmes et al. |
| 4,706,669 A | 11/1987 | Schlegel |
| 4,722,350 A | 2/1988 | Armeniades et al. |
| 4,722,724 A | 2/1988 | Schocket |
| 4,729,373 A | 3/1988 | Peyman |
| 4,733,665 A | 3/1988 | Palmaz |
| 4,750,901 A | 6/1988 | Molteno |
| 4,770,654 A | 9/1988 | Rogers et al. |
| 4,791,927 A | 12/1988 | Menger |
| 4,826,478 A | 5/1989 | Schocket |
| 4,846,172 A | 7/1989 | Berlin |
| 4,861,341 A | 8/1989 | Woodburn |
| 4,876,250 A | 10/1989 | Clark |
| 4,880,000 A | 11/1989 | Holmes et al. |
| 4,886,488 A | 12/1989 | White |
| 4,919,130 A | 4/1990 | Stoy et al. |
| 4,925,299 A | 5/1990 | Meisberger et al. |
| 4,934,363 A | 6/1990 | Smith et al. |
| 4,934,809 A | 6/1990 | Volk |
| 4,936,825 A | 6/1990 | Ungerleider |
| 4,946,436 A | 8/1990 | Smith |
| 4,968,296 A | 11/1990 | Ritch et al. |
| 4,994,060 A | 2/1991 | Rink et al. |
| 5,034,010 A | 7/1991 | Kittrell et al. |
| 5,092,837 A | 3/1992 | Ritch et al. |
| 5,123,902 A | 6/1992 | Muller et al. |
| 5,127,901 A | 7/1992 | Odrich |
| 5,129,895 A | 7/1992 | Vassiliadis et al. |
| 5,178,604 A | 1/1993 | Baerveldt et al. |
| 5,180,362 A | 1/1993 | Worst |
| 5,190,552 A | 3/1993 | Kelman |
| 5,213,569 A | 5/1993 | Davis |
| 5,238,004 A | 8/1993 | Sahatjian et al. |
| 5,246,452 A | 9/1993 | Sinnott |
| 5,254,112 A | 10/1993 | Sinofsky et al. |
| 5,273,056 A | 12/1993 | McLaughlin et al. |
| 5,290,267 A | 3/1994 | Zimmermann |
| 5,300,020 A | 4/1994 | L'Esperance |
| 5,359,685 A | 10/1994 | Waynant et al. |
| 5,360,399 A | 11/1994 | Stegmann |
| 5,371,078 A | 12/1994 | Clark et al. |
| 5,372,577 A | 12/1994 | Ungerleider |
| 5,443,893 A | 8/1995 | Herzberg |
| 5,445,637 A | 8/1995 | Bretton |
| 5,454,796 A | 10/1995 | Krupin |
| 5,458,615 A | 10/1995 | Klemm et al. |
| 5,501,274 A | 3/1996 | Nguyen et al. |
| 5,536,259 A | 7/1996 | Utterberg |
| 5,575,780 A | 11/1996 | Saito |
| 5,579,235 A | 11/1996 | Schlichenmaier et al. |
| 5,591,223 A | 1/1997 | Lock et al. |
| 5,607,966 A | 3/1997 | Hellberg et al. |
| 5,613,972 A | 3/1997 | Lee et al. |
| 5,626,558 A | 5/1997 | Suson |
| 5,643,250 A | 7/1997 | O'Donnell |
| 5,653,753 A | 8/1997 | Brady et al. |
| 5,657,760 A | 8/1997 | Ying et al. |
| 5,676,669 A | 10/1997 | Colvard |
| 5,704,907 A | 1/1998 | Nordquist et al. |
| 5,713,844 A | 2/1998 | Peyman |
| 5,722,970 A | 3/1998 | Colvard et al. |
| 5,736,491 A | 4/1998 | Patel et al. |
| 5,738,676 A | 4/1998 | Hammer et al. |
| 5,738,677 A | 4/1998 | Colvard et al. |
| 5,785,658 A | 7/1998 | Benaron et al. |
| 5,792,099 A | 8/1998 | DeCamp et al. |
| 5,792,103 A | 8/1998 | Schwartz et al. |
| 5,807,302 A | 9/1998 | Wandel |
| 5,811,453 A | 9/1998 | Yanni et al. |
| 5,865,831 A | 2/1999 | Cozean et al. |
| 5,868,697 A | 2/1999 | Richter et al. |
| 5,873,835 A | 2/1999 | Hastings et al. |
| 5,879,319 A | 3/1999 | Pynson et al. |
| 5,885,279 A | 3/1999 | Bretton |
| 5,890,300 A | 4/1999 | Brenner et al. |
| 5,893,837 A | 4/1999 | Eagles et al. |
| 5,895,831 A | 4/1999 | Brasier et al. |
| 5,919,171 A | 7/1999 | Kira et al. |
| 5,939,299 A | 8/1999 | Wong et al. |
| 5,948,427 A | 9/1999 | Yamamoto et al. |
| 5,968,058 A | 10/1999 | Richter et al. |
| 5,990,099 A | 11/1999 | Clark |
| 5,993,438 A | 11/1999 | Juhasz et al. |
| 5,997,531 A | 12/1999 | Loeb et al. |
| 6,002,480 A | 12/1999 | Izatt et al. |
| 6,007,511 A | 12/1999 | Prywes |
| 6,050,970 A | 4/2000 | Baerveldt |
| 6,083,193 A | 7/2000 | Kadziauskas et al. |
| 6,099,521 A | 8/2000 | Shadduck |
| 6,102,045 A | 8/2000 | Nordquist et al. |
| 6,146,375 A | 11/2000 | Juhasz et al. |
| 6,177,544 B1 | 1/2001 | Kanai et al. |
| 6,186,974 B1 | 2/2001 | Allan et al. |
| 6,217,584 B1 | 4/2001 | Nun |
| 6,221,078 B1 | 4/2001 | Bylsma |
| 6,238,409 B1 | 5/2001 | Hojeibane |
| 6,241,721 B1 | 6/2001 | Cozean et al. |
| D444,874 S | 7/2001 | Haffner et al. |
| 6,297,228 B1 | 10/2001 | Clark |
| 6,319,274 B1 | 11/2001 | Shadduck |
| 6,328,747 B1 | 12/2001 | Nun |
| 6,375,642 B1 | 4/2002 | Grieshaber et al. |
| 6,398,809 B1 | 6/2002 | Hoffmann et al. |
| 6,409,752 B1 | 6/2002 | Boatman et al. |
| 6,450,984 B1 | 9/2002 | Lynch et al. |
| 6,464,724 B1 | 10/2002 | Lynch et al. |
| 6,471,666 B1 | 10/2002 | Odrich |
| 6,494,857 B1 | 12/2002 | Neuhann |
| 6,508,779 B1 | 1/2003 | Suson |
| 6,508,803 B1 | 1/2003 | Horikawa et al. |
| 6,517,523 B1 | 2/2003 | Kaneko et al. |
| 6,524,275 B1 | 2/2003 | Lynch et al. |
| 6,533,764 B1 | 3/2003 | Haffner et al. |
| 6,533,768 B1 | 3/2003 | Hill |
| 6,544,208 B2 | 4/2003 | Ethier et al. |
| 6,544,249 B1 | 4/2003 | Yu et al. |
| 6,551,289 B1 | 4/2003 | Higuchi et al. |
| 6,579,235 B1 | 6/2003 | Abita et al. |

(56) References Cited

U.S. PATENT DOCUMENTS

| | | |
|---|---|---|
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,210 B2 | 3/2004 | Williams et al. |
| 6,699,211 B2 | 3/2004 | Savage |
| 6,702,790 B1 | 3/2004 | Ross |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,198 B2 | 4/2005 | Brown |
| 6,890,300 B2 | 5/2005 | Lloyd et al. |
| 6,899,717 B2 | 5/2005 | Weber et al. |
| 6,939,298 B2 | 9/2005 | Brown et al. |
| 6,955,656 B2 | 10/2005 | Bergheim et al. |
| 6,962,573 B1 | 11/2005 | Wilcox |
| 6,981,958 B1 | 1/2006 | Gharib et al. |
| 6,989,007 B2 | 1/2006 | Shadduck |
| 7,018,376 B2 | 3/2006 | Webb et al. |
| 7,094,225 B2 | 8/2006 | Tu et al. |
| 7,125,119 B2 | 10/2006 | Farberov |
| 7,131,945 B2 | 11/2006 | Fink et al. |
| 7,133,137 B2 | 11/2006 | Shimmick |
| 7,135,009 B2 | 11/2006 | Tu et al. |
| 7,147,650 B2 | 12/2006 | Lee |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,207,980 B2 | 4/2007 | Christian et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,488,303 B1 | 2/2009 | Haffner et al. |
| 7,699,882 B2 | 4/2010 | Stamper et al. |
| 7,740,604 B2 | 6/2010 | Schieber et al. |
| 7,931,596 B2 | 4/2011 | Rachlin et al. |
| 7,967,772 B2 | 6/2011 | McKenzie et al. |
| 8,012,115 B2 | 9/2011 | Karageozian |
| 8,123,729 B2 | 2/2012 | Yamamoto et al. |
| 8,142,364 B2 | 3/2012 | Haffner et al. |
| 8,172,899 B2 | 5/2012 | Silvestrini et al. |
| 8,182,435 B2 | 5/2012 | Dacquay et al. |
| 8,257,295 B2 | 9/2012 | Rickard et al. |
| 8,267,882 B2 | 9/2012 | Euteneuer et al. |
| 8,282,592 B2 | 10/2012 | Schieber et al. |
| 8,308,701 B2 | 11/2012 | Horvath et al. |
| 8,337,509 B2 | 12/2012 | Schieber et al. |
| 8,372,026 B2 | 2/2013 | Schieber et al. |
| 8,414,518 B2 | 4/2013 | Schieber et al. |
| 8,425,449 B2 | 4/2013 | Wardle et al. |
| 8,475,374 B2 | 7/2013 | Irazoqui et al. |
| 8,512,404 B2 | 8/2013 | Frion et al. |
| 8,529,494 B2 | 9/2013 | Euteneuer et al. |
| 8,540,659 B2 | 9/2013 | Berlin |
| 8,551,166 B2 | 10/2013 | Schieber et al. |
| 8,585,664 B2 | 11/2013 | Dos Santos et al. |
| 8,629,161 B2 | 1/2014 | Mizuno et al. |
| 8,636,647 B2 | 1/2014 | Silvestrini et al. |
| 8,647,659 B2 | 2/2014 | Robinson et al. |
| 8,657,776 B2 | 2/2014 | Wardle et al. |
| 8,663,150 B2 | 3/2014 | Wardle et al. |
| 8,663,303 B2 | 3/2014 | Horvath et al. |
| 8,734,377 B2 | 5/2014 | Schieber et al. |
| 8,808,222 B2 | 8/2014 | Schieber et al. |
| 8,808,224 B2 | 8/2014 | Rickard |
| 8,939,906 B2 | 1/2015 | Huang et al. |
| 8,939,948 B2 | 1/2015 | De Juan, Jr. et al. |
| 8,945,038 B2 | 2/2015 | Yablonski |
| 8,951,221 B2 | 2/2015 | Stegmann et al. |
| 8,961,447 B2 | 2/2015 | Schieber et al. |
| 8,974,511 B2 | 3/2015 | Horvath et al. |
| 8,998,838 B2 | 4/2015 | Yalamanchili |
| 9,039,650 B2 | 5/2015 | Schieber et al. |
| 9,050,169 B2 | 6/2015 | Schieber et al. |
| 9,066,750 B2 | 6/2015 | Wardle et al. |
| 9,066,783 B2 | 6/2015 | Euteneuer et al. |
| 9,155,655 B2 | 10/2015 | Wardle et al. |
| 9,211,213 B2 | 12/2015 | Wardle et al. |
| 9,226,852 B2 | 1/2016 | Schieber et al. |
| 9,301,875 B2 | 4/2016 | Tu et al. |
| 9,351,874 B2 | 5/2016 | Schieber et al. |
| 9,358,156 B2 | 6/2016 | Wardle et al. |
| 9,402,767 B2 | 8/2016 | Schieber et al. |
| 9,510,973 B2 | 12/2016 | Wardle |
| 9,579,234 B2 | 2/2017 | Wardle et al. |
| 9,610,196 B2 | 4/2017 | Schieber et al. |
| 9,636,254 B2 | 5/2017 | Yu et al. |
| 9,642,746 B2 | 5/2017 | Berlin |
| 9,693,899 B2 | 7/2017 | Wardle et al. |
| 9,693,901 B2 | 7/2017 | Horvath et al. |
| 9,693,902 B2 | 7/2017 | Euteneuer et al. |
| 9,730,638 B2 | 8/2017 | Haffner et al. |
| 9,757,276 B2 | 9/2017 | Penhasi |
| 9,775,729 B2 | 10/2017 | McClain et al. |
| 9,782,293 B2 | 10/2017 | Doci |
| 9,788,999 B2 | 10/2017 | Schaller |
| 9,795,503 B2 | 10/2017 | Perez Grossmann |
| 9,808,373 B2 | 11/2017 | Horvath et al. |
| 9,820,883 B2 | 11/2017 | Berlin |
| 9,833,357 B2 | 12/2017 | Berlin |
| 9,931,243 B2 | 4/2018 | Wardle et al. |
| 10,159,601 B2 | 12/2018 | Berlin |
| 10,390,993 B1 | 8/2019 | Berlin |
| 2001/0002438 A1 | 5/2001 | Sepetka et al. |
| 2002/0003546 A1 | 1/2002 | Mochimaru et al. |
| 2002/0013546 A1 | 1/2002 | Grieshaber et al. |
| 2002/0013572 A1* | 1/2002 | Berlin ............... A61F 9/00802 606/4 |
| 2002/0052653 A1 | 5/2002 | Durgin |
| 2002/0072673 A1 | 6/2002 | Yamamoto et al. |
| 2002/0082591 A1 | 6/2002 | Haefliger |
| 2002/0133168 A1 | 9/2002 | Smedley et al. |
| 2002/0143284 A1 | 10/2002 | Tu et al. |
| 2002/0165504 A1 | 11/2002 | Sharp et al. |
| 2002/0165522 A1 | 11/2002 | Holmen |
| 2002/0193805 A1 | 12/2002 | Ott et al. |
| 2003/0004457 A1 | 1/2003 | Andersson |
| 2003/0014092 A1 | 1/2003 | Neuhann |
| 2003/0040754 A1 | 2/2003 | Mitchell et al. |
| 2003/0055372 A1 | 3/2003 | Lynch et al. |
| 2003/0060748 A1 | 3/2003 | Baikoff |
| 2003/0060752 A1 | 3/2003 | Bergheim et al. |
| 2003/0060784 A1 | 3/2003 | Hilgers et al. |
| 2003/0093084 A1 | 5/2003 | Nissan et al. |
| 2003/0097151 A1 | 5/2003 | Smedley et al. |
| 2003/0105456 A1 | 6/2003 | Lin |
| 2003/0125351 A1 | 7/2003 | Azuma et al. |
| 2003/0175324 A1 | 9/2003 | Robinson et al. |
| 2003/0181848 A1 | 9/2003 | Bergheim et al. |
| 2003/0187384 A1 | 10/2003 | Bergheim et al. |
| 2003/0212387 A1 | 11/2003 | Kurtz et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0024453 A1 | 2/2004 | Castillejos |
| 2004/0030302 A1 | 2/2004 | Kamata et al. |
| 2004/0070761 A1 | 4/2004 | Horvath et al. |
| 2004/0073137 A1 | 4/2004 | Lloyd et al. |
| 2004/0082939 A1 | 4/2004 | Berlin |
| 2004/0088048 A1 | 5/2004 | Richter et al. |
| 2004/0092856 A1 | 5/2004 | Dahan |
| 2004/0098124 A1 | 5/2004 | Freeman et al. |
| 2004/0102729 A1 | 5/2004 | Haffner et al. |
| 2004/0106975 A1 | 6/2004 | Solovay et al. |
| 2004/0111050 A1 | 6/2004 | Smedley et al. |
| 2004/0116909 A1 | 6/2004 | Neuberger et al. |
| 2004/0122380 A1 | 6/2004 | Utterberg |

(56) References Cited

U.S. PATENT DOCUMENTS

| | | |
|---|---|---|
| 2004/0127843 A1 | 7/2004 | Tu et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0199149 A1 | 10/2004 | Myers et al. |
| 2004/0199171 A1 | 10/2004 | Akahoshi |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225357 A1 | 11/2004 | Worst et al. |
| 2004/0228013 A1 | 11/2004 | Goldstein et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0041200 A1 | 2/2005 | Rich |
| 2005/0043722 A1 | 2/2005 | Lin |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1* | 6/2005 | Haffner .............. A61B 3/16 604/500 |
| 2005/0125003 A1 | 6/2005 | Pinchuk et al. |
| 2005/0131514 A1 | 6/2005 | Hijlkema et al. |
| 2005/0149114 A1 | 7/2005 | Cartledge et al. |
| 2005/0154443 A1 | 7/2005 | Linder et al. |
| 2005/0165385 A1 | 7/2005 | Simon |
| 2005/0192527 A1 | 9/2005 | Gharib et al. |
| 2005/0197667 A1 | 9/2005 | Chan et al. |
| 2005/0203542 A1 | 9/2005 | Weber et al. |
| 2005/0209549 A1 | 9/2005 | Bergheim et al. |
| 2005/0209550 A1 | 9/2005 | Bergheim et al. |
| 2005/0240168 A1 | 10/2005 | Neuberger et al. |
| 2005/0244464 A1 | 11/2005 | Hughes |
| 2005/0245916 A1 | 11/2005 | Connor |
| 2005/0250788 A1 | 11/2005 | Tu et al. |
| 2005/0260186 A1 | 11/2005 | Bookbinder et al. |
| 2005/0266047 A1 | 12/2005 | Tu et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0279369 A1 | 12/2005 | Lin |
| 2005/0288619 A1 | 12/2005 | Gharib et al. |
| 2005/0288745 A1 | 12/2005 | Andersen et al. |
| 2006/0020247 A1 | 1/2006 | Kagan et al. |
| 2006/0021623 A1 | 2/2006 | Miller et al. |
| 2006/0032507 A1 | 2/2006 | Tu |
| 2006/0052879 A1 | 3/2006 | Kolb |
| 2006/0069340 A1 | 3/2006 | Simon |
| 2006/0074375 A1 | 4/2006 | Bergheim et al. |
| 2006/0079828 A1 | 4/2006 | Brown |
| 2006/0084907 A1 | 4/2006 | Bergheim et al. |
| 2006/0084954 A1 | 4/2006 | Zadoyan et al. |
| 2006/0106370 A1 | 5/2006 | Baerveldt et al. |
| 2006/0110428 A1 | 5/2006 | deJuan et al. |
| 2006/0116626 A1 | 6/2006 | Smedley et al. |
| 2006/0117859 A1 | 6/2006 | Liu et al. |
| 2006/0129141 A1 | 6/2006 | Lin |
| 2006/0149194 A1 | 7/2006 | Conston et al. |
| 2006/0154382 A1 | 7/2006 | Basceri et al. |
| 2006/0154981 A1 | 7/2006 | Klimko et al. |
| 2006/0155238 A1 | 7/2006 | Shields |
| 2006/0155265 A1 | 7/2006 | Juhasz et al. |
| 2006/0155300 A1 | 7/2006 | Stamper et al. |
| 2006/0167421 A1 | 7/2006 | Quinn |
| 2006/0167466 A1 | 7/2006 | Dusek |
| 2006/0173397 A1 | 8/2006 | Tu et al. |
| 2006/0173399 A1* | 8/2006 | Rodgers .............. A61F 9/00781 604/9 |
| 2006/0178674 A1 | 8/2006 | McIntyre |
| 2006/0189915 A1 | 8/2006 | Camras et al. |
| 2006/0189916 A1 | 8/2006 | Bas et al. |
| 2006/0189917 A1 | 8/2006 | Mayr et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |
| 2006/0200113 A1 | 9/2006 | Haffner et al. |
| 2006/0224146 A1 | 10/2006 | Lin |
| 2006/0241749 A1 | 10/2006 | Tu et al. |
| 2006/0259021 A1 | 11/2006 | Lin |
| 2006/0264971 A1 | 11/2006 | Akahoshi |
| 2006/0276759 A1 | 12/2006 | Kinast et al. |
| 2007/0010827 A1 | 1/2007 | Tu et al. |
| 2007/0021725 A1 | 1/2007 | Villette |
| 2007/0027452 A1 | 2/2007 | Varner et al. |
| 2007/0073275 A1 | 3/2007 | Conston et al. |
| 2007/0088432 A1 | 4/2007 | Solovay et al. |
| 2007/0093794 A1 | 4/2007 | Wang et al. |
| 2007/0093796 A1 | 4/2007 | Raksi et al. |
| 2007/0106200 A1 | 5/2007 | Levy |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0121120 A1 | 5/2007 | Schachar |
| 2007/0123767 A1 | 5/2007 | Montegrande et al. |
| 2007/0135681 A1 | 6/2007 | Chin et al. |
| 2007/0156079 A1* | 7/2007 | Brown .............. A61B 3/16 604/9 |
| 2007/0173791 A1 | 7/2007 | Raksi |
| 2007/0179520 A1 | 8/2007 | West |
| 2007/0191863 A1 | 8/2007 | De Juan, Jr. et al. |
| 2007/0202186 A1 | 8/2007 | Yamamoto et al. |
| 2007/0208325 A1 | 9/2007 | Kurtz |
| 2007/0219509 A1 | 9/2007 | Tashiro et al. |
| 2007/0219541 A1 | 9/2007 | Kurtz |
| 2007/0235543 A1 | 10/2007 | Zadoyan et al. |
| 2007/0236771 A1 | 10/2007 | Zadoyan et al. |
| 2007/0265582 A1 | 11/2007 | Kaplan et al. |
| 2007/0270945 A1 | 11/2007 | Kobayashi et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2007/0293872 A1 | 12/2007 | Peyman |
| 2007/0298068 A1 | 12/2007 | Badawi et al. |
| 2008/0015488 A1 | 1/2008 | Tu et al. |
| 2008/0027519 A1 | 1/2008 | Guerrero |
| 2008/0045878 A1 | 2/2008 | Bergheim et al. |
| 2008/0058704 A1 | 3/2008 | Hee et al. |
| 2008/0058777 A1 | 3/2008 | Kurtz et al. |
| 2008/0082088 A1 | 4/2008 | Kurtz et al. |
| 2008/0091224 A1 | 4/2008 | Griffis et al. |
| 2008/0119827 A1 | 5/2008 | Kurtz et al. |
| 2008/0139959 A1 | 6/2008 | Miethke et al. |
| 2008/0215117 A1 | 9/2008 | Gross |
| 2008/0228127 A1 | 9/2008 | Burns et al. |
| 2008/0278687 A1 | 11/2008 | Somani |
| 2008/0288082 A1 | 11/2008 | Deal |
| 2008/0312661 A1 | 12/2008 | Downer et al. |
| 2009/0005852 A1 | 1/2009 | Gittings et al. |
| 2009/0028953 A1 | 1/2009 | Yamamoto et al. |
| 2009/0030363 A1 | 1/2009 | Gellman |
| 2009/0030381 A1 | 1/2009 | Lind et al. |
| 2009/0036843 A1 | 2/2009 | Erskine |
| 2009/0043321 A1 | 2/2009 | Conston et al. |
| 2009/0054723 A1 | 2/2009 | Khairkhahan et al. |
| 2009/0069786 A1 | 3/2009 | Vesely et al. |
| 2009/0082862 A1 | 3/2009 | Schieber et al. |
| 2009/0104248 A1 | 4/2009 | Rapacki et al. |
| 2009/0118716 A1 | 5/2009 | Brownell |
| 2009/0118717 A1 | 5/2009 | Brownell et al. |
| 2009/0118718 A1 | 5/2009 | Raksi et al. |
| 2009/0131921 A1 | 5/2009 | Kurtz et al. |
| 2009/0137988 A1 | 5/2009 | Kurtz |
| 2009/0138081 A1 | 5/2009 | Bergheim et al. |
| 2009/0157062 A1 | 6/2009 | Hauger et al. |
| 2009/0171327 A1 | 7/2009 | Kurtz et al. |
| 2009/0182421 A1 | 7/2009 | Silvestrini et al. |
| 2009/0198248 A1 | 8/2009 | Yeung et al. |

(56) References Cited

U.S. PATENT DOCUMENTS

| | | |
|---|---|---|
| 2009/0204053 A1 | 8/2009 | Nissan et al. |
| 2009/0247955 A1 | 10/2009 | Yamamoto et al. |
| 2009/0259126 A1 | 10/2009 | Saal et al. |
| 2009/0281520 A1 | 11/2009 | Highley et al. |
| 2009/0281530 A1 | 11/2009 | Korn |
| 2009/0291423 A1 | 11/2009 | Hara |
| 2009/0299216 A1 | 12/2009 | Chen et al. |
| 2010/0004580 A1 | 1/2010 | Lynch et al. |
| 2010/0036488 A1 | 2/2010 | de Juan et al. |
| 2010/0057072 A1 | 3/2010 | Roman et al. |
| 2010/0114309 A1 | 5/2010 | de Juan et al. |
| 2010/0137981 A1 | 6/2010 | Silvestrini et al. |
| 2010/0173866 A1 | 7/2010 | Hee et al. |
| 2010/0191176 A1 | 7/2010 | Ho et al. |
| 2010/0191177 A1 | 7/2010 | Chang et al. |
| 2010/0234717 A1 | 9/2010 | Wismer |
| 2010/0234726 A1 | 9/2010 | Sirimanne et al. |
| 2010/0234790 A1 | 9/2010 | Tu et al. |
| 2010/0262174 A1 | 10/2010 | Sretavan et al. |
| 2010/0324543 A1 | 12/2010 | Kurtz et al. |
| 2010/0331858 A1 | 12/2010 | Simaan et al. |
| 2011/0028948 A1 | 2/2011 | Raksi et al. |
| 2011/0028949 A1 | 2/2011 | Raksi et al. |
| 2011/0028950 A1 | 2/2011 | Raksi et al. |
| 2011/0028951 A1 | 2/2011 | Raksi et al. |
| 2011/0028952 A1 | 2/2011 | Raksi et al. |
| 2011/0028953 A1 | 2/2011 | Raksi et al. |
| 2011/0028954 A1 | 2/2011 | Raksi et al. |
| 2011/0028955 A1 | 2/2011 | Raksi |
| 2011/0028957 A1 | 2/2011 | Raksi et al. |
| 2011/0028958 A1 | 2/2011 | Raksi et al. |
| 2011/0098809 A1 | 4/2011 | Wardle et al. |
| 2011/0196487 A1 | 8/2011 | Badawi et al. |
| 2011/0218523 A1 | 9/2011 | Robl |
| 2011/0224597 A1 | 9/2011 | Stegmann et al. |
| 2012/0010702 A1 | 1/2012 | Stegmann et al. |
| 2012/0021397 A1 | 1/2012 | Van Dalen et al. |
| 2012/0022424 A1 | 1/2012 | Yamamoto et al. |
| 2012/0035524 A1 | 2/2012 | Silvestrini |
| 2012/0059461 A1* | 3/2012 | Badawi ............... A61F 2/14 623/4.1 |
| 2012/0136439 A1* | 5/2012 | Schieber ............ A61F 9/00781 623/6.64 |
| 2012/0184892 A1 | 7/2012 | Bigler et al. |
| 2012/0191064 A1 | 7/2012 | Conston et al. |
| 2012/0226132 A1 | 9/2012 | Wong et al. |
| 2012/0226133 A1* | 9/2012 | Wong ................. A61B 5/6846 600/398 |
| 2012/0238857 A1 | 9/2012 | Wong et al. |
| 2012/0259195 A1 | 10/2012 | Haffner et al. |
| 2012/0271272 A1 | 10/2012 | Hammack et al. |
| 2012/0283557 A1 | 11/2012 | Berlin |
| 2012/0302861 A1* | 11/2012 | Marshall ............... A61B 3/16 600/398 |
| 2013/0023837 A1 | 1/2013 | Becker |
| 2013/0041245 A1 | 2/2013 | Cerboni |
| 2013/0090534 A1 | 4/2013 | Burns et al. |
| 2013/0144202 A1 | 6/2013 | Field et al. |
| 2013/0158381 A1 | 6/2013 | Rickard |
| 2013/0182223 A1 | 7/2013 | Wardle et al. |
| 2013/0184631 A1 | 7/2013 | Pinchuk |
| 2013/0253402 A1 | 9/2013 | Badawi et al. |
| 2013/0253403 A1 | 9/2013 | Badawi et al. |
| 2013/0253437 A1 | 9/2013 | Badawi et al. |
| 2013/0253438 A1 | 9/2013 | Badawi et al. |
| 2013/0253528 A1 | 9/2013 | Haffner et al. |
| 2013/0267887 A1 | 10/2013 | Kahook et al. |
| 2013/0281908 A1 | 10/2013 | Schaller et al. |
| 2014/0016097 A1 | 1/2014 | Leonardi et al. |
| 2014/0018720 A1 | 1/2014 | Horvath et al. |
| 2014/0066821 A1 | 3/2014 | Freidland et al. |
| 2014/0066831 A1 | 3/2014 | Silvestrini et al. |
| 2014/0081195 A1 | 3/2014 | Clauson et al. |
| 2014/0243645 A1 | 8/2014 | Leonardi |
| 2014/0324128 A1 | 10/2014 | Gross |
| 2014/0371624 A1 | 12/2014 | Ziaie et al. |
| 2015/0018746 A1 | 1/2015 | Hattenbach |
| 2015/0022780 A1 | 1/2015 | John et al. |
| 2015/0038893 A1 | 2/2015 | Haffner et al. |
| 2015/0045714 A1 | 2/2015 | Horvath et al. |
| 2015/0057583 A1 | 2/2015 | Gunn et al. |
| 2015/0057591 A1 | 2/2015 | Horvath et al. |
| 2015/0057595 A1 | 2/2015 | Gunn et al. |
| 2015/0057596 A1 | 2/2015 | Lind et al. |
| 2015/0065940 A1 | 3/2015 | Rangel-Friedman et al. |
| 2015/0080783 A1 | 3/2015 | Berlin |
| 2015/0148836 A1 | 5/2015 | Heeren |
| 2015/0282982 A1 | 10/2015 | Schieber et al. |
| 2015/0290033 A1 | 10/2015 | Wardle et al. |
| 2015/0305939 A1 | 10/2015 | Vera et al. |
| 2015/0305940 A1 | 10/2015 | Vera et al. |
| 2015/0313759 A1 | 11/2015 | Vera et al. |
| 2015/0366710 A1 | 12/2015 | Schieber et al. |
| 2016/0015265 A1 | 1/2016 | Mandel et al. |
| 2016/0051406 A1 | 2/2016 | Wardle et al. |
| 2016/0063898 A1 | 3/2016 | Bernal |
| 2016/0250072 A1 | 9/2016 | Wardle et al. |
| 2016/0310020 A1 | 10/2016 | Warnking et al. |
| 2017/0127941 A1 | 5/2017 | Ostermeier et al. |
| 2017/0143541 A1 | 5/2017 | Badawi et al. |
| 2017/0156848 A1 | 6/2017 | Schieber |
| 2017/0164831 A1 | 6/2017 | Choo et al. |
| 2017/0172794 A1 | 6/2017 | Varner et al. |
| 2017/0172795 A1 | 6/2017 | Lerner |
| 2017/0172797 A1 | 6/2017 | Horvath et al. |
| 2017/0172798 A1 | 6/2017 | Horvath et al. |
| 2017/0172799 A1 | 6/2017 | Horvath |
| 2017/0172800 A1 | 6/2017 | Romoda et al. |
| 2017/0202708 A1 | 7/2017 | Berlin |
| 2017/0239272 A1 | 8/2017 | Ambati et al. |
| 2017/0251921 A1 | 9/2017 | Phan et al. |
| 2017/0252212 A1 | 9/2017 | Eutenuer et al. |
| 2017/0280997 A1 | 10/2017 | Lai et al. |
| 2017/0281409 A1 | 10/2017 | Haffner et al. |
| 2017/0290705 A1 | 10/2017 | Wardle et al. |
| 2017/0360609 A9 | 12/2017 | Schieber et al. |
| 2018/0369017 A1 | 12/2018 | Schieber et al. |
| 2019/0083313 A1 | 3/2019 | Berlin |
| 2019/0343679 A1 | 11/2019 | Wardle et al. |
| 2019/0380874 A1 | 12/2019 | Schieber et al. |
| 2020/0085620 A1 | 3/2020 | Euteneuer et al. |
| 2020/0261270 A1 | 8/2020 | Bertin |

FOREIGN PATENT DOCUMENTS

| | | |
|---|---|---|
| DE | 102012221350 A1 | 5/2014 |
| EP | 0168201 B1 | 6/1988 |
| EP | 0957949 A1 | 11/1996 |
| EP | 0766544 B1 | 5/1998 |
| EP | 1615604 B1 | 8/2009 |
| EP | 2193821 A1 | 6/2010 |
| EP | 1715827 B1 | 12/2010 |
| EP | 2380622 A1 | 10/2011 |
| EP | 2468327 A1 | 6/2012 |
| EP | 2471563 A1 | 7/2012 |
| EP | 1833440 B1 | 8/2012 |
| EP | 2521482 B1 | 8/2013 |
| EP | 3164061 A1 | 5/2017 |
| EP | 2996648 B1 | 6/2017 |
| EP | 1732484 B1 | 8/2017 |
| EP | 1740153 B2 | 8/2017 |
| EP | 3076948 A4 | 8/2017 |
| EP | 3205333 A1 | 8/2017 |
| EP | 3060180 A4 | 9/2017 |
| EP | 3082570 A4 | 9/2017 |
| JP | 10504978 A | 5/1998 |
| JP | 11123205 A | 5/1999 |
| JP | 2002542872 A | 12/2002 |
| JP | 2006517848 A | 8/2006 |
| JP | 2006289075 A | 10/2006 |
| JP | 2010509003 A | 3/2010 |
| JP | 2011502649 A | 1/2011 |
| WO | WO96/20742 A1 | 7/1996 |
| WO | WO99/01063 A1 | 1/1999 |

(56) References Cited

FOREIGN PATENT DOCUMENTS

| WO | WO99/45868 A1 | 9/1999 |
|---|---|---|
| WO | WO00/07525 A1 | 2/2000 |
| WO | WO00/13627 A1 | 3/2000 |
| WO | WO00/64389 A1 | 11/2000 |
| WO | WO00/64393 A1 | 11/2000 |
| WO | WO00/67687 A1 | 11/2000 |
| WO | WO01/89437 A2 | 11/2001 |
| WO | WO01/97727 A1 | 12/2001 |
| WO | WO02/36052 A1 | 5/2002 |
| WO | WO02/074052 A2 | 9/2002 |
| WO | WO02/080811 A2 | 10/2002 |
| WO | WO03/015659 A2 | 2/2003 |
| WO | WO03/045290 A1 | 6/2003 |
| WO | WO2004/054643 A1 | 7/2004 |
| WO | WO2004/093761 A1 | 11/2004 |
| WO | WO2005/105197 A2 | 11/2005 |
| WO | WO2006/066103 A2 | 6/2006 |
| WO | WO2007/035356 A2 | 3/2007 |
| WO | WO2007/047744 A2 | 4/2007 |
| WO | WO2007/087061 A2 | 8/2007 |
| WO | WO2008/002377 A1 | 1/2008 |
| WO | WO2008/005873 A2 | 1/2008 |
| WO | WO2009/049686 A1 | 4/2009 |
| WO | WO2009/120960 A2 | 10/2009 |
| WO | WO2011/035228 A1 | 3/2011 |
| WO | WO2011/035262 A1 | 3/2011 |
| WO | WO2011/053512 A1 | 5/2011 |
| WO | WO2011/057283 A1 | 5/2011 |
| WO | WO2011/083105 A1 | 7/2011 |
| WO | WO2011/106781 A1 | 9/2011 |
| WO | WO2011/150045 A1 | 12/2011 |
| WO | WO2012/037455 A1 | 3/2012 |
| WO | WO2012/051575 A2 | 4/2012 |
| WO | WO2012/083143 A1 | 6/2012 |
| WO | WO2012/136431 A1 | 10/2012 |
| WO | WO2013050073 A1 | 4/2013 |
| WO | WO2013/147978 A2 | 10/2013 |
| WO | WO2013174414 A1 | 11/2013 |
| WO | WO2016/154066 A2 | 9/2016 |
| WO | WO2017/030902 A2 | 2/2017 |
| WO | WO2017/030917 A1 | 2/2017 |
| WO | WO2017/062347 A1 | 4/2017 |
| WO | WO2017/087713 A1 | 5/2017 |
| WO | WO2017/095825 A1 | 6/2017 |
| WO | WO2017/132418 A1 | 8/2017 |
| WO | WO2017/132647 A1 | 8/2017 |
| WO | WO2017/156530 A1 | 9/2017 |

OTHER PUBLICATIONS

Schieber et al.; U.S. Appl. No. 16/805,217; entitled "Apparatus for delivering ocular implants into an anterior chamber of the eye," filed Feb. 28, 2020.
Schieber et al.; U.S. Appl. No. 16/828,054 entitled "Methods and devices for increasing aqueous humor outflow," filed Mar. 24, 2020.
Berlin et al.; U.S. Appl. No. 15/868,904 entitled Methods and systems for OCT guided glaucoma surgery, filed Jan. 11, 2018.
Cambridge Dictionary; Sensor (definition); 2 pages; retrived from the internet (http://dictionary.cambridge.org/define.asp?dict=CALD&key=71811 >) on Aug. 14, 2018.
Dietlein et al.; Morphological variability of the trabecular meshwork in glaucoma patients: implications for non-perforating glaucoma surgery; British Journal of Ophthalmology; 84(12); pp. 1354-1359; Dec. 2000.
Huang et al.; Optical coherence tomography; Science; 254(5035); pp. 1178-1181; 12 pages (Author Manuscript); Nov. 1991.
Johnstone; Aqueous humor outflow system overview; Becker-Shaffer's Diagnosis and Therapy of the Glaucomas; Part 2 Aqueous Humor Dynamics; Chapter 3; pp. 25-46; Mosby Elseveir; (year of pub. sufficiently earlier than effective US filing date and any foreign priority date) 2009.
Lee et al.; Short-pulsed neodymium-YAG laser trabeculotomy. An in vivo morphological study in the human eye; Investigative Ophthalmology and Visual Science; 29(11); pp. 1698-1707; Nov. 1988.
Macmilla Online Dictionary; Detector (definition); Macmilla On Line Dictionary; 2 pages; retrived from the internet (https://www.macmillandictionary.com/dictionary/british/detector) on Aug. 14, 2018.
Nakamura et al.; Femtosecond laser photodisruption of primate trabecular meshwork: an ex vivo study; Investigative Ophthalmology and Visual Science; 50(3); pp. 1198-1204; Mar. 2009.
Owen; A moving-mirror gonioscope for retinal surgery; British Journal of Ophthalmology; 61(3); pp. 246-247; Mar. 1977.
Oxford Dictionaries; Detector (definition); 1 page; retrieved from the internet (https://en.oxforddictionaries.com/definition/detector) on Aug. 14, 2018.
Oxford Dictionaries; Sensor (definition); 1 page; retrieved from te internet (http://www.askoxford.com/concise_oed/sensor?view=uk>) on Aug. 14, 2018.
Radhakrishnan et al.; Real-time optical coherence tomography of the anterior segment at 1310 nm; Archives of Opthhalmology; 119(8); pp. 1179-1185; Aug. 2001.
Toyran et al.; Femtosecond laser photodisruption of human trabecular meshwork: an in vitro study; Experimental Eye Research; 81(3); pp. 298-305; Sep. 2005.
Berlin; U.S. Appl. No. 16/525,267 entitled "Delivery system and method of use for the eye," filed Jul. 29, 2019.
Abate; Stanford team invents sensor that uses radio waves to detect subtle changes in pressure: device is used to monitor brain pressure in lab mice as prelude to possible use with human patients; future applications of this pressure-sensing technology could lead to touch-sensitive "skin" for prosthetic devices; 2 pages; Oct. 21, 2015; retrieved from the internet (http://engineering.stanford.edu/news/stanford-team-invents-sensor-uses-radio-waves-detect-subtle-changes-pressure).
Bahler, et al.; Trabecular bypass stents decrease intraocular pressure in cultured human anterior segments; Amer. Journal of Ophthalmology; vol. 138, No. 6; pp. 988-994.e2; Dec. 2004.
Camras et al.; A novel schlemm's canal scaffold increases outflow facility in a human anterior segment perfusion model; Invest. Opthalmol. Vis. Sci.; 53(10); pp. 6115-6121; Sep. 1, 2012.
D'Ermo, et al.; Our results with the operation of ab externo trabeculotomy; Ophthalmologica; vol. 163; pp. 347-355; Feb. 1971.
Ellingsen et al.; Trabeculotomy and sinusotomy in enucleated human eyes; Investigative Ophthalmology; vol. 11; pp. 21-28; Jan. 1972.
Fitzgerald; All about MEMS pressure sensors for medical devices; (Symposium Presentation); Medical Electronics Symposium; Portland OR; 30 pages; Sep. 19, 2014.
Grant; Experimental aqueous perfusion in enucleated human eyes; Archives of Ophthalmology; vol. 69; pp. 783-801; Jun. 1963.
Gulati et al.; A novel 8-mm schlemm's canal scaffold reduces outflow resistance in a human anterior segment perfusion model; Invest. Ophthalmol. Vis. Sci.; 54(3); pp. 1698-1704; Mar. 5, 2013.
Hays et al.; Improvement in outflow facility by two novel microinvasive glaucoma surgery implants; Invest. Ophthalmol. Vis. Sci.; 55(3); pp. 1893-1900; Mar. 1, 2014.
Johnstone et al.; "Microsurgery of Schlemm's Canal and the Human Aqueous Outflow System;" American Journal of Ophthalmology, vol. 76 (6): 906-917; Dec. 1973.
Johnstone et al.; Effects of a schlemm canal scaffold on collector channel ostia in human anterior segments; Exp. Eye. Res.; 119; pp. 70-76; Feb. 2014.
Kirkness et al.; The Use of Silicone Drainage Tubing to Control Post-Keratoplasty Glaucoma; Eye; 2 (pt 5); pp. 583-590; Apr. 1988.
Lee et al.; Aqueous-venous shunt and intraocular pressure. Preliminary report of animal studies; Investigative Ophthalmology; vol. 5; No. 1; pp. 59-64; Feb. 1966.
Lynch, Mary G.; U.S. Appl. No. 60/131,030 entitled "Devices and methods for treating glaucoma by enhancing aqueous outflow through schlemm's canal and anterior chamber angle," filed Apr. 26, 1999.

(56) References Cited

OTHER PUBLICATIONS

Mäepea et al.; The pressures in the episcleral veins, schlemm's canal and the trabecular meshwork in monkeys: effects of changes in intraocular pressure; Exp. Eye Res.; vol. 49; pp. 645-663; Oct. 1989.
Molteno et al.; Long Tube Implants in the Management of Glaucoma; SA Medical Journal; 26; pp. 1062-1066; Jun. 1976.
Molteno; New implant for drainage in glaucoma; Brit. J. Ophthal; 53; pp. 606-615; Sep. 1969.
Moses, Robert; The effect of intraocular pressure on resistance to outflow; Survey of Ophthalmology; vol. 22; No. 2; pp. 88-100; Sep.-Oct. 1977.
Rosenquist et al.; Outflow resistance of enucleated human eyes at two different perfusion pressures and different extents of trabeculotomy; Current Eye Res.; vol. 8; No. 12; pp. 1233-1240; Dec. 1989.
Savage, James; Gonioscopy in the management of glaucoma; Am. Academy of Ophthalmology; Focal Points; vol. XXIV; No. 3; pp. 1-14; Mar. 2006.
Schocket et al.; Anterior Chamber Tube Shunt to an Encircling Band in the Treatment of Neovascular Glaucoma and other Refractory Glaucomas; Ophthalmology; 92; pp. 553-562; Apr. 1985.
Schultz, Jared; Canaloplasty procedure shows promise for open-angle glaucoma in European study; Ocular Surgery News; vol. 34; Mar. 1, 2007.
Smit et al.; Effects of viscoelastic injection into schlemm's canal in primate and human eyes; J. Am. Academy of Ophthalmology; vol. 109; No. 4; pp. 786-792; Apr. 2002.
Spiegel et al.; Schlemm's canal implant: a new method to lower intraocular pressure in patients with POAG?; Ophthalmic Surgery and Lasers; vol. 30; No. 6; pp. 492-494; Jun. 1999.
Wilcox et al.; Hypothesis for Improving Accessory Filtration by Using Geometry; Journal of Glaucoma; 3; pp. 244-247; Fall 1994.
Yuan et al.; Mathematical modeling of outflow facility increase with trabecular meshwork bypass and schlemm canal dilation; J. Glaucoma; 10 pgs.; Mar. 24, 2015 (Epub ahead of print).
Sugiyama et al.; Micro-Diaphragm Pressure Sensor; 1986 International Electron Devices Meeting; pp. 184-187; Dec. 7, 1986.
Lazarus et al.; Farrofluid-based stretchable magnetic core inductors; In Journal of Physics: Conference Series; 660(1); 012007; 5 pages; retrieved from the internet (https://iopscience.iop.org/article/10.1088/1742-6596/660/1/012007/pdf) on Oct. 27, 2020.

* cited by examiner

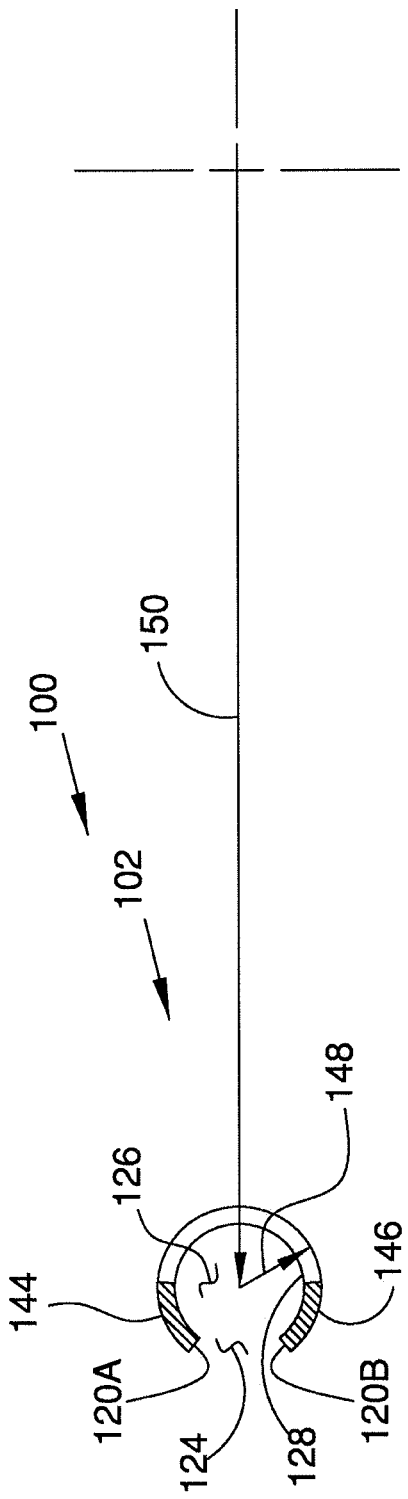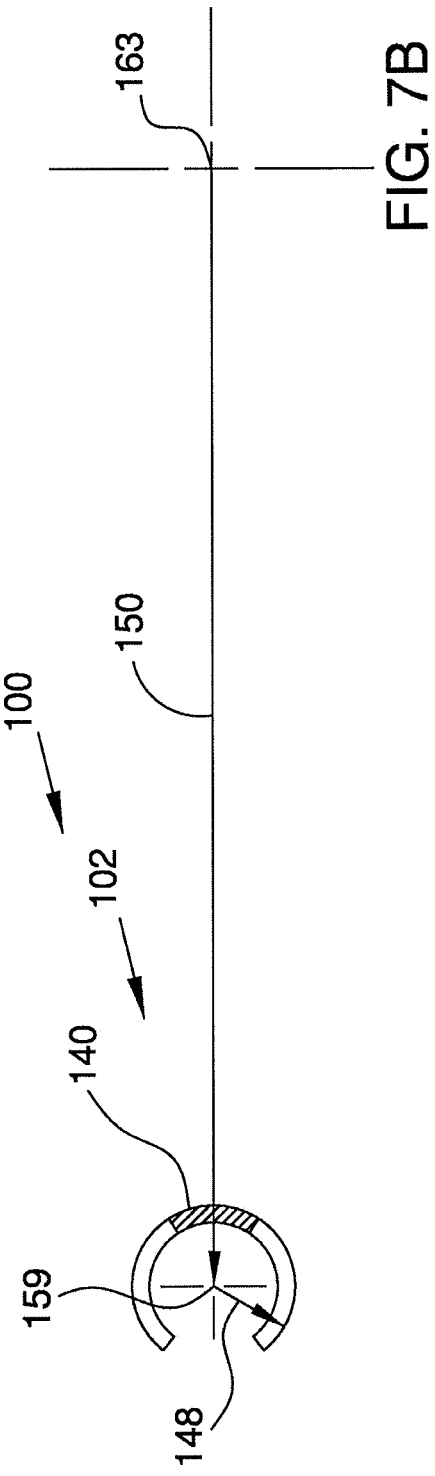

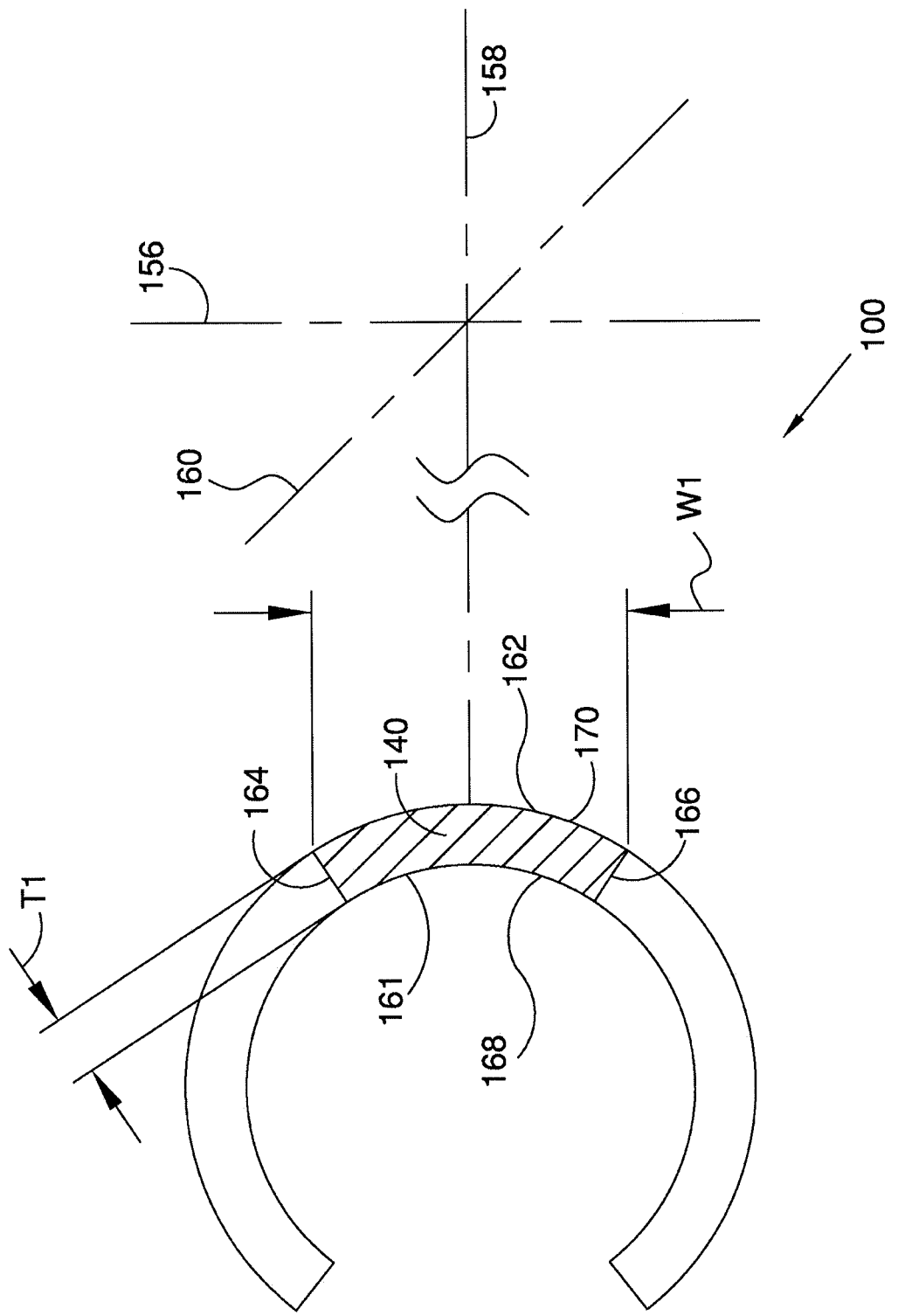

OCULAR IMPLANT WITH PRESSURE SENSOR AND DELIVERY SYSTEM

TECHNICAL FIELD

The present disclosure pertains generally, but not by way of limitation, to medical devices, and methods for manufacturing medical devices. The present invention relates generally to devices that are implanted within the eye. More particularly, the present invention relates to devices that facilitate the transfer of fluid from within one area of the eye to another area of the eye. Additionally, the present disclosure relates to systems, devices and methods for delivering ocular implants into the eye.

BACKGROUND

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma. For this reason, eye care professionals routinely screen patients for glaucoma by measuring intraocular pressure using a device known as a tonometer. Many modern tonometers make this measurement by blowing a sudden puff of air against the outer surface of the eye.

The eye can be conceptualized as a ball filled with fluid. There are two types of fluid inside the eye. The cavity behind the lens is filled with a viscous fluid known as vitreous humor. The cavities in front of the lens are filled with a fluid know as aqueous humor. Whenever a person views an object, he or she is viewing that object through both the vitreous humor and the aqueous humor.

Whenever a person views an object, he or she is also viewing that object through the cornea and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the anterior chamber of the eye through the trabecular meshwork and into Schlemm's canal as new aqueous humor is secreted by the epithelial cells of the ciliary body. This excess aqueous humor enters the venous blood stream from Schlemm's canal and is carried along with the venous blood leaving the eye.

When the natural drainage mechanisms of the eye stop functioning properly, the pressure inside the eye begins to rise. Researchers have theorized prolonged exposure to high intraocular pressure causes damage to the optic nerve that transmits sensory information from the eye to the brain. This damage to the optic nerve results in loss of peripheral vision. As glaucoma progresses, more and more of the visual field is lost until the patient is completely blind.

In addition to drug treatments, a variety of surgical treatments for glaucoma have been performed. For example, shunts were implanted to direct aqueous humor from the anterior chamber to the extraocular vein (Lee and Scheppens, "Aqueous-venous shunt and intraocular pressure," Investigative Opthalmology (February 1966)). Other early glaucoma treatment implants led from the anterior chamber to a sub-conjunctival bleb (e.g., U.S. Pat. Nos. 4,968,296 and 5,180,362). Still others were shunts leading from the anterior chamber to a point just inside Schlemm's canal (Spiegel et al., "Schlemm's canal implant: a new method to lower intraocular pressure in patients with POAG?" Ophthalmic Surgery and Lasers (June 1999); U.S. Pat. Nos. 6,450,984; 6,450,984).

SUMMARY

This disclosure provides design, material, and manufacturing method alternatives for medical devices.

In a first example, an ocular implant adapted to reside at least partially in a portion of Schlemm's canal of an eye may comprise a tubular body having an inner surface and an outer surface, the tubular body extending in a curved volume whose longitudinal axis forms an arc of a circle; a plurality of open areas and strut areas formed in the tubular body, the strut areas surrounding the plurality of open areas; a pressure sensor disposed on the inner surface of the tubular body; and the tubular body having a diameter of between 0.005 inches and 0.04 inches.

Alternatively or additionally to any of the embodiments above, the pressure sensor comprises a micro-electro-mechanical system (MEMS) pressure sensor.

Alternatively or additionally to any of the embodiments above, the pressure sensor includes an antenna for transmitting data from the pressure sensor to a remote location.

Alternatively or additionally to any of the embodiments above, the data is automatically transmitted from the remote location to a second remote device.

Alternatively or additionally to any of the embodiments above, the strut areas are connected by one or more spine areas.

Alternatively or additionally to any of the embodiments above, each strut area undulates in a circumferential direction as it extends longitudinally between a first spine area and a second spine area.

Alternatively or additionally to any of the embodiments above, the implant is formed from shape memory material in a shape approximately equal to the curved volume.

Another example system comprises a cannula defining a passageway extending from a proximal end to a distal end, the cannula having a distal opening extending through a side wall and the distal end of the cannula to form a trough, a curved distal portion, a curved intermediate portion, and a proximal portion, the cannula further including a first pressure sensor disposed within the trough; an ocular implant disposed within the passageway of the cannula; and a delivery tool having a distal interlocking portion engaging a complementary interlocking portion of the ocular implant.

Alternatively or additionally to any of the embodiments above, the first pressure sensor comprises a micro-electromechanical system (MEMS) pressure sensor.

Alternatively or additionally to any of the embodiments above, the first pressure sensor includes an antenna for transmitting data from the first pressure sensor to a remote location.

Alternatively or additionally to any of the embodiments above, further comprising a second pressure sensor disposed on or within the ocular implant.

Alternatively or additionally to any of the embodiments above, the second pressure sensor comprises a micro-electro-mechanical system (MEMS) pressure sensor.

Alternatively or additionally to any of the embodiments above, the second pressure sensor includes an antenna for transmitting data from the second pressure sensor to a remote location.

Alternatively or additionally to any of the embodiments above, the distal interlocking portion of the delivery tool and the complementary interlocking portion of the ocular implant form a mechanically interlocking connection when the interlocking portion of the delivery tool is proximal to the trough of the cannula.

Another example ocular implant kit comprises an ocular implant adapted to reside at least partially in a portion of Schlemm's canal of an eye, the implant comprising a tubular body having an inner surface and an outer surface, the tubular body extending in a curved volume whose longitudinal axis forms an arc of a circle; and a plurality of open areas and strut areas formed in the tubular body, the strut areas surrounding the plurality of open areas; a first pressure sensor disposed on the inner surface of the tubular body; and the tubular body having a diameter of between 0.005 inches and 0.04 inches. The kit further comprising a cannula defining a passageway extending from a proximal end to a distal end, the cannula having a distal opening extending through a side wall and the distal end of the cannula to form a trough, a curved distal portion, a curved intermediate portion, and a proximal portion; and a delivery tool having a distal interlocking portion engaging a complementary interlocking portion of the ocular implant.

Alternatively or additionally to any of the embodiments above, the first pressure sensor comprises a micro-electromechanical system (MEMS) pressure sensor.

Alternatively or additionally to any of the embodiments above, the first pressure sensor includes an antenna for transmitting data from the first pressure sensor to a remote location.

Alternatively or additionally to any of the embodiments above, the data is automatically transmitted from the remote location to a second remote device.

Alternatively or additionally to any of the embodiments above, further comprising a second pressure sensor disposed within the trough of the cannula.

Alternatively or additionally to any of the embodiments above, the second pressure sensor comprises a micro-electro-mechanical system (MEMS) pressure sensor and includes an antenna for transmitting data from the second pressure sensor to a remote location.

The above summary of some examples and embodiments is not intended to describe each disclosed embodiment or every implementation of the present disclosure. The Brief Description of the Drawings, and Detailed Description, which follow, more particularly exemplify these embodiments, but are also intended as exemplary and not limiting.

BRIEF DESCRIPTION OF THE DRAWINGS

The disclosure may be more completely understood in consideration of the following detailed description of various embodiments in connection with the accompanying drawings, in which:

FIG. 7A is a lateral cross-sectional view of the ocular implant of FIG. 6 taken along section line A-A of FIG. 6.

FIG. 7B is a lateral cross-sectional view of the ocular implant of FIG. 6 taken along section line B-B of FIG. 6.

FIG. 8 is an enlarged cross-sectional view of the ocular implant of FIG. 6 taken along section line B-B of FIG. 6.

Figure 1:
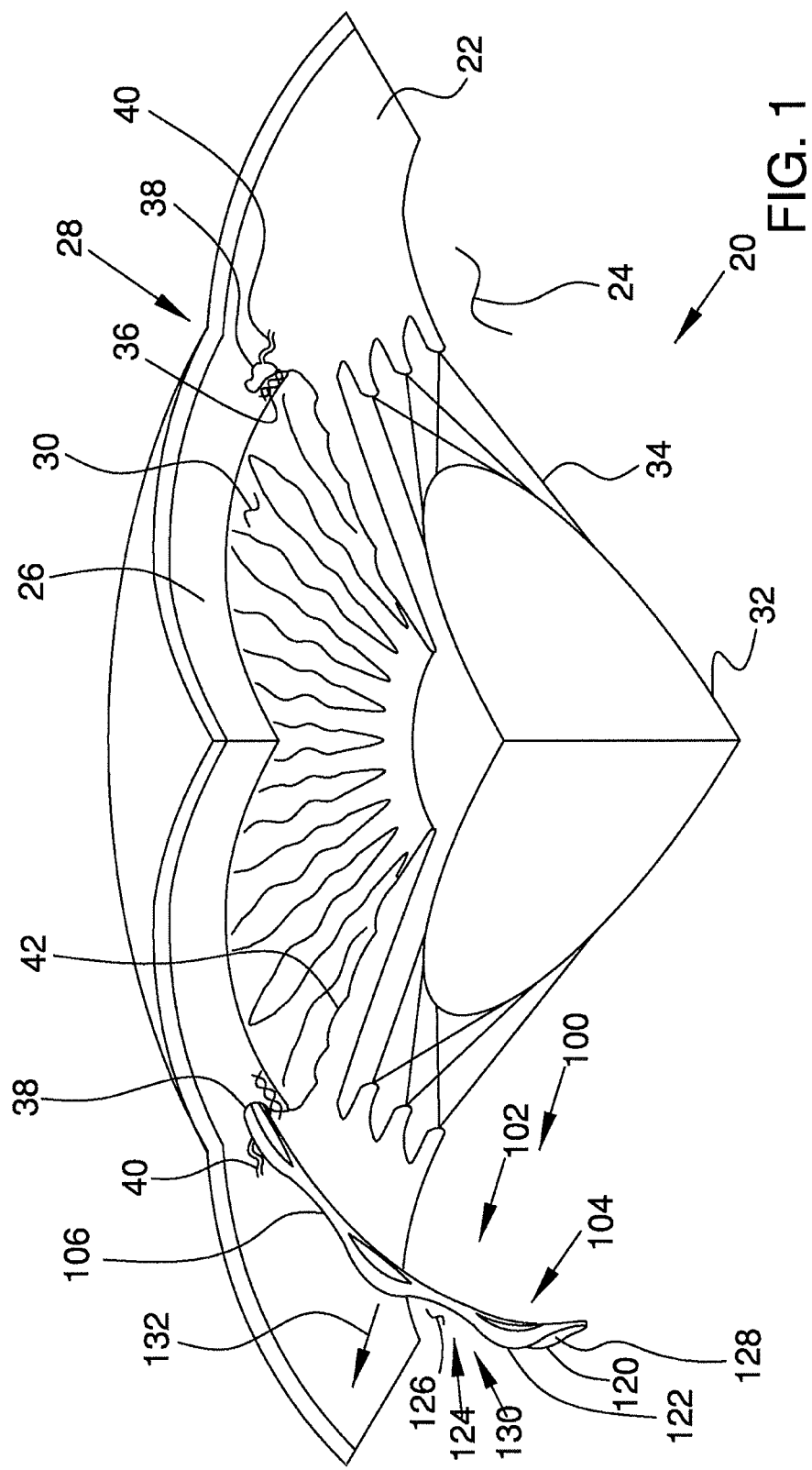
FIG. 1 is a stylized perspective view depicting a portion of a human eye and a portion of an ocular implant disposed in Schlemm's canal.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

Definitions of certain terms are provided below and shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or able to be arranged with each other to form other additional embodiments or to complement and/or enrich the described embodiment(s), as would be understood by one of ordinary skill in the art.

The following detailed description should be read with reference to the drawings, in which similar elements in different drawings are identified with the same reference numbers. The drawings, which are not necessarily to scale, depict illustrative embodiments and are not intended to limit the scope of the disclosure.

FIG. 1 is a stylized perspective view depicting a portion of a human eye 20. Eye 20 can be conceptualized as a fluid filled ball having two chambers. Sclera 22 of eye 20 surrounds a posterior chamber 24 filled with a viscous fluid known as vitreous humor. Cornea 26 of eye 20 encloses an anterior chamber 30 that is filled with a fluid know as aqueous humor. The cornea 26 meets the sclera 22 at a limbus 28 of eye 20. A lens 32 of eye 20 is located between anterior chamber 30 and posterior chamber 24. Lens 32 is held in place by a number of ciliary zonules 34. Whenever a person views an object, he or she is viewing that object through the cornea, the aqueous humor, and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the eye as new aqueous humor is secreted by the epithelial cells of the ciliary body. This excess aqueous humor enters the blood stream and is carried away by venous blood leaving the eye.

In a healthy eye, aqueous humor flows out of the anterior chamber 30 through the trabecular meshwork 36 and into Schlemm's canal 38, located at the outer edge of the iris 42. Aqueous humor exits Schlemm's canal 38 by flowing through a number of outlets 40. After leaving Schlemm's canal 38, aqueous humor is absorbed into the venous blood stream.

In FIG. 1, an ocular implant 100 is disposed in Schlemm's canal 38 of eye 20. Ocular implant 100 has a body 102 including a plurality of tissue supporting frames 104 and a plurality of spines 106. Body 102 also includes a first edge 120 and a second edge 122 that define a first opening 124. First opening 124 is formed as a slot and fluidly communicates with an elongate channel 126 defined by an inner surface 128 of body 102. With reference to FIG. 1, it will be appreciated that first opening 124 is disposed on an outer side 130 of body 102. Accordingly, channel 126 opens in a radially outward direction 132 via first opening 124.

Ocular implant 100 may be inserted into Schlemm's canal of a human eye to facilitate the flow of aqueous humor out of the anterior chamber. This flow may include axial flow along Schlemm's canal, flow from the anterior chamber into Schlemm's canal, and flow leaving Schlemm's canal via outlets communicating with Schlemm's canal. When in place within the eye, ocular implant 100 will support trabecular mesh tissue and Schlemm's canal tissue and will provide for improved communication between the anterior chamber and Schlemm's canal (via the trabecular meshwork) and between pockets or compartments along Schlemm's canal. As shown in FIG. 1, the implant is preferably oriented so that the first opening 124 is disposed radially outwardly within Schlemm's canal.

Figure 2:
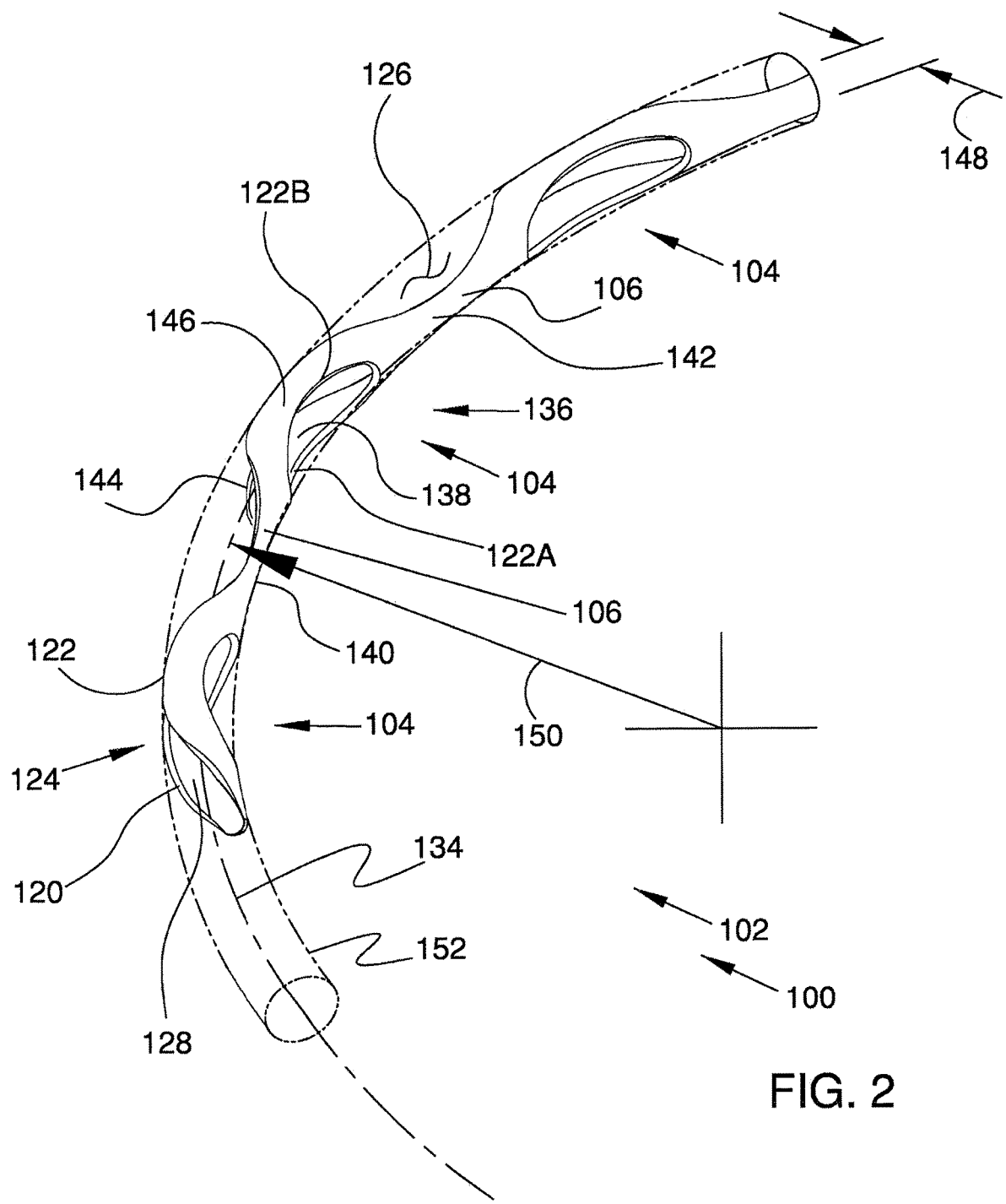
FIG. 2 is an enlarged perspective view showing a portion of the implant of FIG. 1.

FIG. 2 is an enlarged perspective view showing a portion of ocular implant 100 shown in the previous figure. Ocular implant 100 has a body 102 that extends along a generally curved longitudinal axis 134. Body 102 has a plurality of tissue supporting frames 104 and a plurality of spines 106. As shown in FIG. 2, these spines 106 and frames 104 are arranged in a repeating AB pattern in which each A is a tissue supporting frame and each B is a spine. In the embodiment of FIG. 2, one spine extends between each adjacent pair of frames 104

The frames 104 of body 102 include a first frame 136 of ocular implant 100 that is disposed between a first spine 140 and a second spine 142. In the embodiment of FIG. 2, first frame 136 is formed as a first strut 144 that extends between first spine 140 and second spine 142. First frame 136 also includes a second strut 146 extending between first spine 140 and second spine 142. In the exemplary embodiment of FIG. 2, each strut undulates in a circumferential direction as it extends longitudinally between first spine 140 and second spine 142.

In the embodiment of FIG. 2, body 102 has a longitudinal radius 150 and a lateral radius 148. Body 102 of ocular implant 100 includes a first edge 120 and a second edge 122 that define a first opening 124. First opening 124 fluidly communicates with an elongate channel 126 defined by an inner surface 128 of body 102. A second opening 138 is defined by a second edge 122A of a first strut 144 and a second edge 122B of a second strut 146. First opening 124, second opening 138 and additional openings defined by ocular implant 100 allow aqueous humor to flow laterally across and/or laterally through ocular implant 100. The outer surfaces of body 102 define a volume 152.

Figure 3:
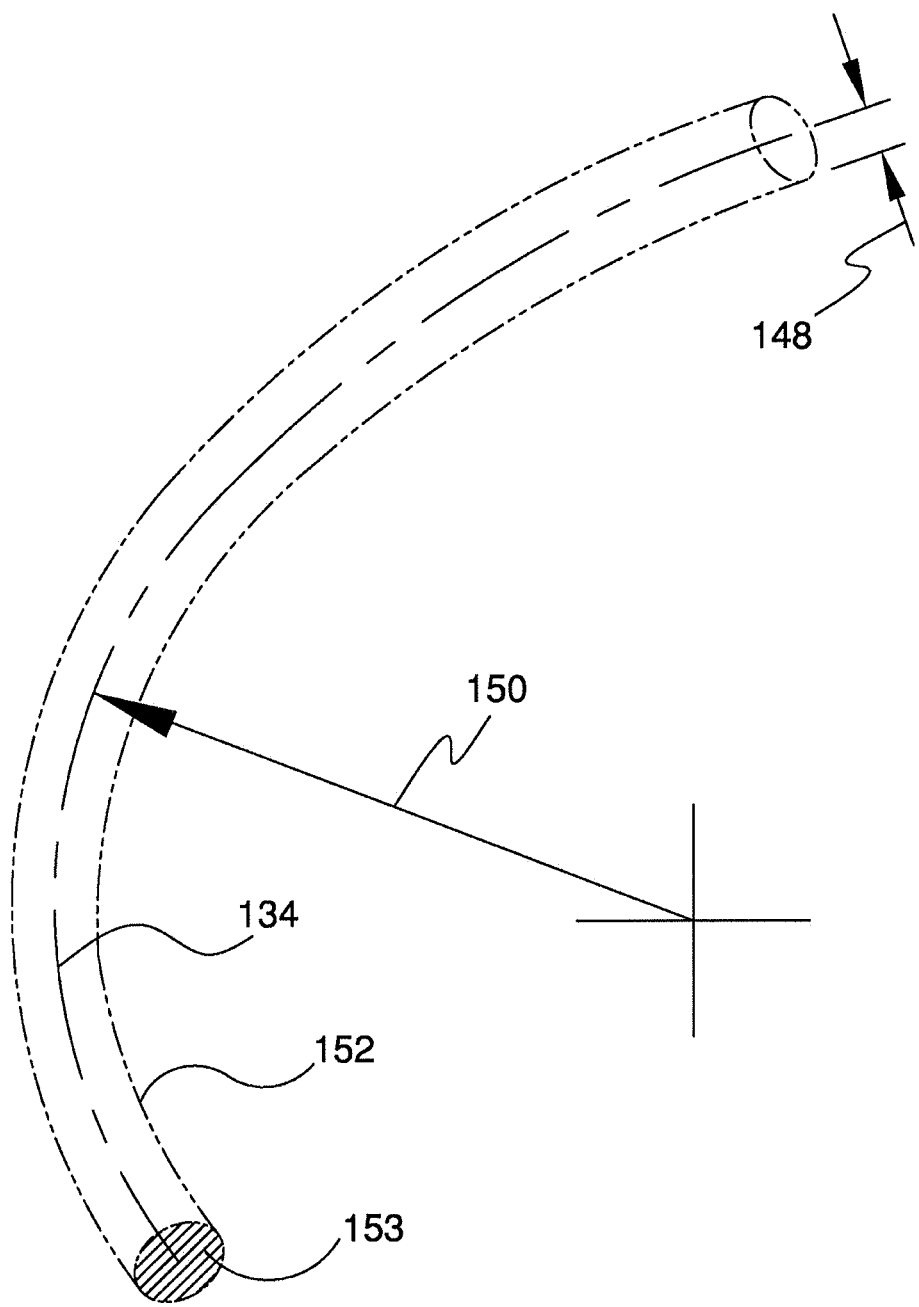
FIG. 3 is a perspective view showing a volume defined by the body of the ocular implant of FIGS. 1 and 2.

FIG. 3 is an additional perspective view showing volume 152 defined by the body of the ocular implant shown in the previous figure. With reference to FIG. 3, it will be appreciated that volume 152 extends along a generally curved longitudinal axis 134. Volume 152 has a longitudinal radius 150, a lateral radius 148, and a generally circular lateral cross section 153.

Figure 4:
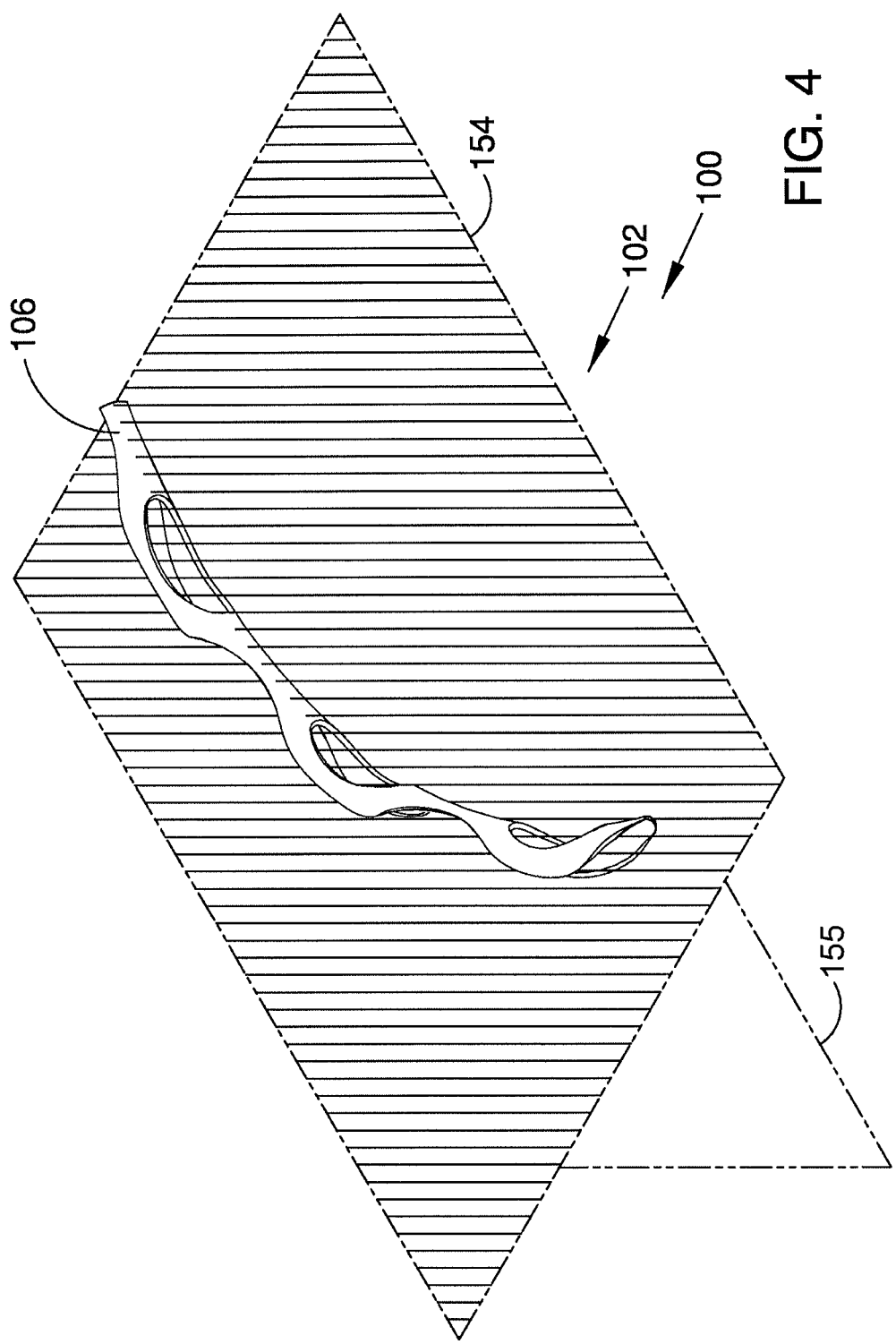
FIG. 4 is a perspective view showing a first plane intersecting the body of an ocular implant.

FIG. 4 is a perspective view showing a first plane 154 and a second plane 155 that both intersect ocular implant 100. In FIG. 4, first plane 154 is delineated with hatch marks. With reference to FIG. 4, it will be appreciated that spines 106 of body 102 are generally aligned with one another and that first plane 154 intersects all spines 106 shown in FIG. 4. In the embodiment of FIG. 4, body 102 of ocular implant 100 is generally symmetric about first plane 154.

In the embodiment of FIG. 4, the flexibility of body 102 is at a maximum when body 102 is bending along first plane 154, and body 102 has less flexibility when bending along a plane other than first plane 154 (e.g., a plane that intersects first plane 154). For example, in the embodiment shown in FIG. 4, body 102 has a second flexibility when bending along second plane 155 that is less than the first flexibility that body 102 has when bending along first plane 154.

Stated another way, in the embodiment of FIG. 4, the bending modulus of body 102 is at a minimum when body 102 is bent along first plane 154. Body 102 has a first bending modulus when bent along first plane 154 and a greater bending modulus when bent along a plane other than first plane 154 (e.g., a plane that intersects first plane 154). For example, in the embodiment shown in FIG. 4, body 102 has a second bending modulus when bent along second plane 155 that is greater than the first bending modulus that body 102 has when bent along first plane 154.

Figure 5:
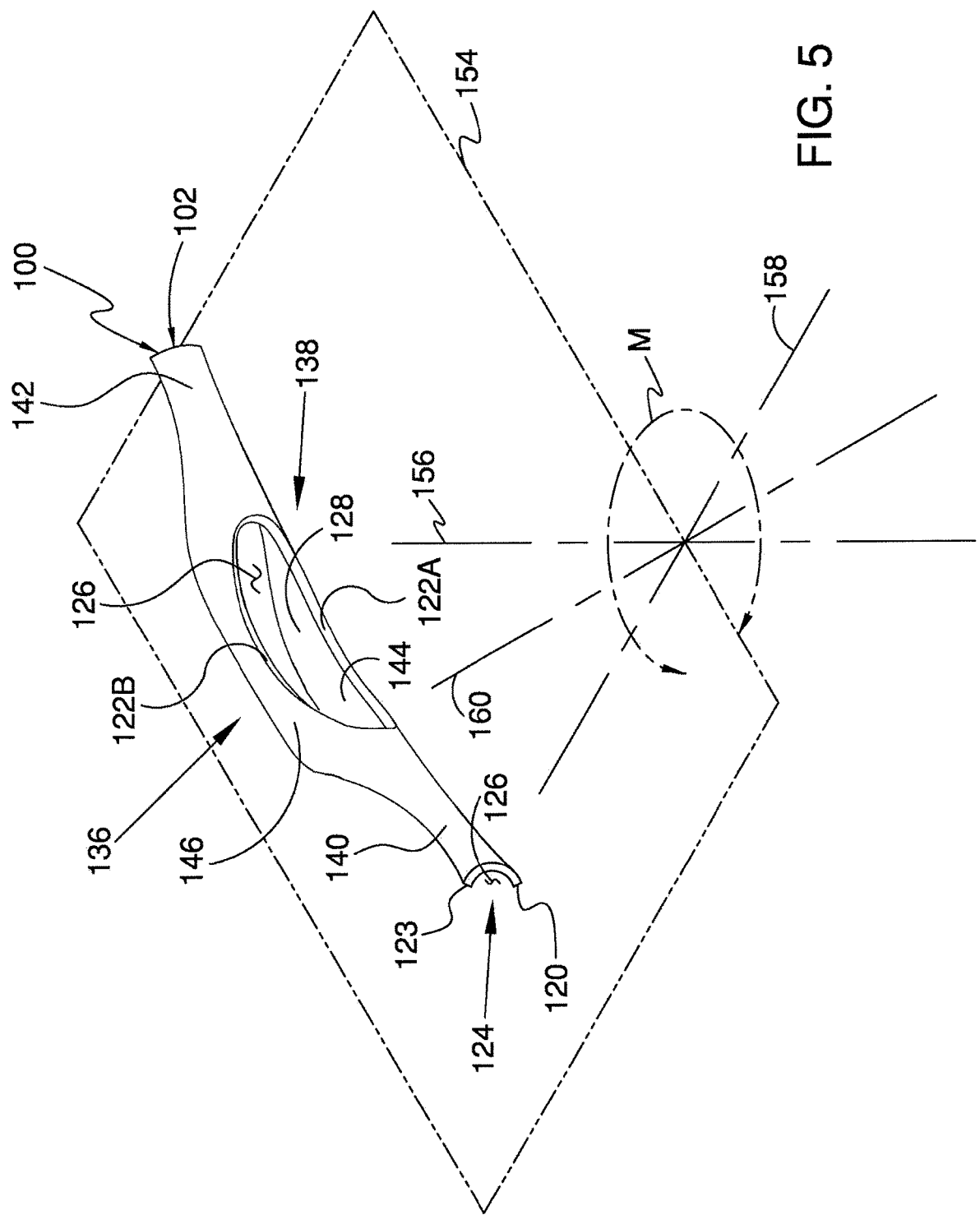
FIG. 5 is a perspective view showing a bending moment being applied to an ocular implant.

FIG. 5 is an enlarged perspective view showing a portion of ocular implant 100 shown in the previous figure. In the exemplary embodiment of FIG. 5, a bending moment M is being applied to body 102 of ocular implant 100. Bending moment M acts about a first axis 156 that is generally orthogonal to first plane 154. A second axis 158 and a third axis 160 are also shown in FIG. 5. Second axis 158 is generally perpendicular to first axis 156. Third axis 160 is skewed relative to first axis 156.

An inner surface 128 of body 102 defines a channel 126. Body 102 of ocular implant 100 includes a first edge 120 and a second edge 123 that define a first opening 124. Channel 126 of ocular implant 100 fluidly communicates with first opening 124. A second opening 138 is defined by a second edge 122A of a first strut 144 and a second edge 122B of a second strut 146. First opening 124, second opening 138 and additional openings defined by ocular implant 100 allow aqueous humor to flow laterally across and/or laterally through ocular implant 100.

As shown in FIG. 5, ocular implant 100 has a first spine 140 and a second spine 142. First strut 144 and a second strut 146 form a first frame 136 of ocular implant 100 that extends between first spine 140 and second spine 142. In the exemplary embodiment of FIG. 5, each strut undulates in a circumferential direction as it extends longitudinally between first spine 140 and second spine 142.

In the embodiment of FIG. 5, the flexibility of body 102 is at a maximum when body 102 is bent by a moment acting about first axis 156, and body 102 has less flexibility when bent by a moment acting about an axis other than first axis 156 (e.g., second axis 158 and third axis 160). Stated another way, the bending modulus of body 102 is at a minimum when body 102 is bent by a moment acting about first axis 156, and body 102 has a greater bending modulus when bent by a moment acting about an axis other than first axis 156 (e.g., second axis 158 and third axis 160).

Figure 6:
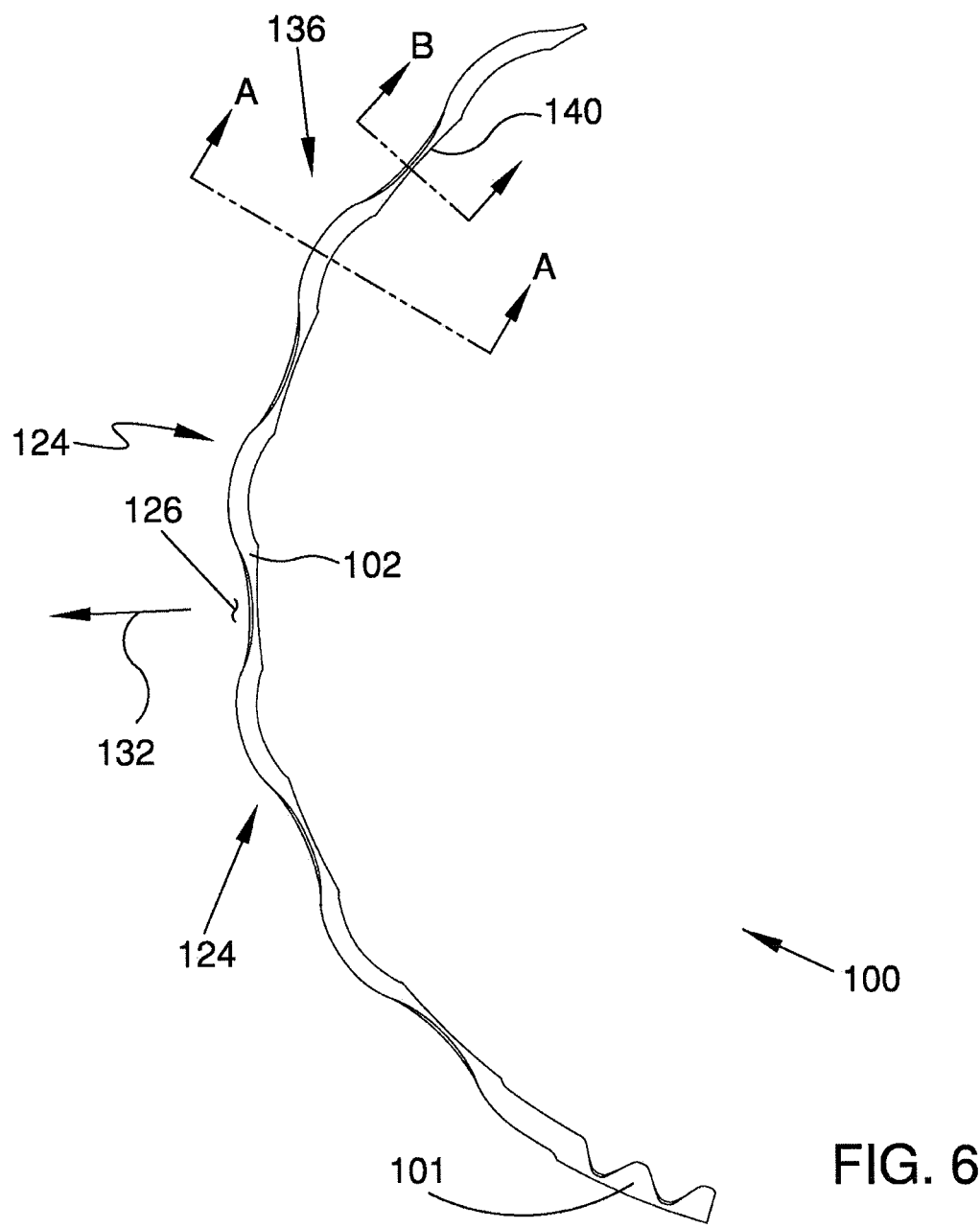
FIG. 6 is a plan view of the implant shown in FIG. 5 but in the absence of any bending moment.

FIG. 6 is a plan view showing ocular implant 100 shown in the previous figure. In the embodiment of FIG. 6, no external forces are acting on body 102 of ocular implant 100, and body 102 is free to assume the generally curved resting shape depicted in FIG. 6. Body 102 defines a first opening 124 that is disposed on an outer side 130 of body 102. A channel 126 is defined by the inner surface of body 102 and opens in a radially outward direction 132 via first opening 124. A proximal end 101 of the ocular implant 100 may include an interlocking portion configured to mate with and/or engage a complementary interlocking portion of a delivery tool. Section lines A-A and B-B are visible in FIG. 6. Section line A-A intersects a first frame 136 of ocular implant 100. Section line B-B intersects a first spine 140 of ocular implant 100.

FIG. 7A is a lateral cross-sectional view of ocular implant 100 taken along section line A-A shown in the previous figure. Section line A-A intersects a first strut 144 and a second strut 146 of first frame 136 at the point where the circumferential undulation of these struts is at its maximum. Body 102 of ocular implant 100 has a longitudinal radius 150 and a lateral radius 148. An inner surface 128 of body 102 defines a channel 126. A first opening 124 fluidly communicates with channel 126.

In FIG. 7A, first opening 124 in body 102 can be seen extending between first edge 120A of first strut 144 and a first edge 120B of second strut 146. With reference to FIG. 7A, it will be appreciated that second strut 146 has a shape that is a mirror image of the shape of first strut 144.

FIG. 7B is a lateral cross-sectional view of ocular implant 100 taken along section line B-B shown in the previous figure. Section line B-B intersects first spine 140 of ocular implant 100. Body 102 has a longitudinal radius 150 and a lateral radius 148. In the embodiment of FIG. 7B, the center 159 of lateral radius 148 and the center 163 of longitudinal radius 150 are disposed on opposite sides of first spine 140. The center 159 of lateral radius 148 is disposed on a first side of first spine 140. The center 163 of longitudinal radius 150 is disposed on a second side of second spine 142.

FIG. 8 is an enlarged cross-sectional view of ocular implant 100 taken along section line B-B of FIG. 6. First spine 140 includes a first major side 161, a second major side 162, a first minor side 164, and second minor side 166. With reference to FIG. 8, it will be appreciated that first major side 161 comprises a concave surface 168. Second major side 162 is opposite first major side 161. In the embodiment of FIG. 8, second major side 162 comprises a convex surface 170.

The geometry of the spine provides the ocular implant with flexibility characteristics that may aid in advancing the ocular implant into Schlemm's canal. In the embodiment of FIG. 8, first spine 140 has a thickness T1 extending between first major side 161 and second major side 162. Also in the embodiment of FIG. 8, first spine 140 has a width W1 extending between first minor side 164 and second minor side 166.

In some useful embodiments, the spine of an ocular implant in accordance with this detailed description has an aspect ratio of width W1 to thickness T1 greater than about 2. In some particularly useful embodiments, the spine of an ocular implant in accordance with this detailed description has an aspect ratio of width W1 to thickness T1 greater than about 4. In one useful embodiment, the ocular implant has a spine with an aspect ratio of width W1 to thickness T1 of about 5.2.

A first axis 156, a second axis 158 and a third axis 160 are shown in FIG. 8. Second axis 158 is generally perpendicular to first axis 156. Third axis 160 is skewed relative to first axis 156.

In the embodiment of FIG. 8, the flexibility of first spine 140 is at a maximum when first spine 140 is bent by a moment acting about first axis 156. First spine 140 has a first flexibility when bent by a moment acting about first axis 156 and less flexibility when bent by a moment acting about an axis other than first axis 156 (e.g., second axis 158 and third axis 160). For example, first spine 140 has a second flexibility when bent by a moment acting about second axis 158 shown in FIG. 8. This second flexibility is less than the first flexibility that first spine 140 has when bent by a moment acting about first axis 156.

In the embodiment of FIG. 8, the bending modulus of first spine 140 is at a minimum when first spine 140 is bent by a moment acting about first axis 156. First spine 140 has a first bending modulus when bent by a moment acting about first axis 156 and a greater bending modulus when bent by a moment acting about an axis other than first axis 156 (e.g., second axis 158 and third axis 160). For example, first spine 140 has a second bending modulus when bent by a moment acting about second axis 158 shown in FIG. 8. This second bending modulus is greater than the first bending modulus that first spine 140 has when bent by a moment acting about first axis 156.

Figure 9:
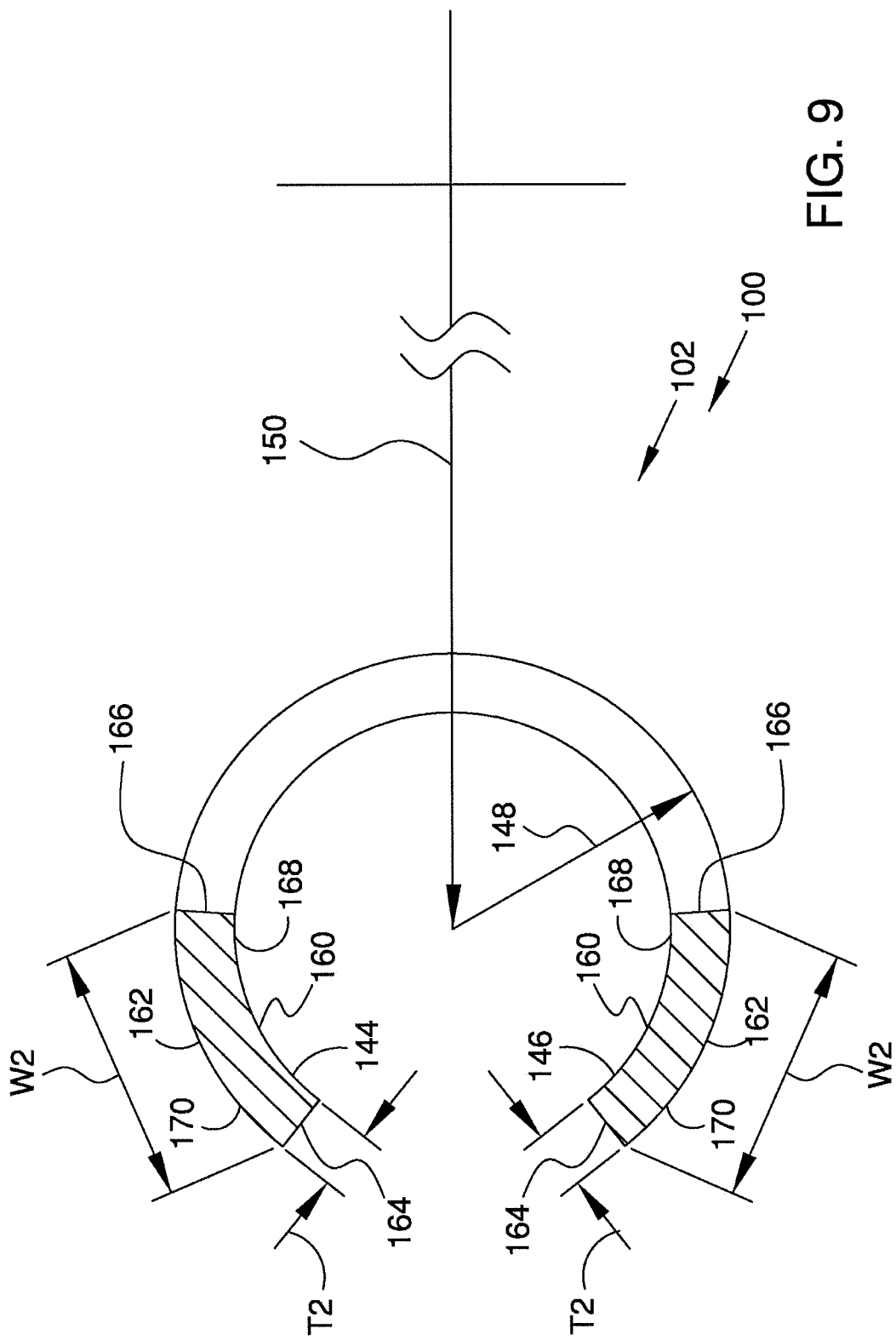
FIG. 9 is an enlarged cross-sectional view of the ocular implant of FIG. 6 taken along section line A-A of FIG. 6.

FIG. 9 is an enlarged cross-sectional view of ocular implant 100 taken along section line A-A of FIG. 6. Section line A-A intersects first strut 144 and second strut 146 at the point where the circumferential undulation of these struts is at its maximum.

Each strut shown in FIG. 9 includes a first major side 161, a second major side 162, a first minor side 164, and second minor side 166. With reference to FIG. 9, it will be appreciated that each first major side 161 comprises a concave surface 168 and each second major side 162 comprises a convex surface 170.

In the embodiment of FIG. 9, each strut has a thickness T2 extending between first major side 161 and second major side 162. Also in the embodiment of FIG. 9, each strut has a width W2 extending between first minor side 164 and second minor side 166. In some useful embodiments, an ocular implant in accordance with this detailed description includes spines having a width W1 that is greater than the width W2 of the struts of the ocular implant.

In some useful embodiments, the struts of an ocular implant in accordance with this detailed description have an aspect ratio of width W2 to thickness T2 greater than about 2. In some particularly useful embodiments, the struts of an ocular implant in accordance with this detailed description have an aspect ratio of width W2 to thickness T2 greater than about 4. One exemplary ocular implant has struts with an aspect ratio of width W2 to thickness T2 of about 4.4.

Body 102 of ocular implant 100 has a longitudinal radius 150 and a lateral radius 148. In some useful embodiments, an ocular implant in accordance with this detailed description is sufficiently flexible to assume a shape matching the longitudinal curvature of Schlemm's canal when the ocular implant advanced into the eye. Also in some useful embodiments, a length of the ocular implant is selected so that the implant will extend across a pre-selected angular span when the implant is positioned in Schlemm's canal. Examples of pre-selected angular spans that may be suitable in some applications include 60°, 90°, 150° and 180°. The diameter of an ocular implant in accordance with this detailed description may be selected so that the ocular implant is dimensioned to lie within and support Schlemm's canal. In some useful embodiments, the diameter of the ocular implant ranges between about 0.005 inches (0.127 millimeters) and about 0.04 inches (1.016 millimeters). In some particularly useful embodiments, the diameter of the ocular implant ranges between about 0.005 inches (0.127 millimeters) and about 0.02 inches (0.508 millimeters).

Figure 13:
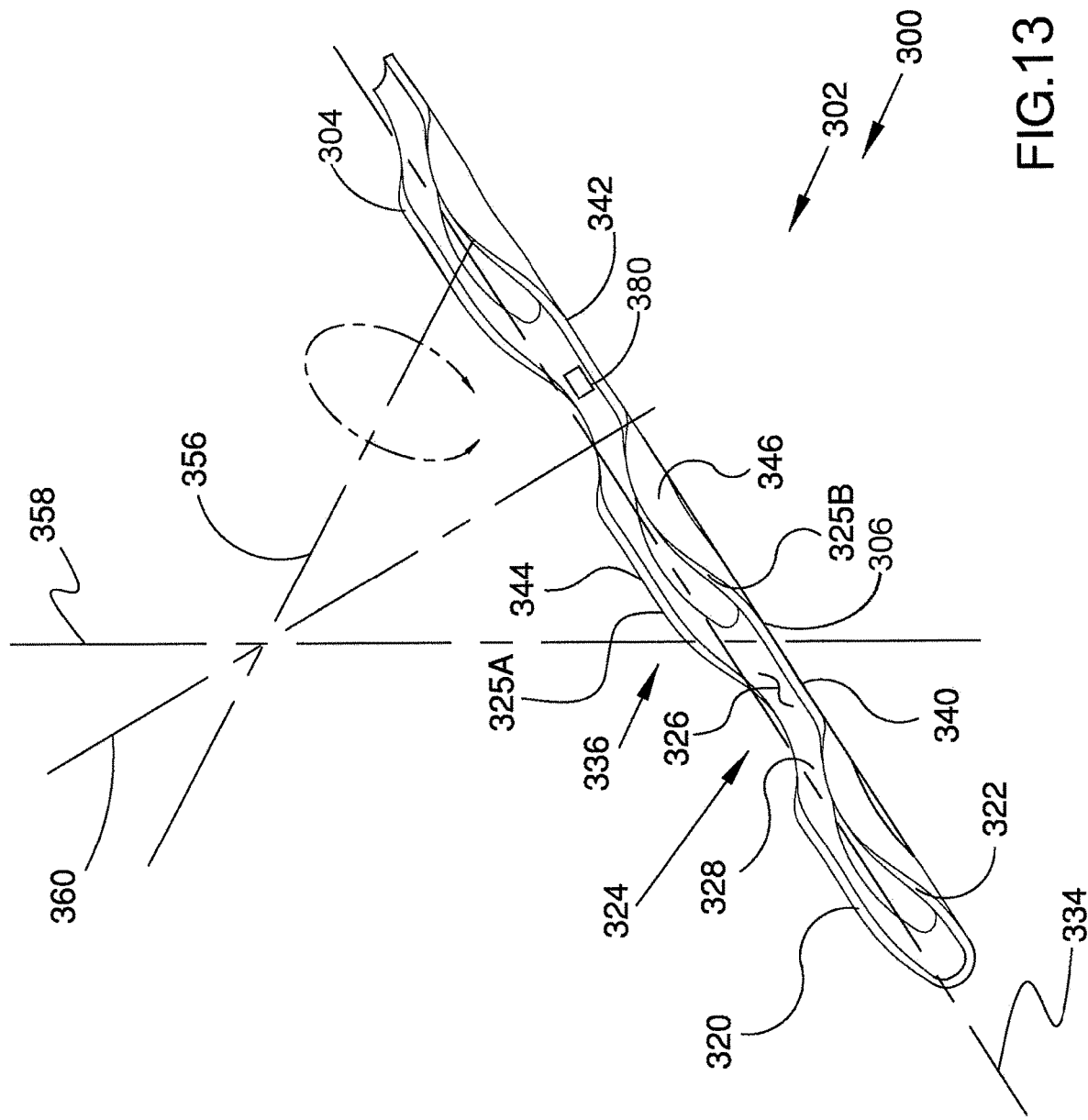
FIG. 13 is a perspective view showing an ocular implant according to yet another embodiment of the invention that has substantially no radius of curvature.

It is to be appreciated that an ocular implant in accordance with the present detailed description may be straight or curved. If the ocular implant is curved, it may have a substantially uniform longitudinal radius throughout its length, or the longitudinal radius of the ocular implant may vary along its length. FIG. 6 shows one example of an ocular implant having a substantially uniform radius of curvature. FIG. 10 shows one example of an ocular implant having a longitudinal radius of curvature that varies along the length of the ocular implant. An example of a substantially straight ocular implant is shown in FIG. 13.

Figure 10A:
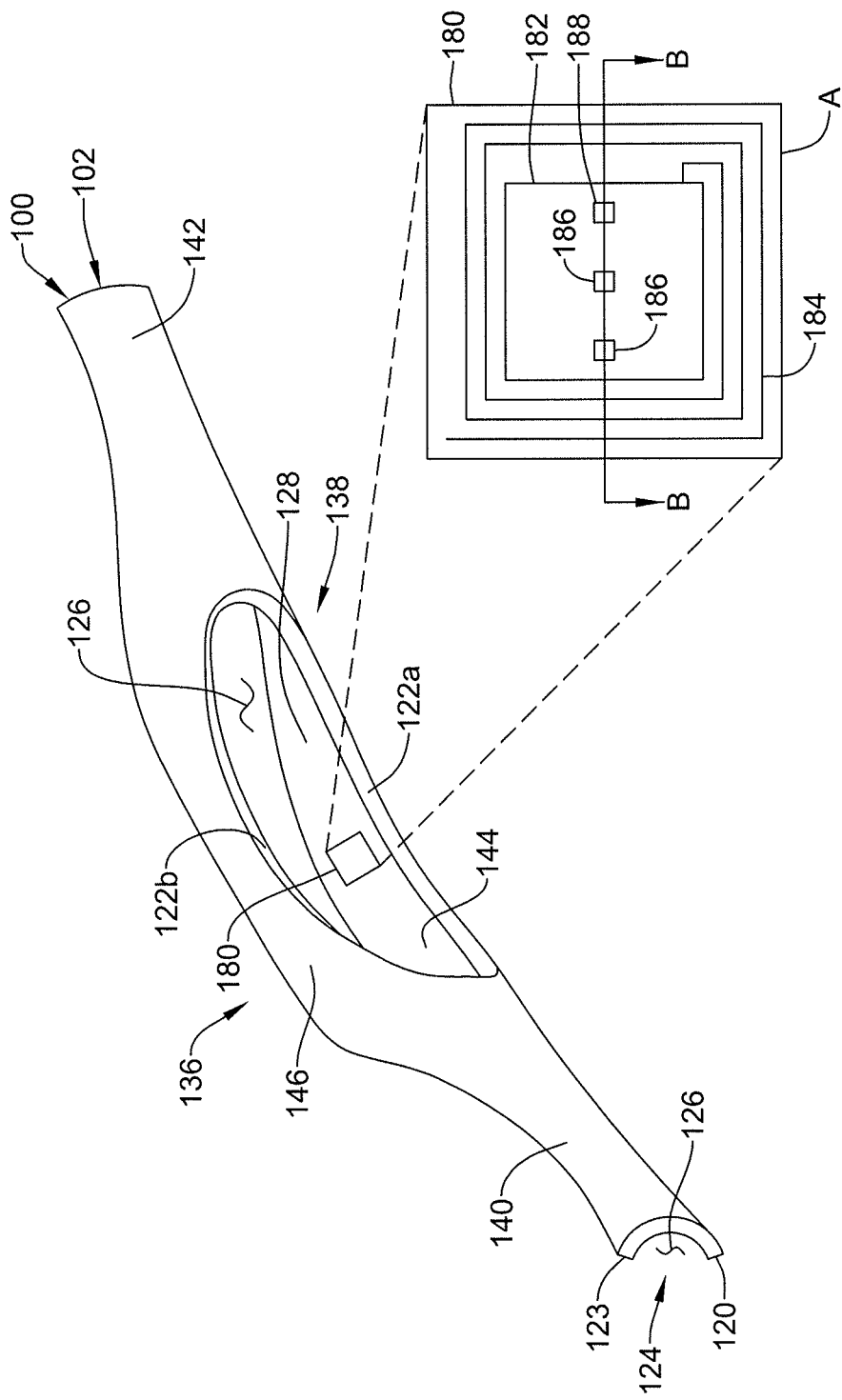
FIG. 10A is an enlarged perspective view of a portion of the ocular implant including a pressure sensor.

FIG. 10A is an enlarged perspective view showing a portion of ocular implant 100 shown in the FIGS. 2 and 4. The ocular implant 100 may further include an intraocular pressure sensor 180 mounted to the inner surface 128 of the ocular implant 100 adjacent to an outlet of the implant 100, as shown in Detail A. While the pressure sensor 180 is illustrated as mounted to an inner surface 128 of the ocular implant 100 it is contemplated that the pressure sensor 180 may be mounted within one of the openings 124, 138 or on an outer surface of the ocular implant 100, as desired. The pressure sensor 180 may continuously measure the intraocular pressure of a patient, once the ocular implant 100 has been implanted.

The pressure sensor 180 may be a Micro-Electro-Mechanical System (MEMS) pressure sensor. While the pressure sensor 180 has been described as a MEMS pressure sensor, it is contemplated that other pressure sensors may be used in place of, or in addition to, a MEMS pressure sensor. In some instances, the pressure sensor 180 may have a width in the range of approximately 0.02 millimeters (20 micrometers) to approximately 1.0 millimeters. However, it is contemplated that the pressure sensors 180 are smaller than 20 micrometers, or larger than 1.0 millimeter. In some instances, the pressure sensor 180 may have a width dimension in the nanometer range. Further, while only a single pressure sensor 180 has been illustrated, the ocular implant 100 may include more than one pressure sensor 180, as desired. For example, a first pressure sensor may be placed at a first end of the ocular implant 100 and a second pressure sensor may be placed at a second end of the ocular implant. In some instances, the pressure sensor 180 may be provided in the channel 128 adjacent to the proximal end 101 of the implant 100, as shown in FIG. 10C. It is contemplated that the pressure sensor 180 may include a protective cover to prevent the delivery device (not explicitly shown) from damaging the sensor 180 during delivery of the ocular implant 100, although this is not required.

MEMS pressure sensors are often formed by anisotropically etching a recess into a back side of a silicon substrate die, leaving a thin flexible diaphragm 182. In operation, at least one surface of the diaphragm 182 is exposed to an input pressure (e.g., the ocular pressure). The diaphragm 182 deflects according to the magnitude of the input pressure, which may be detected by one or more electrical components or sense elements 186 (e.g., piezoresistors) positioned on or embedded within the diaphragm 182. The change in resistance of the piezoresistors 186 is reflected as a change in an output voltage signal from a resistive bridge formed at least in part by the piezoresistors. In some cases, the diaphragm may be made thinner with the addition of support bosses, which may help increase the sensitivity of the diaphragm over a flat plate diaphragm. Circuit elements may be connected so that sensor elements 186 to provide some level of signal processing before providing an output signal to bond pads 188 of the pressure sensor 180. The signal processing may filter, amplify, linearize, calibrate and/or otherwise process the raw sensor signal produced by the sensor elements (e.g., piezoresistors 186). While the sense elements 186 have been described as piezoresistors, it is contemplated that the sense elements may be selected to provide a capacitive pressure sensor 180.

Figure 10B:
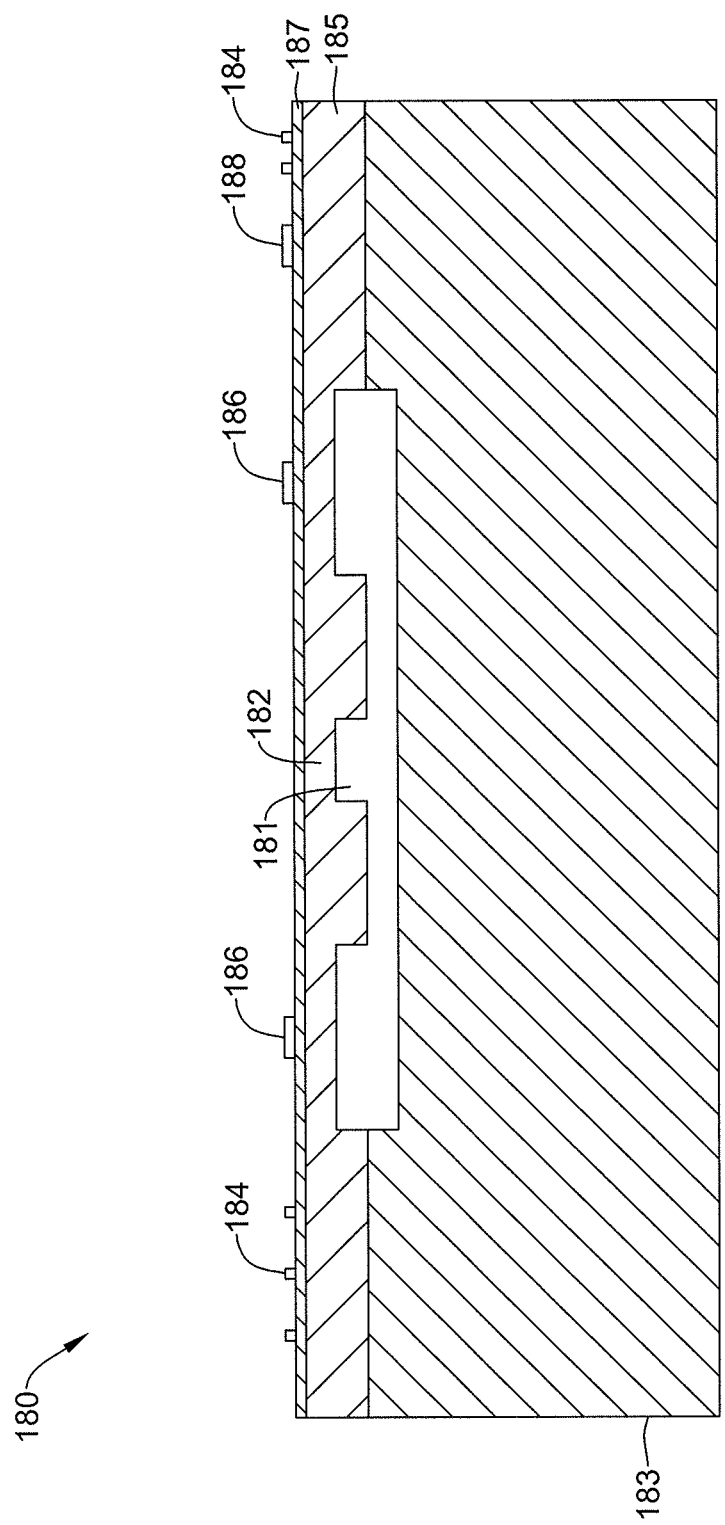
FIG. 10B is a cross-sectional view of the illustrative pressure sensor of FIG. 10A, taken at line B-B.
Figure 10C:
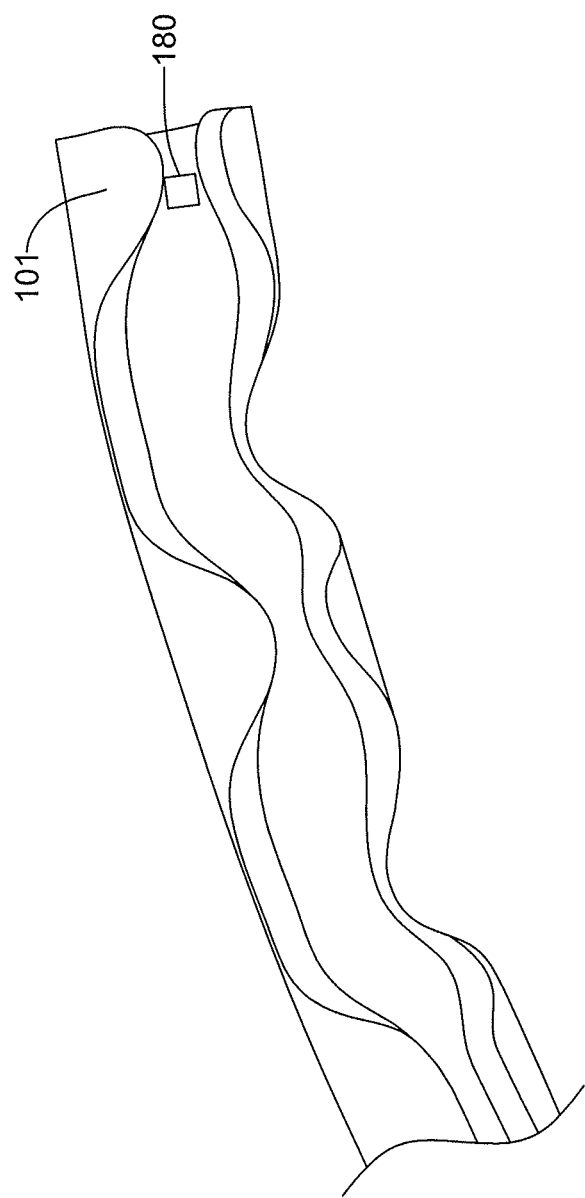
FIG. 10C is an enlarged perspective view of another portion of the ocular implant including a pressure sensor.

The pressure sensor 180 may include a first substrate 185 and a second substrate 183, as shown in FIG. 10B, which is a cross-section of the illustrative pressure sensor 180 taken at line B-B in FIG. 10A. In some instances, the first substrate 185 may be a layered silicon-insulator-silicon substrate or wafer formed with silicon on insulator (SOI) technology, although this is not required. It is contemplated that other substrates may be used, as desired. The first substrate 185 may include a first silicon layer. An insulating, or oxide, layer 187 may be disposed on the first silicon layer 185. In some instances, the insulating layer 187 may be formed from silicon dioxide, silicon nitride, sapphire, and/or any other suitable insulating material. While not explicitly shown, the pressure sensor 180 may include a second silicon layer disposed on the insulating layer. In some instances, the second silicon layer may be thinned or removed such that the oxide layer 187 is exposed at the side facing away from the second substrate 183. Alternatively, and in some cases, the second silicon layer and oxide layer 187 are not provided from the start.

The second substrate 183 may be any semi-conductor wafer (e.g., silicon or germanium) or other substrate as desired. It is contemplated that either or both the first substrate 185 or the second substrate 183 may be doped with an impurity to provide an n-type or p-type extrinsic semiconductor. For example, the first substrate 185 may be an n-type substrate while the second substrate 183 may be a p-type substrate. The reverse configuration is also contemplated, or both substrates may be doped the same polarity. In some instances, the first substrate 185 and/or the second substrate 183 may include an epitaxial layer.

A portion of the first substrate 185, such as a portion of the first silicon layer, may be removed, leaving a thin, flexible diaphragm 182 over a cavity or recess 181. In some cases, piezoresistors 186 may be located in or on the diaphragm 182 to measure deflection/stress of the diaphragm 182 to form a pressure sensor. During operation, at least one surface of the diaphragm 182 may be exposed to an input pressure. The diaphragm 182 may then deflect according to a magnitude of the pressure on the diaphragm 182. A deflection of the diaphragm 182 then creates changes in resistance in the piezoresistors 186. A change in resistance of the piezoresistors 186 may be reflected as a change in an output voltage signal of a resistive bridge that is formed at least partially by the piezoresistors 186. The output voltage provides a measure of the input pressure exerted on the diaphragm 182.

It is contemplated that the second substrate 183 may be flexible to allow the substrate 183 to be mounted flush against the inner surface 128 of the ocular implant 100. Alternatively, or additionally, the second substrate 183 may have a curved outer surface (facing away from the diaphragm 182) shaped to generally correspond to the curved inner surface 128 of the ocular implant 100. It is further contemplated that the materials forming the pressure sensor 180 may be selected such that the pressure sensor 180 is biocompatible.

As noted above, while the pressure sensor 180 has been described as a MEMS pressure sensor, it is contemplated that pressure sensor 180 may take other suitable forms. In one alternative example, the pressure sensor may be formed in such a way that radio waves can be used to detect changes in pressure without sensor elements incorporated into the device. Such a pressure sensor may include a flexible base substrate, a bottom inductive coil positioned on the base substrate, a layer of pressure sensitive rubber pyramids positioned over the bottom inductive coil, a top inductive coil positioned on top of the rubber pyramids, and a top substrate positioned over the top inductive coil. As a pressure is exerted on the sensor, the inductive coils move close together. Radio waves (from an applied source) reflected by the inductive coils have a lower resonance frequency when the coils are positioned closer together. Thus, the frequency of the radio waves can indicate the distance between the coils which is then correlated to the pressure exerted on the device.

Figure 11:
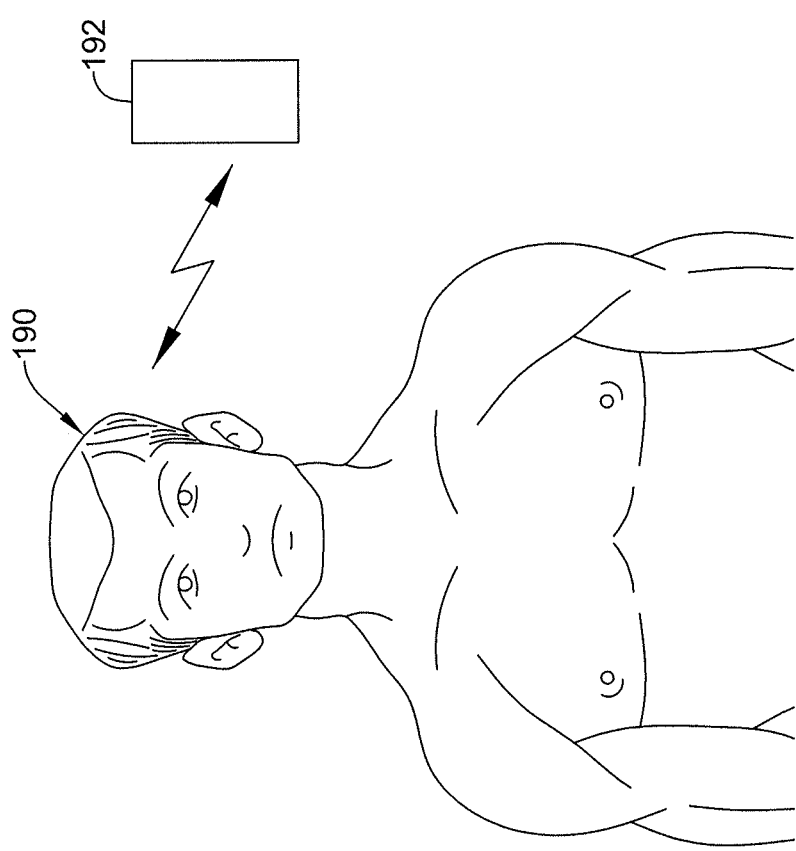
FIG. 11 is stylized view of an electronic device receiving data from an implanted ocular implant.

The pressure sensor 180 may be further provided with an antenna or inductor 184 to allow the data from the pressure sensor 180 to be wirelessly communicated to a readout device. In some instances, the pressure sensor 180 may use radiofrequency communication protocols, such as, but not limited to cellular communication, ZigBee®, Bluetooth®, WiFi®, IrDA, dedicated short range communication (DSRC), EnOcean®, or any other suitable wireless protocols, as desired to transmit the data from the pressure sensor 180 to another device located outside the body. The data may be transmitted to any number so suitably enabled devices, including, but not limited to, cellular phones, tablet or laptop computers, desktop computers, portable handheld devices, such a personal digital assistant (PDA), or a specially designed device, such as, but not limited to a medical device. This may allow a physician, patient, or other interested party to monitor the ocular pressure without the use of a tonometer. In some instances, the pressure data may be automatically transmitted to a physician from the remote device. For example, as shown in FIG. 11, once the ocular implant 100 with the pressure sensor 180 has been implanted, an enabled remote device 192 may be brought within communication range of the patient's 190 eye. This may allow the enabled device 192 to receive the ocular pressure data recorded at the pressure sensor 180. The enabled device 192 may be configured to automatically transmit the data to a physician, for example, to a second remote device.

Figure 12:
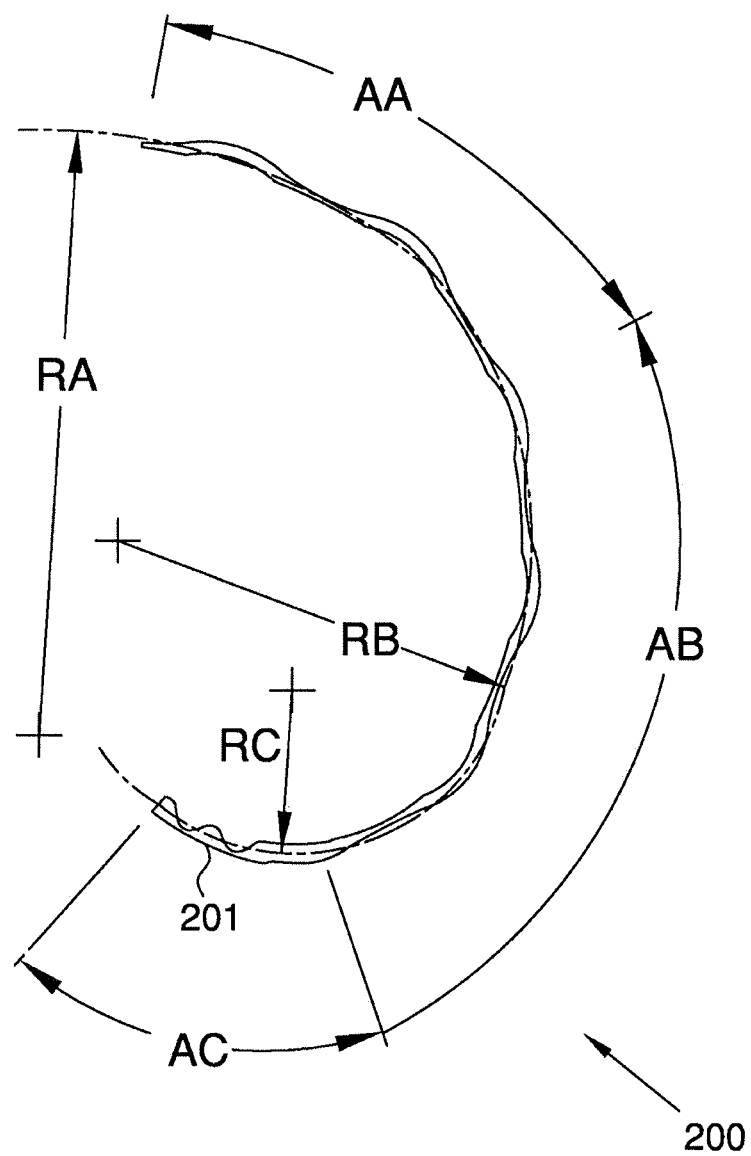
FIG. 12 is a plan view showing an ocular implant according to another embodiment of the invention having a longitudinal radius of curvature that varies along its length.

FIG. 12 is a plan view showing an ocular implant 200 having a radius of curvature that varies along its length. A proximal end 201 of the ocular implant 200 may include an interlocking portion configured to mate with and/or engage a complementary interlocking portion of a delivery tool. In the embodiment of FIG. 12, ocular implant 200 has an at rest shape that is generally curved. This at rest shape can be established, for example, using a heat-setting process. The ocular implant shape shown in FIG. 12 includes a distal radius RA, a proximal radius RC, and an intermediate radius RB. In the embodiment of FIG. 12, distal radius RA is larger than both intermediate radius RB and proximal radius RC. Also in the embodiment of FIG. 12, intermediate radius RB is larger than proximal radius RC and smaller than distal radius RA. In one useful embodiment, distal radius RA is about 0.320 inches (8.128 millimeters), intermediate radius RB is about 0.225 inches (5.715 millimeters) and proximal radius RC is about 0.205 inches (5.207 millimeters).

In the embodiment of FIG. 12, a distal portion of the ocular implant follows an arc extending across an angle AA. A proximal portion of the ocular implant follows an arc extending across an angle AC. An intermediate portion of the ocular implant is disposed between the proximal portion and the distal portion. The intermediate portion extends across an angle AB. In one useful embodiment, angle AA is about 55 degrees, angle AB is about 79 degrees and angle AC is about 60 degrees.

Ocular implant 200 may be used in conjunction with a method of treating the eye of a human patient for a disease and/or disorder (e.g., glaucoma). Some such methods may include the step of inserting a core member into a lumen defined by ocular implant 200. The core member may comprise, for example, a wire or tube. The distal end of the ocular implant may be inserted into Schlemm's canal. The ocular implant and the core member may then be advanced into Schlemm's canal until the ocular implant has reached a desired position. In some embodiments, an inlet portion of the implant may be disposed in the anterior chamber of eye while the remainder of the implant extends through the trabecular mesh into Schlemm's canal. The core member may then be withdrawn from the ocular implant, leaving the implant in place to support tissue forming Schlemm's canal. Further details of ocular implant delivery systems may be found in U.S. application Ser. No. 11/943,289, filed Nov. 20, 2007, now U.S. Pat. No. 8,512,404, the disclosure of which is incorporated herein by reference.

The flexibility and bending modulus features of the ocular implant of this invention help ensure proper orientation of the implant within Schlemm's canal. FIG. 1 shows the desired orientation of opening 124 when the implant 100 is disposed in Schlemm's canal. As shown, opening 124 faces radially outward. The implant 100 is therefore designed so that it is maximally flexible when bent along a plane defined by the longitudinal axis of implant 100 as shown in FIG. 1, and less flexible when bent in other planes, thereby enabling the curved shape of Schlemm's canal to help place the implant in this orientation automatically if the implant is initially placed in Schlemm's canal in a different orientation.

FIG. 13 is a perspective view showing an ocular implant 300 in accordance with an additional embodiment in accordance with the present detailed description. With reference to FIG. 13, it will be appreciated that ocular implant 300 has a resting (i.e., unstressed) shape that is generally straight. Ocular implant 300 extends along a longitudinal axis 334 that is generally straight. In some useful embodiments, ocular implant 300 is sufficiently flexible to assume a curved shape when advanced into Schlemm's canal of an eye.

Ocular implant 300 comprises a body 302. With reference to FIG. 13, it will be appreciated that body 302 comprises a plurality of tissue supporting frames 304 and a plurality of spines 306. As shown in FIG. 13, these spines 306 and frames 304 are arranged in an alternating pattern in which one spine extends between each adjacent pair of frames 304. The frames 304 of body 302 include a first frame 336 of ocular implant 300 is disposed between a first spine 340 and a second spine 342. In the embodiment of FIG. 13, first frame 336 comprises a first strut 344 that extends between first spine 340 and second spine 342. A second strut 346 of first frame also extends between first spine 340 and second spine 342. Each strut undulates in a circumferential direction as it extends longitudinally between first spine 340 and second spine 342.

An inner surface 328 of body 302 defines a channel 326. Body 302 of ocular implant 300 includes a first edge 320 and a second edge 322 that define a first opening 324. Channel 326 of ocular implant 300 fluidly communicates with first opening 324. First strut 344 of first frame 336 comprises a first edge 325A. Second strut 346 has a first edge 325B. In FIG. 13, first opening 324 in body 302 can be seen extending between first edge 325A of first strut 344 and a first edge 325B of second strut 346.

A first axis 356, a second axis 358 and a third axis 360 are shown in FIG. 13. Second axis 358 is generally perpendicular to first axis 356. Third axis 360 is generally skewed relative to first axis 356. The flexibility of body 302 is at a maximum when body 302 is bent by a moment acting about first axis 356, and body 302 has less flexibility when bent by a moment acting about an axis other than first axis 356 (e.g., second axis 358 and third axis 360). Stated another way, in the embodiment of FIG. 13, the bending modulus of body 302 is at a minimum when body 302 is bent by a moment acting about first axis 356, and body 302 has a greater bending modulus when bent by a moment acting about an axis other than first axis 356 (e.g., second axis 358 and third axis 360).

The ocular implant 300 may further include an intraocular pressure sensor 380 mounted to the inner surface 328 of the ocular implant 300. The pressure sensor 380 may be similar in form and function to pressure sensor 180 described above. While the pressure sensor 380 is illustrated as mounted to an inner surface 328 of the ocular implant 300 it is contemplated that the pressure sensor 380 may be mounted within one of the openings 324 or on an outer surface of the ocular implant 300, as desired. The pressure sensor 380 may continuously measure the intraocular pressure of a patient, once the ocular implant 300 has been implanted.

The pressure sensor 380 may be a Micro-Electro-Mechanical System (MEMS) pressure sensor. While the pressure sensor 380 has been described as a MEMS pressure sensor, it is contemplated that other pressure sensors may be used in place of, or in addition to, a MEMS pressure sensor. MEMS pressure sensors are often formed by anisotropically etching a recess into a back side of a silicon substrate die, leaving a thin flexible diaphragm. In operation, at least one surface of the diaphragm is exposed to an input pressure (e.g., the ocular pressure). The diaphragm deflects according to the magnitude of the input pressure, which may be detected by one or more electrical components or sense elements (e.g., piezoresistors) positioned on or embedded within the diaphragm. The change in resistance of the piezoresistors is reflected as a change in an output voltage signal from a resistive bridge formed at least in part by the piezoresistors. In some cases, the diaphragm may be made thinner with the addition of support bosses, which may help increase the sensitivity of the diaphragm over a flat plate diaphragm. Circuit elements may be connected so that sensor elements to provide some level of signal processing before providing an output signal to bond pads of the pressure sensor. The signal processing may filter, amplify, linearize, calibrate and/or otherwise process the raw sensor signal produced by the sensor elements (e.g., piezoresistors). While the sense elements have been described as piezoresistors, it is contemplated that the sense elements may be selected to provide a capacitive pressure sensor 380.

The pressure sensor 380 may be further provided with an antenna or inductor to allow the data from the pressure sensor 380 to be wirelessly communicated to a readout device. In some instances, the pressure sensor 380 may use radiofrequency communication protocols, such as, but not limited to cellular communication, ZigBee®, Bluetooth®, WiFi®, IrDA, dedicated short range communication (DSRC), EnOcean®, or any other suitable wireless protocols, as desired to transmit the data from the pressure sensor 380 to another device located outside the body. The data may be transmitted to any number so suitably enabled devices, including, but not limited to, cellular phones, tablet computers, computers, portable handheld devices, such a personal digital assistant (PDA), or a specially designed device. This may allow a physician, patient, or other interested party to monitor the ocular pressure without the use of a tonometer.

Figure 14:
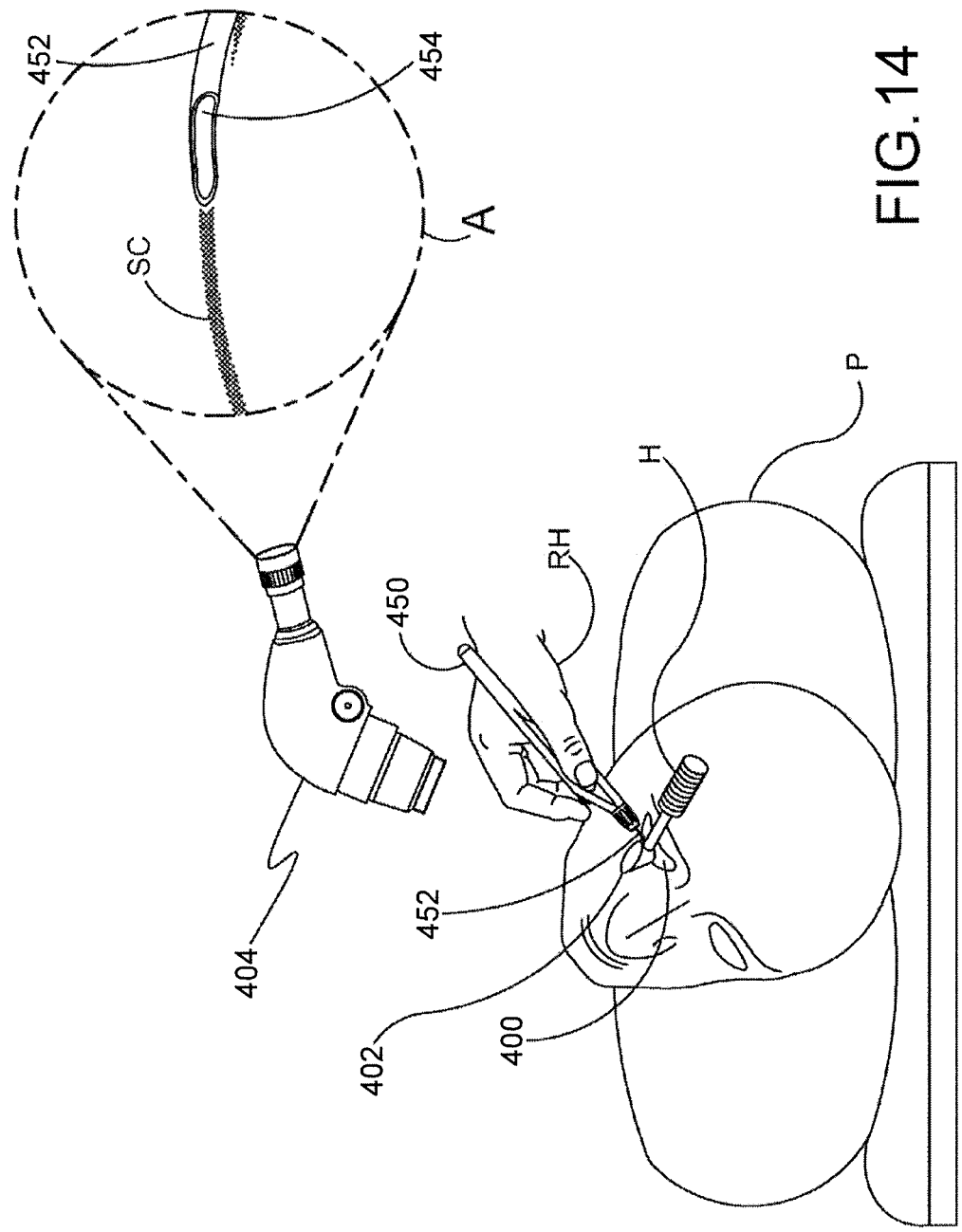
FIG. 14 is a stylized representation of a medical procedure in accordance with this Detailed Description.

FIG. 14 is a stylized representation of a medical procedure in accordance with this detailed description. In the procedure of FIG. 14, a physician is treating an eye 400 of a patient P. In the procedure of FIG. 14, the physician is holding a hand piece of a delivery system 450 in his or her right hand RH. The physician's left hand (not shown) may be used to hold the handle H of a gonio lens 402. Alternatively, some physicians may prefer holding the delivery system hand piece in the left hand and the gonio lens handle H in the right hand RH.

During the procedure illustrated in FIG. 14, the physician may view the interior of the anterior chamber using gonio lens 402 and a microscope 404. Detail A of FIG. 14 is a stylized simulation of the image viewed by the physician. A distal portion of a cannula 452 is visible in Detail A. A shadow-like line indicates the location of Schlemm's canal SC which is lying under various tissues (e.g., the trabecular meshwork) that surround the anterior chamber. A distal opening 454 of cannula 452 is positioned near Schlemm's canal SC of eye 400.

Methods in accordance with this detailed description may include the step of advancing the distal end of cannula 452 through the cornea of eye 400 so that a distal portion of cannula 452 is disposed in the anterior chamber of the eye. Cannula 452 may then be used to access Schlemm's canal of the eye, for example, by piercing the wall of Schlemm's canal with the distal end of cannula 452. Distal opening 454 of cannula 452 may be placed in fluid communication with a lumen defined by Schlemm's canal. The ocular implant may be advanced out of distal opening 454 and into Schlemm's canal. Insertion of the ocular implant into Schlemm's canal may facilitate the flow of aqueous humor out of the anterior chamber of the eye.

Figure 15:
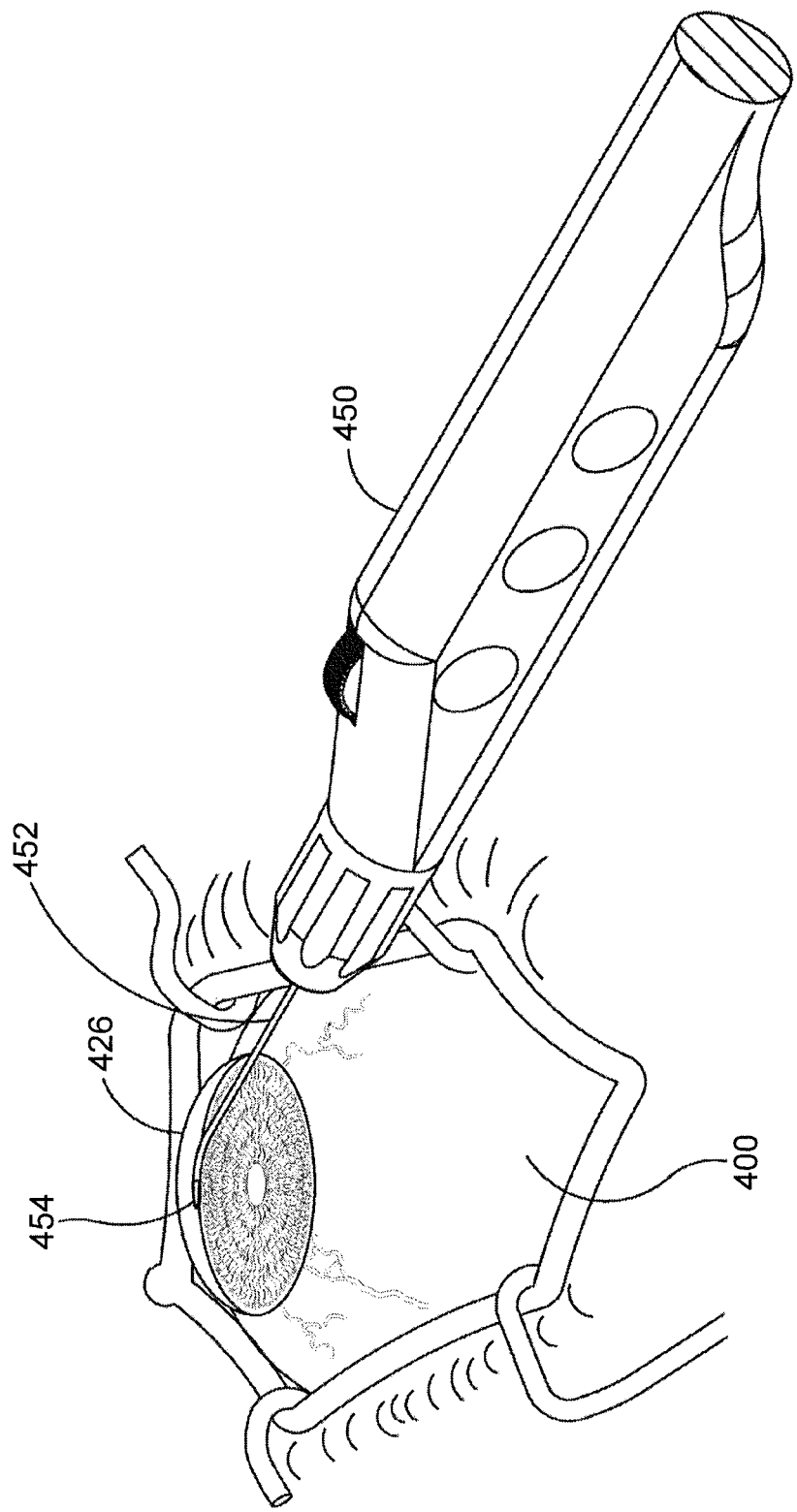
FIG. 15 is an enlarged perspective view further illustrating the delivery system and the eye shown in FIG. 14.

FIG. 15 is an enlarged perspective view further illustrating delivery system 450 and eye 400 shown in the previous figure. In FIG. 15, cannula 452 of delivery system 450 is shown extending through a cornea 426 of eye 400. A distal portion of cannula 452 is disposed inside the anterior chamber defined by cornea 426 of eye 400. In the embodiment of FIG. 15, cannula 452 is configured so that a distal opening 454 of cannula 452 can be placed in fluid communication with Schlemm's canal.

In the embodiment of FIG. 15, an ocular implant is disposed in a passageway defined by cannula 452. Delivery system 450 includes a mechanism that is capable of advancing and retracting the ocular implant along the length of cannula 452. The ocular implant may be placed in Schlemm's canal of eye 400 by advancing the ocular implant through the distal opening of cannula 452 while the distal opening is in fluid communication with Schlemm's canal.

FIG. 16A is a perspective view showing a delivery system 500 including an ocular implant 550 and a cannula 508 defining a passageway that is dimensioned to slidingly receive ocular implant 550. Delivery system 500 may be used to advance ocular implant 550 into a target location in the eye of a patient. Examples of target locations that may be suitable in some applications include areas in and around Schlemm's canal, the trabecular meshwork, the suprachoroidal space, and the anterior chamber of the eye. FIG. 16B is an enlarged detail view further illustrating ocular implant 550 and cannula 508 of delivery system 500.

Delivery system 500 of FIG. 16A is capable of controlling the advancement and retraction of ocular implant 550 within cannula 508. Ocular implant 550 may be placed in a target location (e.g., Schlemm's canal) by advancing the ocular implant through a distal opening 532 of cannula 508 while the distal opening is in fluid communication with Schlemm's canal. In the embodiment of FIG. 16A, ocular implant 550 has been advanced through distal opening 532 of cannula 508 for purposes of illustration.

Delivery system 500 of FIG. 16A includes a housing 502, a sleeve 504, and an end cap 510. A tracking wheel 506 extends through a wall of housing 502 in FIG. 16A. Tracking wheel 506 is part of a mechanism that is capable of advancing and retracting a delivery tool 552 of delivery system 500. The delivery tool 552 extends through a distal opening of cannula 508 of FIG. 16B. Rotating the tracking wheel will cause delivery tool 552 to move in an axial direction along a passageway defined by cannula 508. The axial direction may be in a distal direction D or a proximal direction P. The delivery tool 552 and the mechanism for moving the delivery tool 552 are described in commonly assigned application Ser. No. 62/024,295, which is herein incorporated by reference.

In the embodiment of FIG. 16A, housing 502 is configured to be gripped with one hand while providing control over the axial advancement and retraction of ocular implant via tracking wheel 506. The housing of delivery system 500 results in an advantageous ergonomic relationship of the fingers relative to the hand. This design provides a configuration that will allow a user, such as a physician, to stabilize the device using part of the hand, while leaving the middle or index finger free move independently from the remainder of the hand. The middle or index finger is free to move independently to rotate the wheel for advancing and/or retract the ocular implant.

FIG. 16B is an enlarged detail view further illustrating ocular implant 550 and a cannula 508 of delivery system 500. Cannula 508 comprises a generally tubular member 598 having proximal portion 540, a distal end 534, and a distal portion 544 extending between distal end 534 and proximal portion 540. In the embodiment of FIG. 6, distal portion 544 is curved. In some useful embodiments, distal portion 544 is dimensioned and configured to be received in the anterior chamber of the eye.

Figure 16:
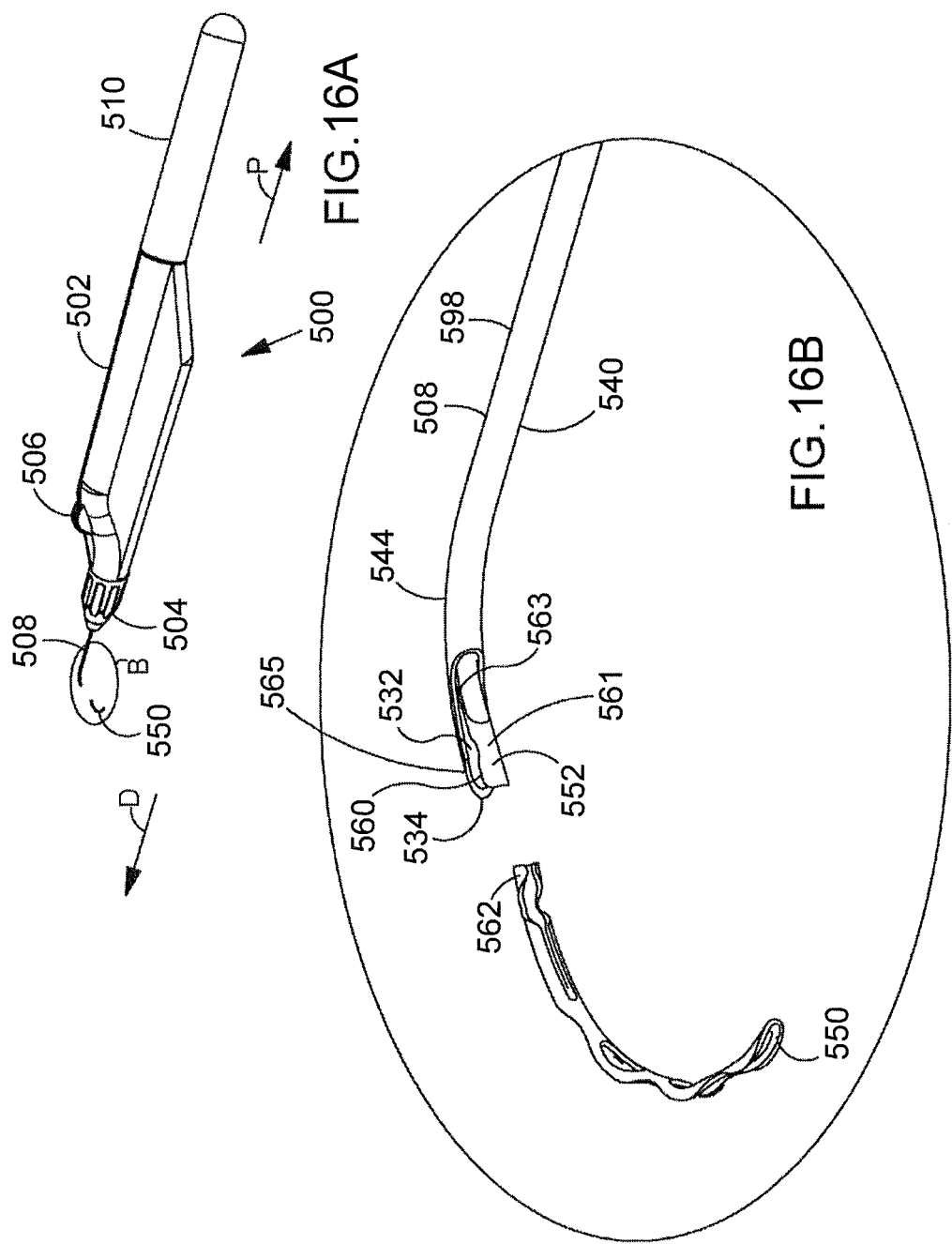
FIG. 16A is a perspective view showing a delivery system including an ocular implant and a cannula defining a passageway that is dimensioned to slidingly receive the ocular implant.
FIG. 16B is an enlarged detail view further illustrating the ocular implant and the cannula 108 shown in FIG. 6A.

FIG. 16B shows delivery tool 552 of delivery system 500 extending through distal opening 532 of cannula 508. Delivery tool 552 includes an interlocking portion 560 that is configured to form a connection with a complementary interlocking portion 562 of ocular implant 550, as explained in more detail below. In the embodiment of FIG. 16, rotating the tracking wheel will cause delivery tool 552 and ocular implant 550 to move along a path defined by cannula 508. Cannula 508 is sized and configured so that the distal end of cannula 508 can be advanced through the trabecular meshwork of the eye and into Schlemm's canal. Positioning cannula 508 in this way places distal opening 532 in fluid communication with Schlemm's canal. Ocular implant 550 may be placed in Schlemm's canal by advancing the ocular implant through distal opening 532 of cannula 508 while the distal opening is in fluid communication with Schlemm's canal. The distal portion of the cannula may include a cutting portion configured to cut through the trabecular meshwork and the wall of Schlemm's canal, such as by providing distal end 534 with a sharp edge adapted to cut through such tissue.

Figure 17:
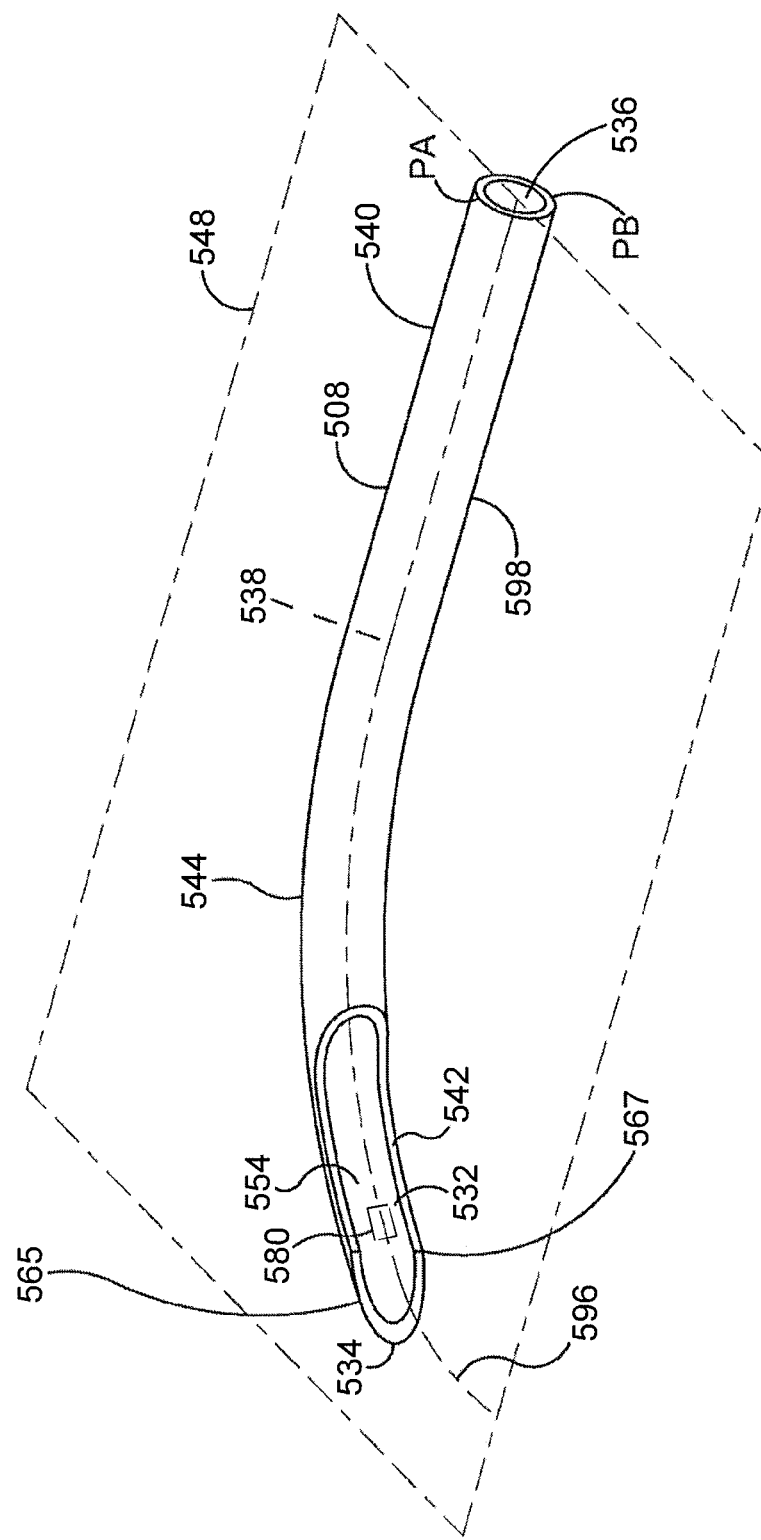
FIG. 17 is a perspective view of a cannula in accordance with the detailed description.

FIG. 17 is a perspective view of a cannula 508 in accordance with the present detailed description. Cannula 508 of FIG. 17 comprises a generally tubular member 598 having a central axis 596. Generally tubular member 598 of FIG. 17 comprises a proximal portion 540, a distal end 534, and a distal portion 544 extending between distal end 534 and proximal portion 540. A distal opening surface 542 surrounds a distal opening 532 extending through the distal end 534 and through a side wall of cannula 508. A beveled edge 565 is disposed at the distal end of distal opening surface 542, extending from the distal end 534 to a proximal extent 567 of beveled edge 565. Tubular member 598 defines distal opening 532, a proximal opening 536, and a passageway 538 extending between proximal opening 536 and distal opening 532.

In the embodiment of FIG. 17, proximal portion 540 of cannula 508 is substantially straight, distal portion 544 of cannula 508 is curved, and central axis 596 defines a curvature plane 548. Curvature plane 548 may be referred to as a plane of curvature. Curvature plane 548 divides cannula 508 into a first portion PA and a second portion PB. In the embodiment of FIG. 17, second portion PB is substantially a mirror image of first portion PA. In FIG. 17, distal portion 544 is shown extending between distal end 534 and proximal portion 540 with no intervening elements. In the embodiment of FIG. 17, distal portion 544 is curved along its entire length.

A method in accordance with this detailed description may include the step of advancing the distal end 534 of cannula 508 through the cornea of a human eye so that distal end 534 is disposed in the anterior chamber of the eye. Cannula 508 may then be used to access Schlemm's canal of the eye, for example, by piercing the wall of Schlemm's canal with the distal end 534 of cannula 508. The beveled edge 565 may be inserted into Schlemm's canal to place at least part of distal opening 532 of cannula 508 in communication with Schlemm's canal, as discussed in more detail below. The ocular implant may be advanced out of a distal port of the cannula and into Schlemm's canal.

In the embodiment of FIG. 17, distal portion 544 of cannula 508 defines a trough 554. In some useful embodiments, trough 554 is configured to receive the entire external cross section of an ocular implant as the ocular implant is being advanced into Schlemm's canal. When this is the case, trough 554 may have a depth dimension that is deeper than a width of the ocular implant. This cannula configuration advantageously prevents the ocular implant from intersecting the layers of the trabecular meshwork as the ocular implant is advanced into Schlemm's canal. Trough 554 may also be configured to allow the proximal portion of the ocular implant to be released from the delivery tool, as discussed below.

The cannula 508 may further include a pressure sensor 580 disposed within the trough 554. The pressure sensor 580 may be similar in form and function to pressure sensor 180 described above. While the pressure sensor 580 is illustrated as mounted within the trough 554 of the cannula, it is contemplated that the pressure sensor 580 may be mounted at other locations within or on the cannula 508. The pressure sensor 580 may provide an instantaneous pressure reading during implantation of the ocular implant 550 or shortly thereafter. In some instances, the pressure reading obtained from the pressure sensor 580 on the cannula 508 can be compared to a pressure reading obtained from a pressure sensor mounted on the ocular implant 550, if so provided.

The pressure sensor 580 may be a Micro-Electro-Mechanical System (MEMS) pressure sensor. While the pressure sensor 580 has been described as a MEMS pressure sensor, it is contemplated that other pressure sensors may be used in place of, or in addition to, a MEMS pressure sensor. Further, while only a single pressure sensor 580 has been illustrated, the cannula 508 may include more than one pressure sensor 580, as desired. MEMS pressure sensors are often formed by anisotropically etching a recess into a back side of a silicon substrate die, leaving a thin flexible diaphragm. In operation, at least one surface of the diaphragm is exposed to an input pressure (e.g., the ocular pressure). The diaphragm deflects according to the magnitude of the input pressure, which may be detected by one or more electrical components or sense elements (e.g., piezoresistors) positioned on or embedded within the diaphragm. The change in resistance of the piezoresistors is reflected as a change in an output voltage signal from a resistive bridge formed at least in part by the piezoresistors. In some cases, the diaphragm may be made thinner with the addition of support bosses, which may help increase the sensitivity of the diaphragm over a flat plate diaphragm. Circuit elements may be connected so that sensor elements to provide some level of signal processing before providing an output signal to bond pads of the pressure sensor. The signal processing may filter, amplify, linearize, calibrate and/or otherwise process the raw sensor signal produced by the sensor elements (e.g., piezoresistors). While the sense elements have been described as piezoresistors, it is contemplated that the sense elements may be selected to provide a capacitive pressure sensor 580.

The pressure sensor 580 may be further provided with an antenna or inductor to allow the data from the pressure sensor 580 to be wirelessly communicated to a readout device. In some instances, the pressure sensor 580 may use radiofrequency communication protocols, such as, but not limited to cellular communication, ZigBee®, Bluetooth®, WiFi®, IrDA, dedicated short range communication (DSRC), EnOcean®, or any other suitable wireless protocols, as desired to transmit the data from the pressure sensor 580 to another device located outside the body. The data may be transmitted to any number so suitably enabled devices, including, but not limited to, cellular phones, tablet computers, computers, portable handheld devices, such a personal digital assistant (PDA), or a specially designed device. This may allow a physician, patient, or other interested party to monitor the ocular pressure without the use of a tonometer.

Figure 18:
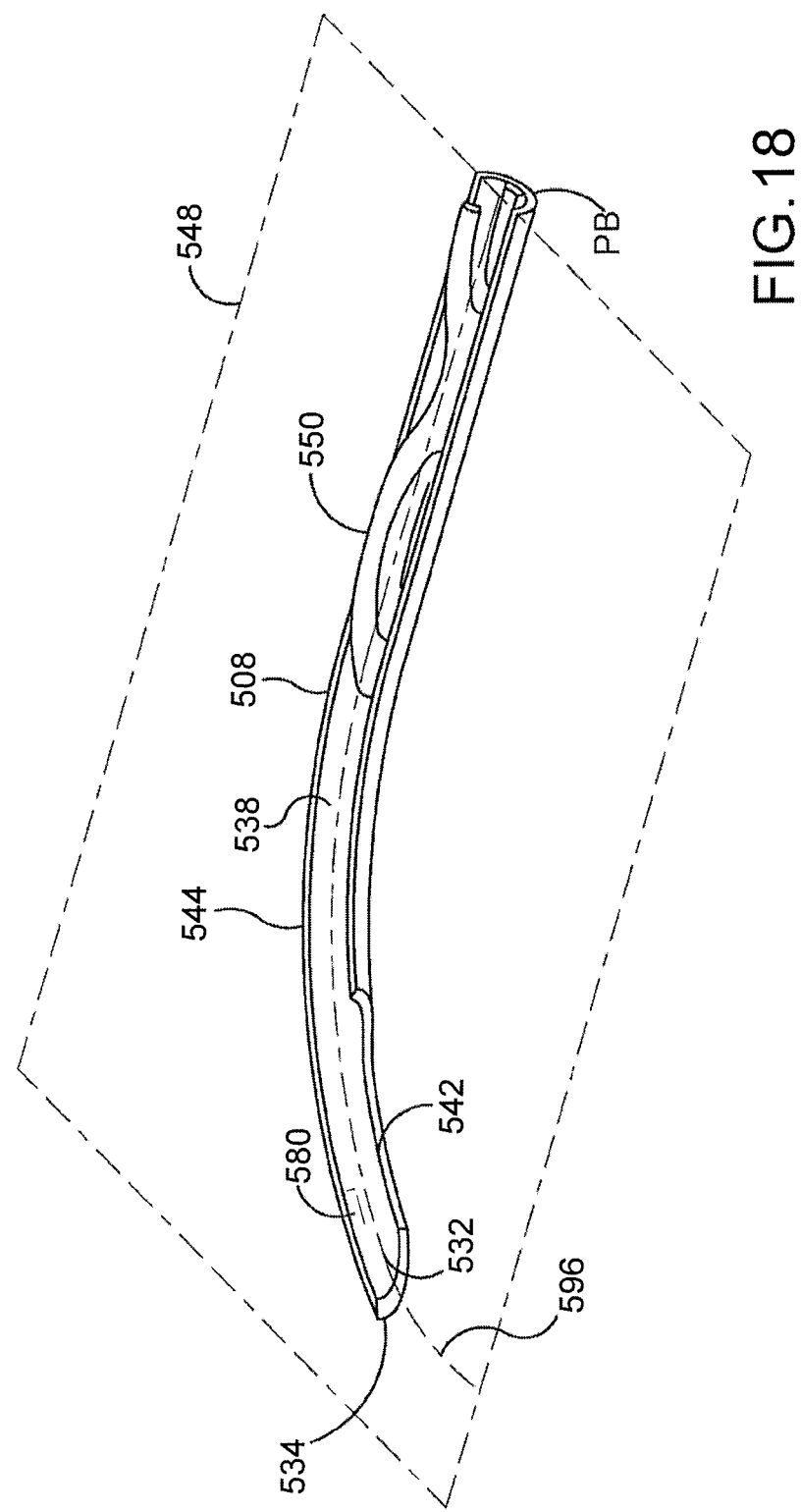
FIG. 18 is a perspective view of an assembly including the cannula shown in FIG. 17 and an ocular implant that is resting in a passageway defined by the cannula.
Figure 23:
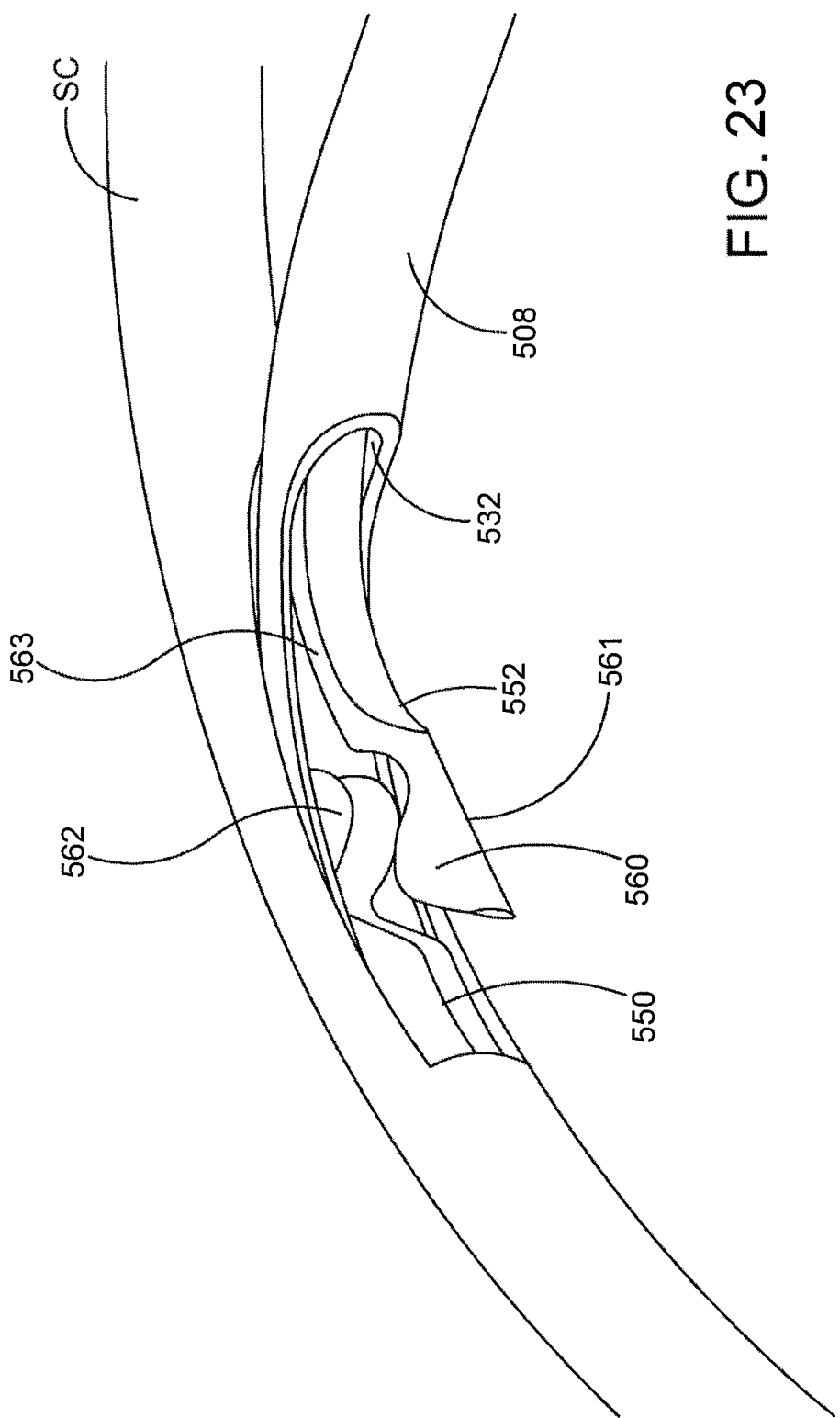
FIG. 23 is an additional perspective view showing the ocular implant and the cannula shown in FIGS. 21 and 22.

FIG. 18 is a perspective view of an assembly including cannula 508 shown in the previous figure. For purposes of illustration, cannula 508 is cross-sectionally illustrated in FIG. 23. In FIG. 18, an ocular implant 550 can be seen resting in a passageway 538 defined by cannula 508. With reference to FIG. 18, it will be appreciated that distal portion 544 of cannula 508 is curved so that central axis 596 of cannula 508 defines a curvature plane 548. With reference to FIG. 23, it will be appreciated that curvature plane 548 divides cannula 508 into a first portion and a second portion PB. Only second portion PB of cannula 508 is shown in the illustrative embodiment of FIG. 18.

Figure 19:
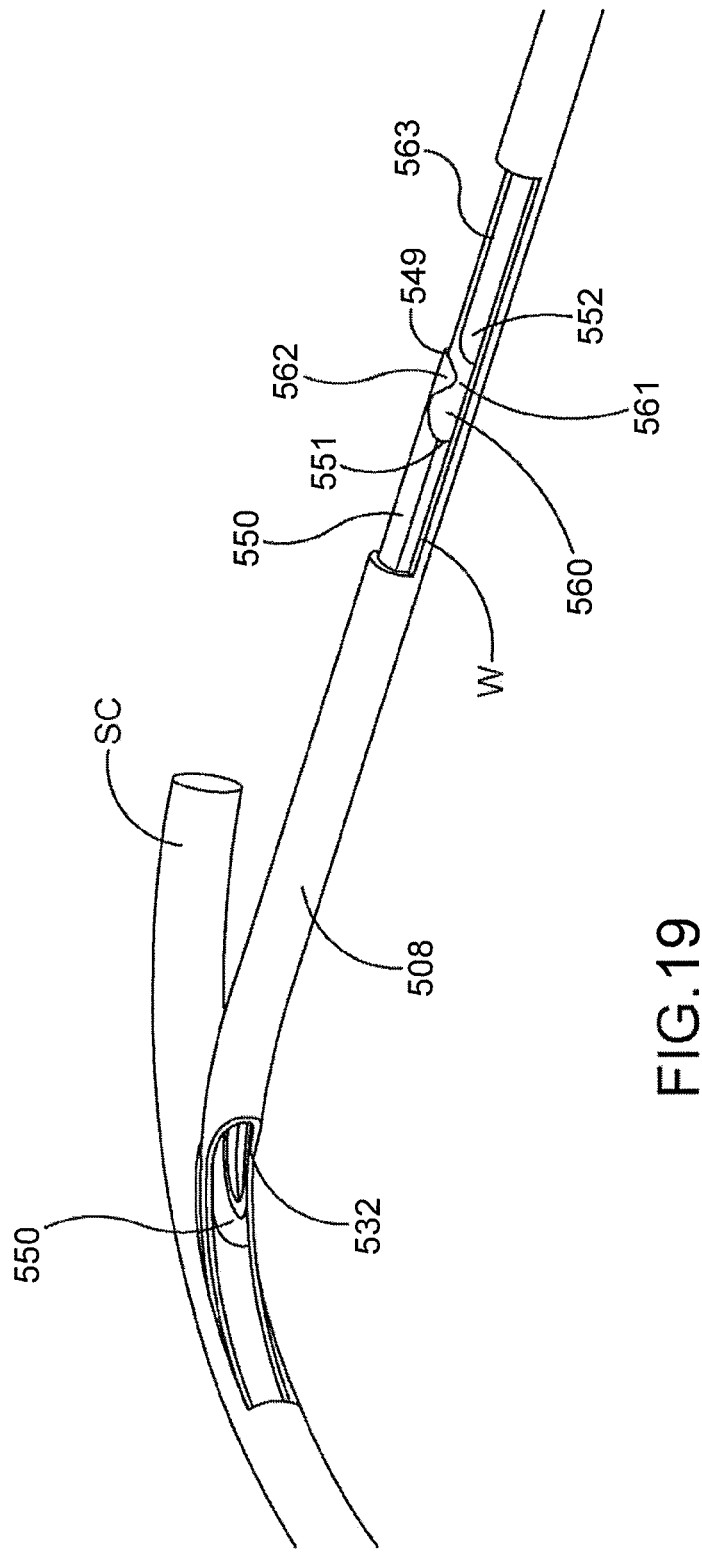
FIG. 19 is a stylized perspective view including the assembly shown in FIG. 18.

FIG. 19 is a stylized perspective view including the assembly shown in the previous figure. In the embodiment of FIG. 19, a distal portion of cannula 508 is shown extending through the wall of Schlemm's canal SC. The distal tip of cannula 508 may include a sharp portion configured for cutting and/or piercing the trabecular meshwork and the wall of Schlemm's canal so that the passageway defined by the cannula can be placed in fluid communication with the lumen defined by Schlemm's canal. With the passageway of the cannula placed in fluid communication with the lumen of Schlemm's canal, ocular implant 550 can be advanced out of the distal opening of the cannula and into Schlemm's canal. In FIG. 19, a distal portion of ocular implant 550 can be seen through distal opening 532 of cannula 508.

For purposes of illustration, a hypothetical window W is cut through the wall of cannula 508 in FIG. 19. An interlocking portion 560 of a delivery tool 552 and a complementary interlocking portion 562 of ocular implant 550 are visible through window W. In the embodiment of FIG. 19, interlocking portion 560 of delivery tool 552 and complementary interlocking portion 562 of ocular implant 550 are engaging each other so that a proximal end 549 of ocular implant 550 is proximal to the distal end 551 of delivery tool 552. Surface 561 of delivery tool 552 rests against the wall of cannula 508 to prevent interlocking portion 560 of delivery tool 552 and complementary interlocking portion 562 of ocular implant 550 from disengaging one another. When they are connected in this fashion, delivery tool 552 and ocular implant 550 move together as the delivery tool is advanced and retracted relative to cannula 508 by the delivery system mechanism.

Figure 20:
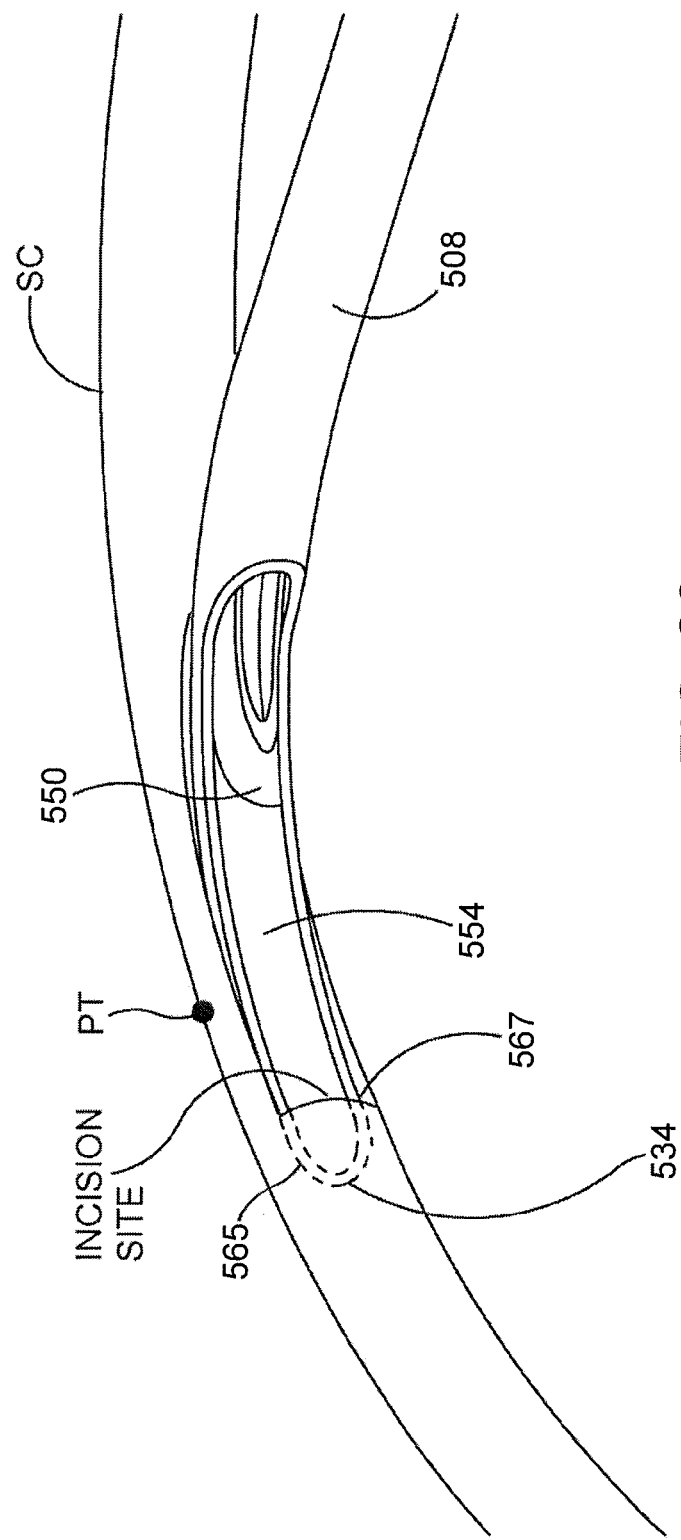
FIG. 20 is an enlarged perspective view showing a portion of the cannula shown in the assembly of FIG. 19.

FIG. 20 is an enlarged perspective view showing a portion of cannula 508 shown in the previous figure. In some useful embodiments, cannula 508 is curved to achieve substantially tangential entry into Schlemm's canal SC. In the embodiment of FIG. 20, cannula 508 is contacting an outer major wall of Schlemm's canal SC at a point of tangency PT. Also in the embodiment of FIG. 20, a curved distal portion of cannula 508 is dimensioned to be disposed within the anterior chamber of the eye.

As shown in FIG. 20, the distal tip 534 and beveled edge of the cannula 508 have been inserted into Schlemm's canal up to the proximal extent 567 of beveled edge 565. In this position, ocular implant 550 can be seen extending into trough 554. In some useful embodiments, the ocular implant has a radius of curvature that is larger than the radius of curvature of the cannula. This arrangement ensures that the ocular implant will track along trough 554 as the ocular implant is urged in a distal direction by delivery system 500.

Figure 21:
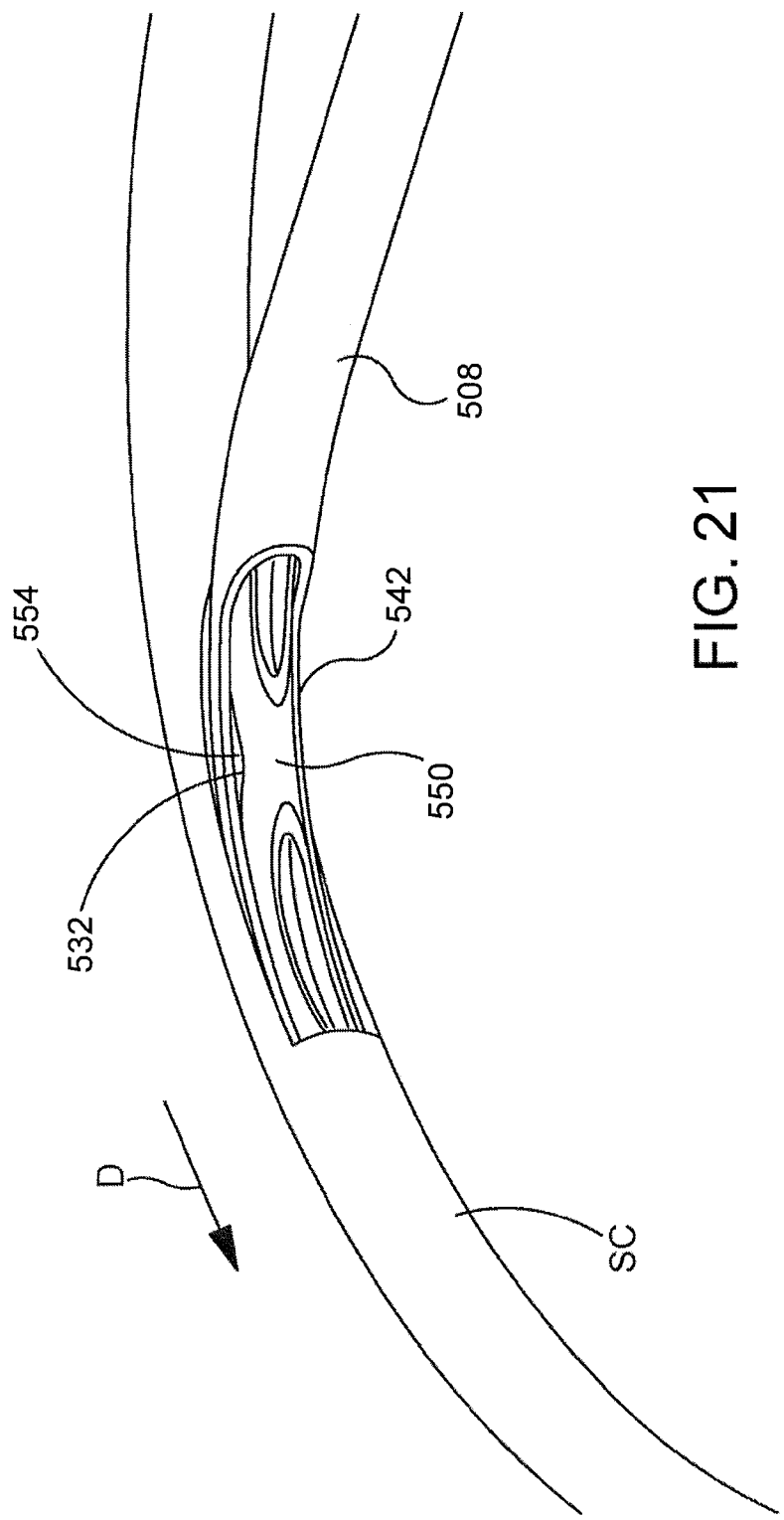
FIG. 21 is an additional perspective view showing the ocular implant and the cannula shown in the previous FIG. 20.

FIG. 21 is an additional perspective view showing ocular implant 550 and cannula 508 shown in the previous figure. By comparing FIG. 21 with the previous figure, it will be appreciated that ocular implant 550 has been advanced in a distal direction D while cannula 508 has remained stationary so that a distal portion of ocular implant 550 is disposed inside Schlemm's canal SC. Trough 554 opens into an elongate opening 532 defined by edge 542 at the distal portion of cannula 508. In the embodiment of FIG. 21, the elongate opening defined by the cannula provides direct visualization of the ocular implant as it is advanced into Schlemm's canal. A configuration allowing direct visualization of the ocular implant has a number of clinical advantages. During a medical procedure, it is often difficult to monitor the progress of the implant by viewing the implant through the trabecular meshwork. For example, blood reflux may push blood into Schlemm's canal obstructing a physician's view the portion of the implant that has entered Schlemm's canal. With reference to FIG. 21, ocular implant 550 tracks along trough 554 as it is advanced distally along cannula 508. The trough opening allows the physician to monitor the progress of the implant by viewing the implant structures as they advance through the trough prior to entering Schlemm's canal. The trough opening also allows the physician to identify the position of the proximal end of the ocular implant with respect to the incision made by the cannula to access Schlemm's canal.

Figure 22:
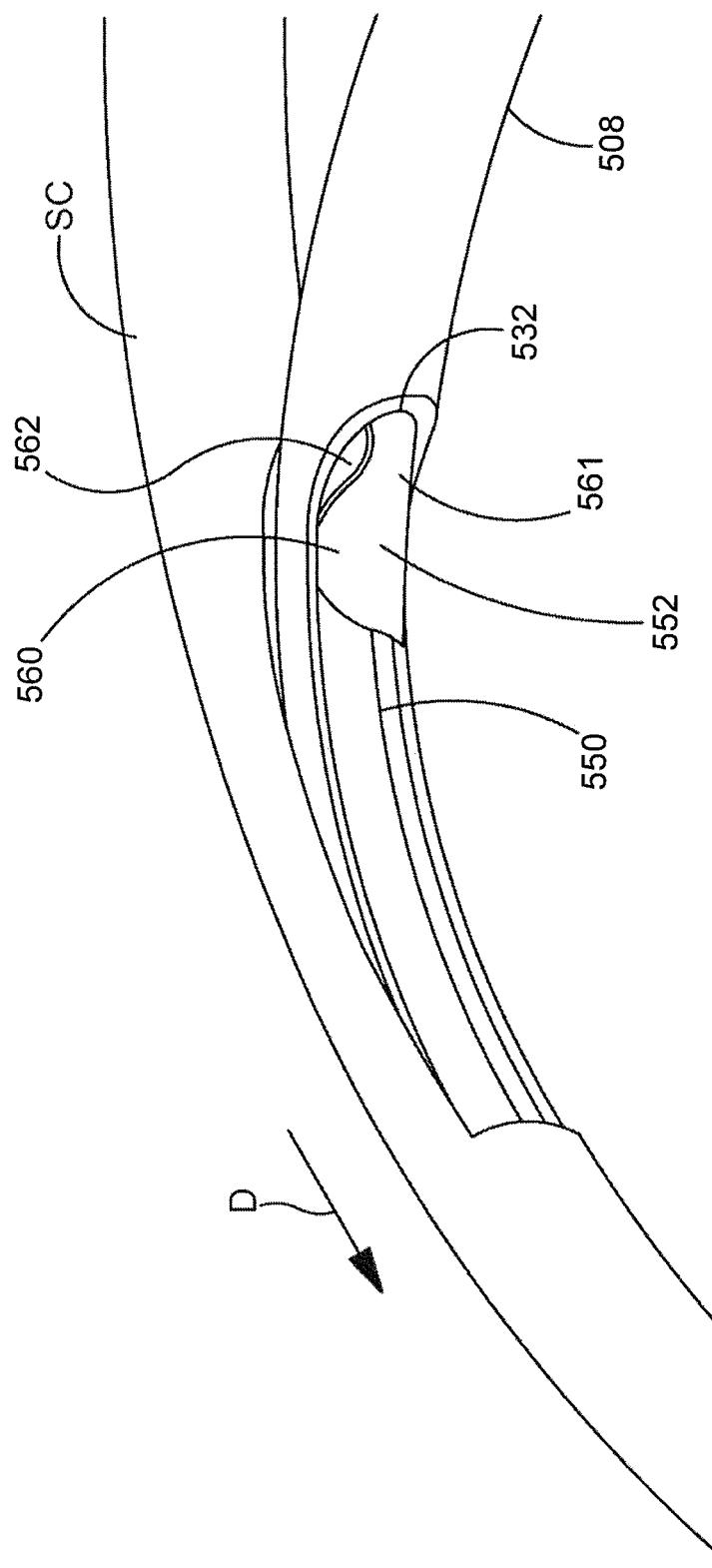
FIG. 22 is an additional perspective view showing the ocular implant and the cannula shown in FIG. 21.

FIG. 22 is an additional stylized perspective view showing ocular implant 550 and cannula 508. In the embodiment of FIG. 22, the interlocking portions 560 and 562 of the delivery tool 552 and ocular implant 550, respectively, can be seen entering the distal opening 532 defined by cannula 508. As shown, ocular implant 550 has been advanced in a distal direction D (relative to the embodiment shown in the previous figure) so that more of ocular implant 550 is disposed inside Schlemm's canal SC. Surface 561 opposite interlocking portion 560 of delivery tool 552 still rests against the inner wall of cannula 508 to keep the delivery tool interlocked with ocular implant 550.

FIG. 23 is an additional stylized perspective view showing ocular implant 550 and cannula 508. As shown in FIG.

23, the ocular implant 550 and delivery tool 552 have advanced further distally so that delivery tool surface 561 and part of the reduced diameter portion 563 have now passed into opening 532, thereby permitting the delivery tool curved portion 553 to move toward its curved at-rest shape so that the delivery tool engagement surface 560 disengages and moves away from its complementary engagement surface 562 on the ocular implant 550.

In some useful embodiments, the delivery tool may be colored to provide visual differentiation from the implant. After the disengaging from the ocular implant, cannula 508 and delivery tool 552 can be withdrawn from Schlemm's canal SC leaving the ocular implant 550 in the fully deployed position shown in FIG. 23. After delivery of ocular implant 550 is complete, the delivery tool and the cannula may be removed from the eye, leaving at least a distal portion of the ocular implant in Schlemm's canal.

Figure 24:
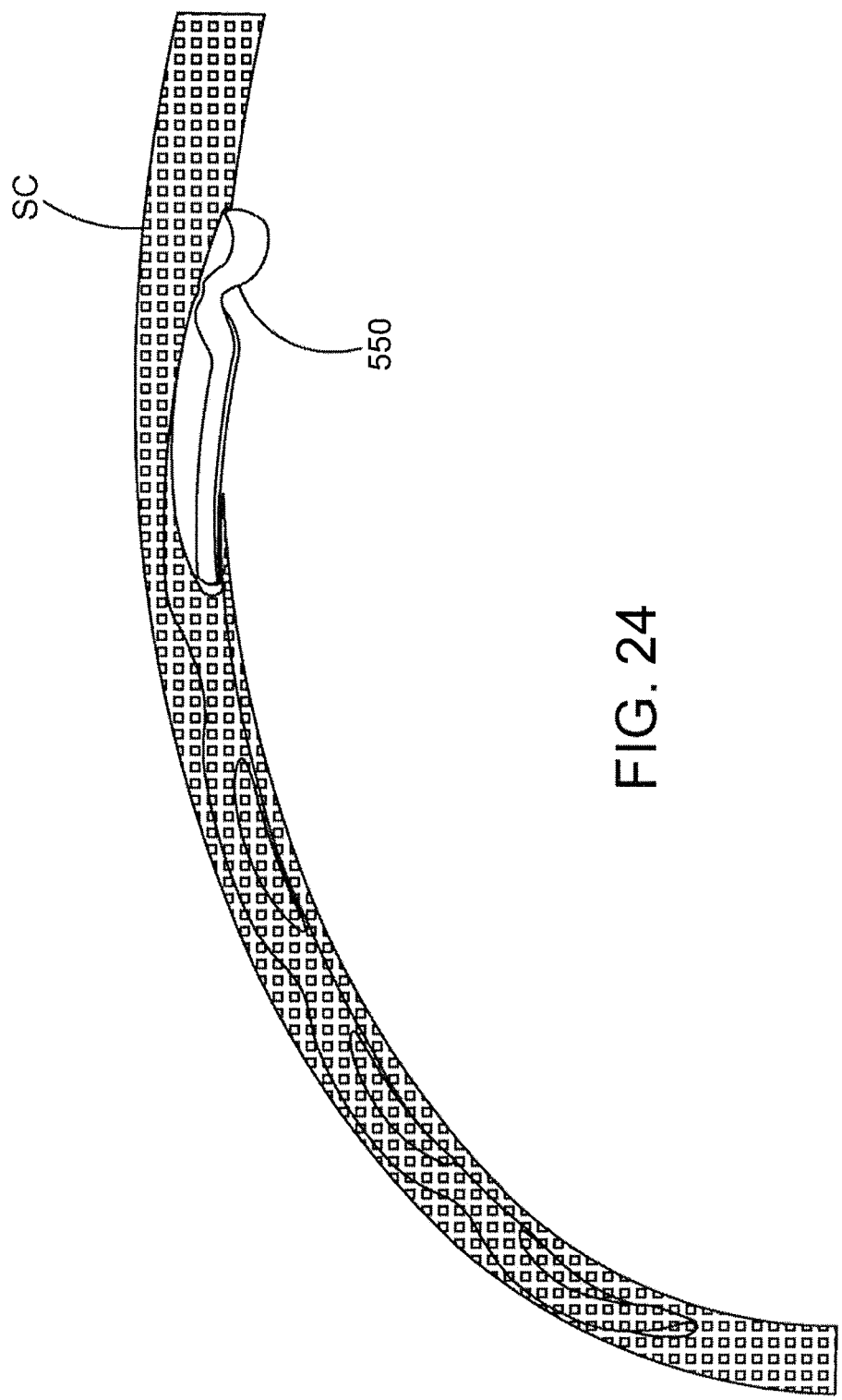
FIG. 24 is a perspective view of Schlemm's canal after the cannula shown in FIG. 23 has been withdrawn leaving an inlet portion of the ocular implant in the anterior chamber of the eye and the remainder of ocular implant in Schlemm's canal.

FIG. 24 is a perspective view of Schlemm's canal SC after the cannula (seen in the previous figure) has been withdrawn leaving an inlet portion of ocular implant 550 in the anterior chamber of the eye and the remainder of ocular implant 550 in Schlemm's canal. The presence of ocular implant 550 in Schlemm's canal may facilitate the flow of aqueous humor out of the anterior chamber. This flow may include axial flow along Schlemm's canal, flow from the anterior chamber into Schlemm's canal, and flow leaving Schlemm's canal via outlets communicating with Schlemm's canal. When in place within the eye, ocular implant 550 will support the trabecular meshwork and Schlemm's canal tissue and will provide for improved communication between the anterior chamber and Schlemm's canal (via the trabecular meshwork) and between pockets or compartments along Schlemm's canal.

In some instances, it may be desirable to deliver an ocular implant to Schlemm's canal in conjunction with another corrective surgery, such as, but not limited to, cataract surgery. When the ocular implant is placed during another surgical procedure, it may be desirable to insert the ocular implant through the same incision used for the other procedure. FIG. 25A is a perspective view showing another illustrative delivery system 600 that may be used to advance ocular implant 650 into a target location in the eye of a patient through an incision location created for another procedure, such as, but not limited to cataract surgery. The delivery system 600 may include an ocular implant 650 and a cannula 608 defining a passageway that is dimensioned to slidingly receive ocular implant 650. It is contemplated that aspects of delivery system 600 may be similar in form and function to delivery system 500. Examples of target locations that may be suitable in some applications include areas in and around Schlemm's canal, the trabecular meshwork, the suprachoroidal space, and the anterior chamber of the eye. FIG. 25B is an enlarged detail view further illustrating ocular implant 650 and cannula 608 of delivery system 600.

Delivery system 600 of FIG. 25A is capable of controlling the advancement and retraction of ocular implant 650 within cannula 608. Ocular implant 650 may be placed in a target location (e.g., Schlemm's canal) by advancing the ocular implant 650 through a distal opening 632 of cannula 608 while the distal opening is in fluid communication with Schlemm's canal. In the embodiment of FIG. 25A, ocular implant 650 has been advanced through distal opening 632 of cannula 608 for purposes of illustration.

Delivery system 600 of FIG. 25A includes a housing 602, a sleeve 604, and an end cap 610. A tracking wheel 606 extends through a wall of housing 602 in FIG. 25A. Tracking wheel 606 is part of a mechanism that is capable of advancing and retracting a delivery tool 652 of delivery system 600. The delivery tool 652 is slidably disposed within cannula 608 and configured to extend through a distal opening of cannula 608. Rotating the tracking wheel will cause delivery tool 652 to move in an axial direction along a passageway defined by cannula 608. The axial direction may be in a distal direction D or a proximal direction P. Delivery tool 652 may be similar in form and function to delivery tool 152.

In the embodiment of FIG. 25A, housing 602 is configured to be gripped with one hand while providing control over the axial advancement and retraction of ocular implant via tracking wheel 606. The features of housing 602 result in an advantageous ergonomic relationship of the fingers relative to the hand. This design provides a configuration that will allow a user, such as a physician, to stabilize the device using part of the hand, while leaving the middle or index finger free move independently from the remainder of the hand. The middle or index finger is free to move independently to rotate the wheel for advancing and/or retract the ocular implant.

Figure 25:
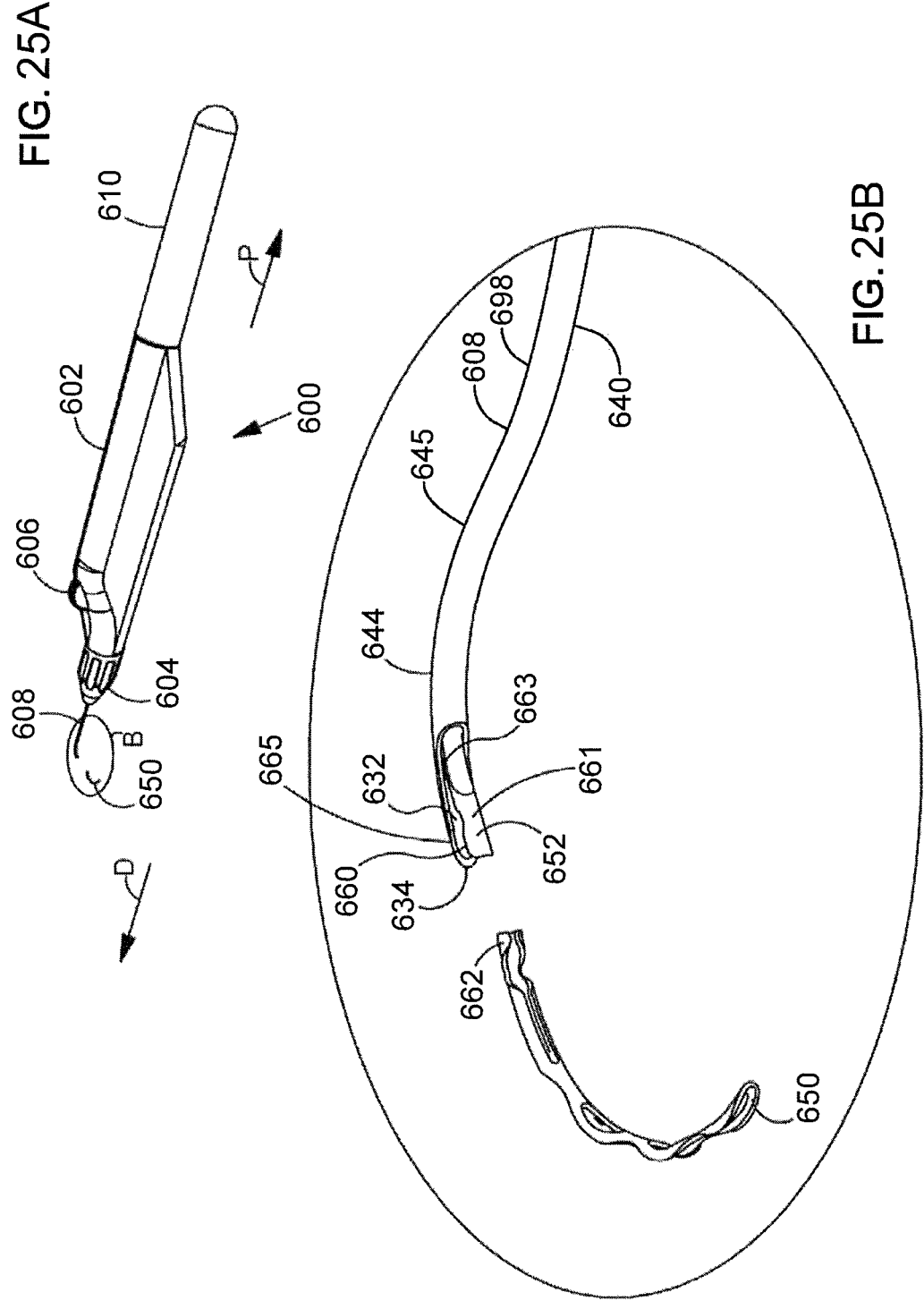
FIG. 25A is a perspective view showing another illustrative delivery system including an ocular implant and a cannula defining a passageway that is dimensioned to slidingly receive the ocular implant.
FIG. 25B is an enlarged detail view further illustrating the ocular implant and the cannula shown in FIG. 25A.

FIG. 25B is an enlarged detail view further illustrating ocular implant 650 and a cannula 608 of delivery system 600. Cannula 608 comprises a generally tubular member 698 having proximal portion 640, an intermediate portion 645, a distal portion 644, and a distal end 634. The intermediate portion 645 may extend distally from a first point 643 distal to the proximal end 641 to a second point 647 proximal to the distal end 634. The distal portion 644 may extend between distally from the second point 647 to distal end 634 of cannula 608 (shown in FIG. 28). In the embodiment of FIG. 25, both distal portion 644 and intermediate portion 645 may be curved. In some instances, distal portion 644 may have a smaller radius of curvature, and thus a higher curvature, than the intermediate portion 645, although this is not required. In some useful embodiments, distal portion 644 and intermediate portion 645 may be dimensioned and configured to be received in the anterior chamber of the eye.

In some instances, it may be desirable to place the ocular implant 650 during another ocular procedure, such as, but not limited to cataract surgery. It is contemplated that the optimal position for an incision for cataract surgery may not be the same as the optimal position of an incision for solely placing an ocular implant, such as implant 650, into Schlemm's canal. With previous ocular implant delivery system designs, in order to allow for substantially tangential entry of the cannula into Schlemm's canal two separate incisions may be required when the implant is placed in combination with another ocular procedure. The curved configuration of both the distal portion 644 may be configured to allow for substantially tangential entry of the cannula 608 into Schlemm's canal. It is further contemplated that the curved configuration of the intermediate portion 645 may allow the cannula 608 to be advanced through typical incisions associated with and/or optimized for cataract surgery, such as, but not limited to, a sclerocorneal tunnel incision, while still allowing for substantially tangential entry of the cannula 608 into Schlemm's canal. This may allow for two or more ocular procedures to be performed using a single incision. It is further contemplated that performing multiple procedures through a single incision may reduce patient discomfort and recovery time. FIG. 25B shows delivery tool 652 of delivery system 600 extending through distal opening 632 of cannula 608. Delivery tool 652 includes an interlocking portion 660 that is configured to form a connection with a complementary interlocking portion 662 of ocular implant 650, as explained in more detail below. In the embodiment of FIG. 25, rotating the tracking wheel will cause delivery tool 652 and ocular implant 650 to move along a path defined by cannula 608. Cannula 608 is sized and configured so that the distal end of cannula 608 can be advanced through the trabecular meshwork of the eye and into Schlemm's canal. Positioning cannula 608 in this way places distal opening 632 in fluid communication with Schlemm's canal. Ocular implant 650 may be placed in Schlemm's canal by advancing the ocular implant through distal opening 632 of cannula 608 while the distal opening is in fluid communication with Schlemm's canal. The distal portion of the cannula 608 may include a cutting portion configured to cut through the trabecular meshwork and the wall of Schlemm's canal, such as by providing distal end 634 with a sharp edge adapted to cut through such tissue.

Figure 26:
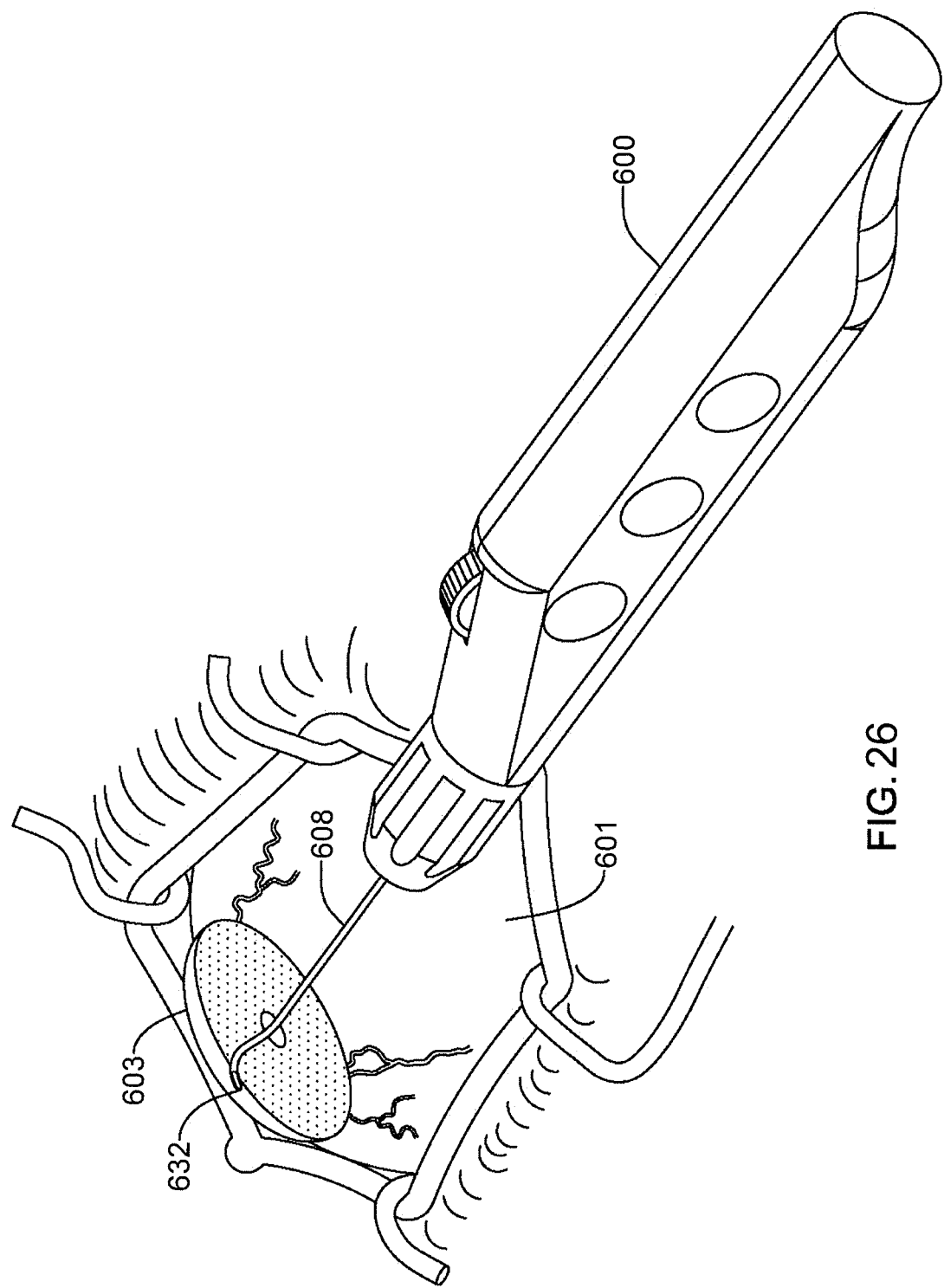
FIG. 26 is an enlarged perspective view further illustrating the delivery system shown in FIG. 25 and an eye.

FIG. 26 is an enlarged perspective view further illustrating delivery system 600 shown in the previous figure and an eye 601. In FIG. 26, cannula 608 of delivery system 600 is shown extending through a cornea 603 of eye 601. A distal portion of cannula 608 is disposed inside the anterior chamber defined by cornea 603 of eye 601. In the embodiment of FIG. 26, cannula 608 is configured so that a distal opening 632 of cannula 608 can be placed in fluid communication with Schlemm's canal. For example, distal portion 644 and intermediate portion 645 of cannula 608 may be dimensioned and configured such that cannula 608 may be advanced through an incision 607 created for another optical surgical procedure.

In the embodiment of FIG. 26, an ocular implant is disposed in a passageway defined by cannula 608. Delivery system 600 includes a mechanism that is capable of advancing and retracting the ocular implant along the length of cannula 608. The ocular implant may be placed in Schlemm's canal of eye 601 by advancing the ocular implant through the distal opening of cannula 608 while the distal opening is in fluid communication with Schlemm's canal.

Figure 27:
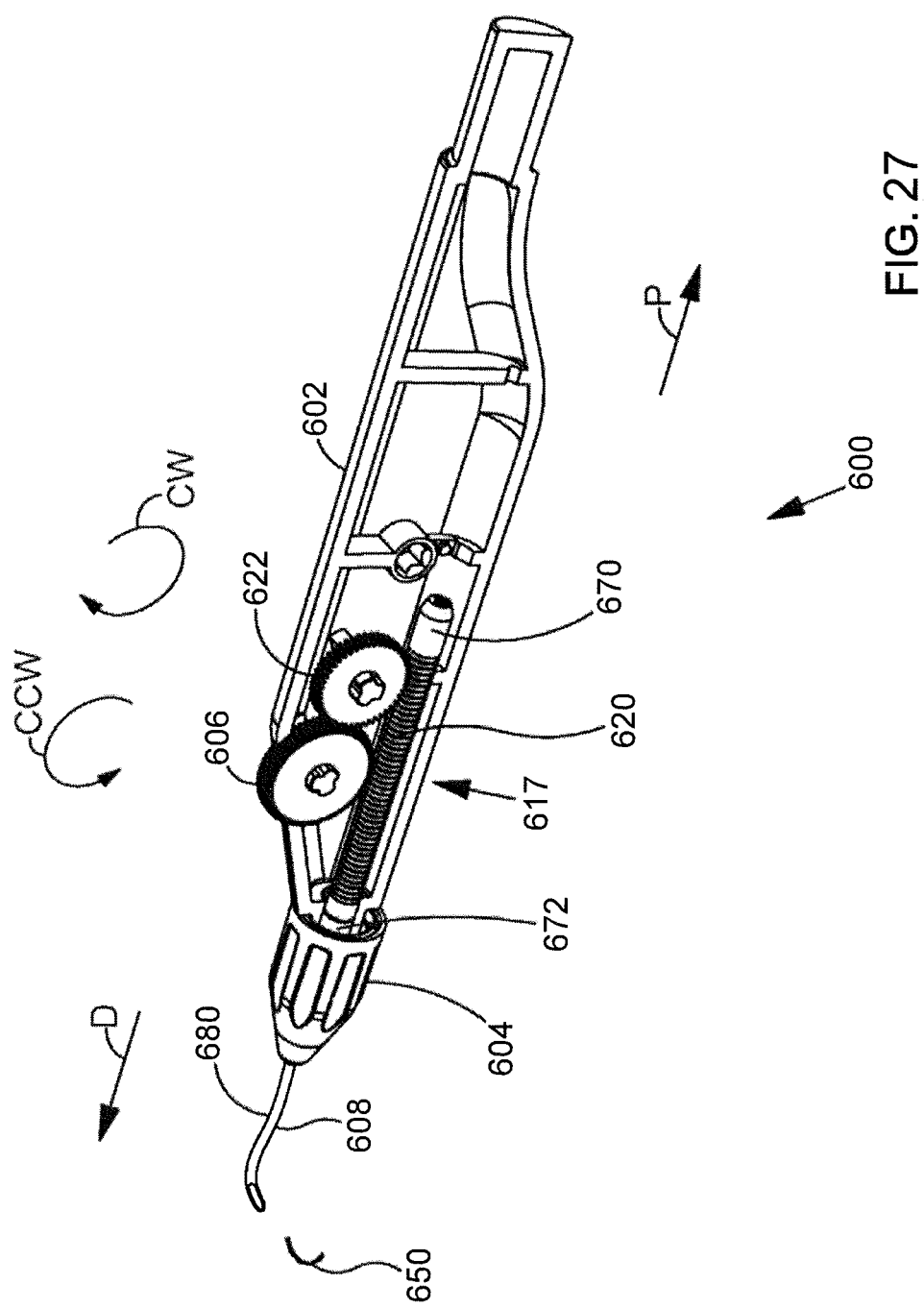
FIG. 27 is a perspective view further illustrating delivery system shown in FIG. 25.

FIG. 27 is a perspective view further illustrating delivery system 600 shown in the previous figure. In FIG. 27, a portion of housing 602 has been removed for purposes of illustration. Delivery system 600 includes a delivery tool subassembly 670 and a cannula subassembly 680. Delivery tool subassembly 670 includes rotating rack gear 620 and a delivery tool (not shown). In the embodiment of FIG. 27, the delivery tool extends into a passageway defined by a cannula 608. Cannula 608 can be seen extending beyond sleeve 604 in FIG. 27. Cannula subassembly 680 includes cannula 608, a hub 672, and an extension tube (not shown). In the embodiment of FIG. 27, the extension tube of cannula subassembly 680 is disposed inside a lumen defined by rotating rack gear 620.

Delivery system 600 includes a mechanism 617 that controls the movement of delivery tool subassembly 670. Mechanism 617 includes a number of components that are located inside housing 602, including tracking wheel 606, an idler gear 622, and the rotating rack gear 620. In the embodiment of FIG. 27, tracking wheel 606 and idler gear 622 are both rotatably supported by housing 602. Gear teeth on tracking wheel 606 engage gear teeth on idler gear 622, which in turn engage gear teeth on the rotating rack gear 620. Rotating tracking wheel 606 in a counter clockwise direction CCW causes idler gear 622 to rotate in a clockwise direction CW, which in turn causes the rotating rack gear 620 to move in a distal direction D. Rotating tracking wheel 606 in a clockwise direction CW causes idler gear 622 to rotate in a counter clockwise direction CCW, which in turn causes the rotating rack gear 620 to move in a proximal direction P. In other embodiments, the idler gear 622 may be eliminated from the device, which would cause counterclockwise movement of the tracking wheel to move the rack gear proximally.

In the embodiment of FIG. 27, a sleeve 604 is fixed to cannula subassembly 680. Sleeve 604 may be rotated by the user to change the orientation of cannula 608 with respect to housing 602. The sleeve 604 may include gripping features, such as grooves (as shown), a rubber coating, or other frictional surfaces to facilitate this use. In some applications, correct alignment between the cannula and iris is advantageous to ensure that the core tube and/or ocular implant is advanced at the correct trajectory relative to Schlemm's canal or other anatomy in the eye into which the ocular implant is to be implanted. The device is configured in a manner that keeps the ocular implant aligned within the device during rotation. Selected groups of components are keyed together to ensure that they rotate as a single body while simultaneously allowing axial movement of the ocular implant. In the embodiment of FIG. 27, cannula subassembly 680 and delivery tool subassembly 670 may rotate in unison with sleeve 604 relative to housing 602.

In the embodiment of FIG. 27, rotating rack gear 620 is configured to rotate with sleeve 604 while maintaining the ability to move axially in the distal and proximal directions before, during, and after rotation. As the rotating rack gear 620 moves distally and/or proximally, it causes corresponding movement of the delivery tool relative to cannula 608. This movement is transferred to ocular implant 650 when delivery tool 652 is coupled to ocular implant 650. Delivery tool subassembly 670 and cannula subassembly 680 engage one another in a keyed arrangement, as described in more detail below. This keyed arrangement causes delivery tool subassembly 670 and cannula subassembly 680 to maintain a constant rotational orientation relative to each other while, at the same time, allowing delivery tool subassembly 670 to translate in a distal direction D and a proximal direction P relative to cannula subassembly 680.

In some embodiments, delivery tool 652 is formed from shape memory material (such as, e.g., nitinol), and at least a portion of delivery tool 652 assumes a curved at-rest shape when no external forces are acting on it. Delivery tool 652 can be urged to assume a straightened shape, for example, by inserting delivery tool 652 through a straight portion of the passageway defined by cannula 608. When the delivery tool 652 is confined, such as within cannula 608, the interlocking portion can engage the complementary interlocking portion to join the delivery tool and ocular implant together, and allow the delivery tool and ocular implant to move together through the cannula 608, as described in more detail below.

Figure 28:
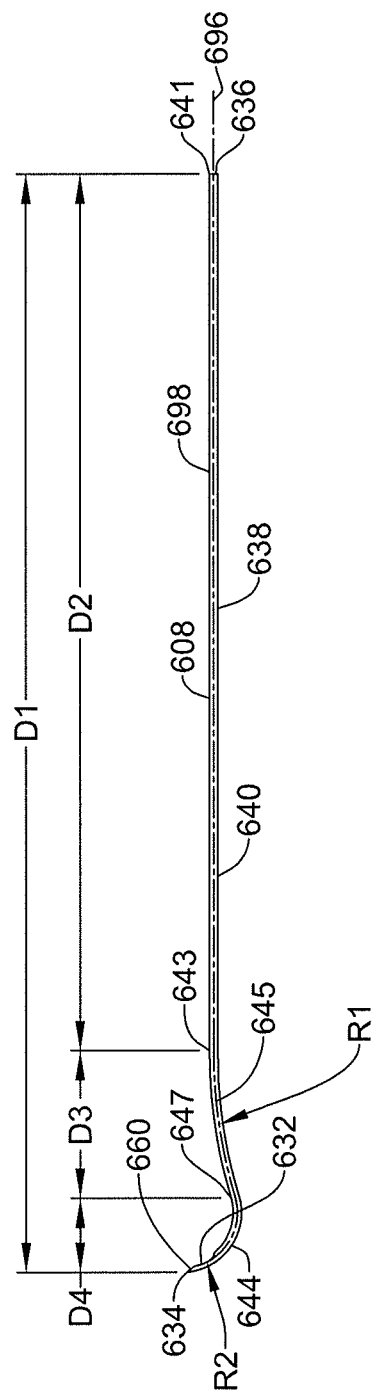
FIG. 28 is a side view further illustrating the cannula shown in FIG. 25.
Figure 29:
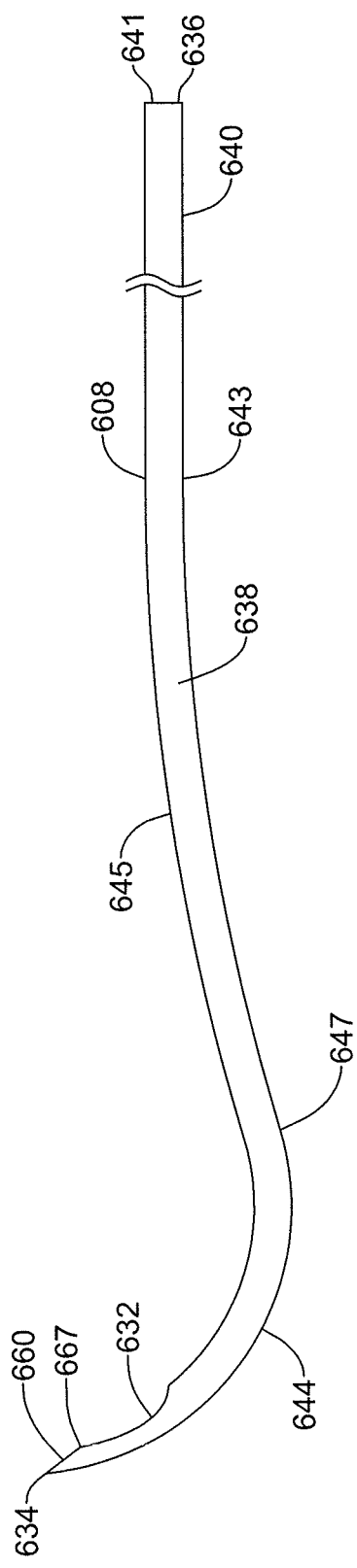
FIG. 29 is an enlarged detail view further illustrating the cannula shown in FIG. 25.
Figure 30:
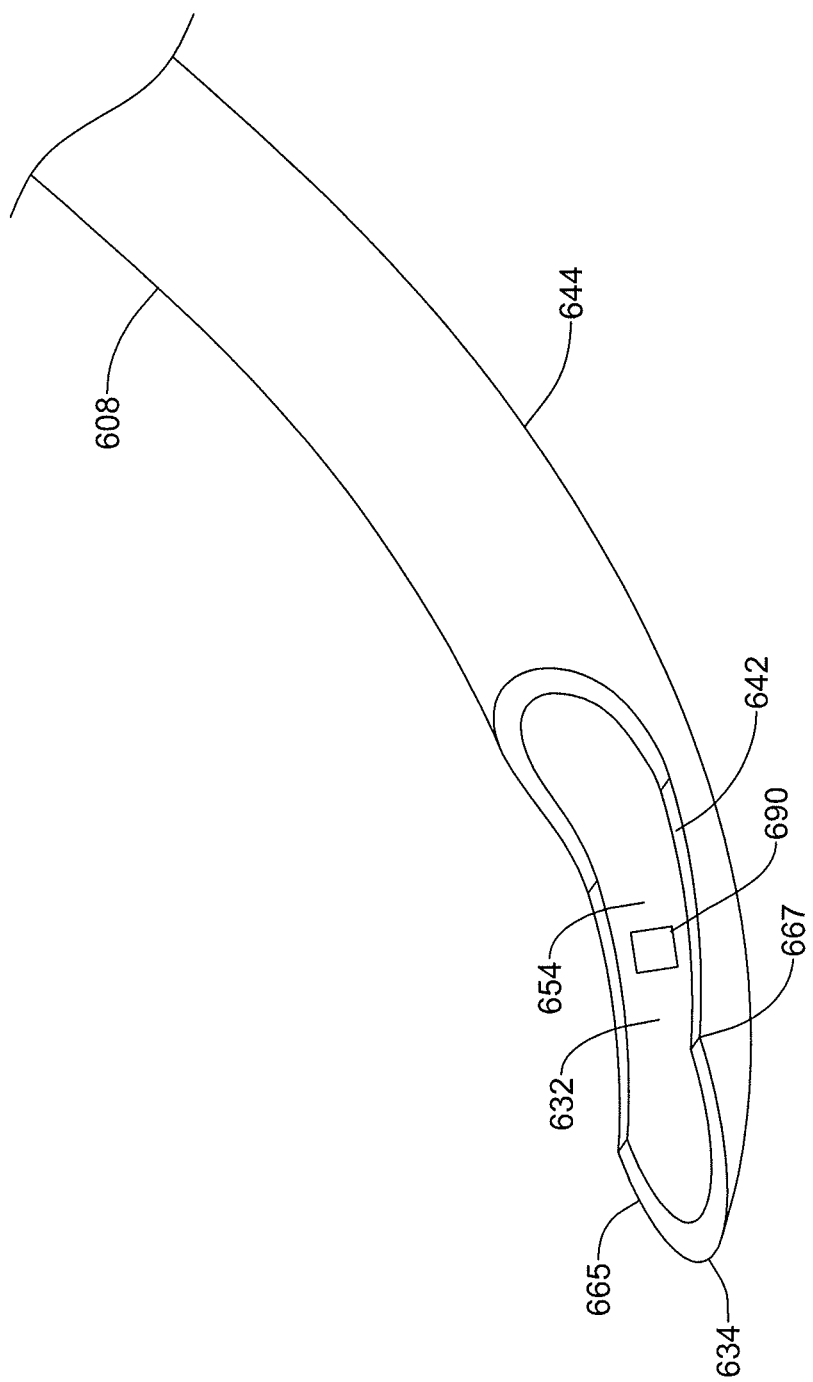
FIG. 30 is an enlarged perspective view further illustrating the distal portion of the cannula shown in FIG. 25.

FIGS. 28, 29, and 30 illustrate more detailed views of cannula 608. FIG. 28 is a side view of a cannula 608 in accordance with the present detailed description, FIG. 29 is an enlarged detail view of cannula 608, and FIG. 30 is an enlarged perspective view further illustrating a portion of distal portion 644 of cannula 608. Cannula 608 comprises a generally tubular member 698 having a central axis 696. Generally, tubular member 698 comprises a proximal end 641, a proximal portion 640, an intermediate portion 645, a distal portion 644, and a distal end 634. Cannula 608 may extend a distance D1 between proximal end 641 and distal end 634. Tubular member 698 may have a length along central axis 696 that is longer than distance D1 between proximal end 641 and distal end 634. For purposes of example, It is contemplated that distance D1 may be in the range of 1.50 to 3.50 inches (3.81 to 8.89 centimeters), 2.0 to 3.0 inches (5.08 to 7.62 centimeters) or around 2.50 inches (6.35 centimeters). It is contemplated cannula 608 may span any distance D1 desired. Proximal portion 640 may extend over a distance D2 from proximal end 641 to a point 643 distal to proximal end 641. Proximal portion 640 may be generally straight such that distance D2 is approximately equal to or equal to a length of proximal portion 640 measured along central axis 696. Distance D2 may be in the range of 1.50 to 2.50 inches (3.81 to 6.35 centimeters), 1.75 to 2.25 inches (4.652 to 5.72 centimeters), or around 2.0 inches (5.08 centimeters). Intermediate portion 645 may extend between first point 643 and a second point 647 located proximal to distal end 634 of cannula 608. Intermediate portion 645 may span a distance D3 extending from point 643 and point 647. Distance D3 may be in the range of 0.15 to 0.50 inches (0.38 to 1.27 centimeters), 0.25 to 0.40 inches (0.64 to 1.02 centimeters), or around 0.33 inches (0.84 centimeters). Intermediate portion 645 may have a length along central axis 696 of tubular member 698 that is longer than distance D3. The difference in the length of intermediate portion 645 and the distance D3 may be determined by the degree of curvature of intermediate portion 645, as will be discussed in more detail below. Distal portion 644 may extend between second point 647 and distal end 634. Distal portion 644 may span a distance D4 extending from point 647 and distal end point 634. Distance D4 may be in the range of 0.05 to 0.30 inches (0.13 to 0.76 centimeters), 0.13 to 0.23 inches (0.33 to 0.58 centimeters), or around 0.17 inches (0.43 centimeters). Distal portion 644 may have a length along central axis 696 of tubular member 698 that is longer than distance D4. The difference in the length of distal portion 644 and the distance D4 may be determined by the degree of curvature of distal portion 644, as will be discussed in more detail below.

A distal opening surface 642 surrounds a distal opening 632 extending through the distal end 634 and through a side wall of cannula 608. A beveled edge 665 is disposed at the distal end of distal opening surface 642, extending from the distal end 634 to a proximal extent 667 of beveled edge 665. Tubular member 698 defines distal opening 632, a proximal opening 636, and a passageway 638 extending between proximal opening 636 and distal opening 632.

Proximal portion 640 of cannula 608 is substantially straight while intermediate portion 645 and distal portion 644 of cannula 608 may be curved. In the embodiment of FIG. 28, distal portion 644 is curved along its entire length and intermediate portion 645 is curved along its entire length. Intermediate portion 645 may define a curve having a first radius R1 measured from central axis 696 and defining a first radius of curvature. The length of intermediate portion 645 along central axis 696 may be determined by the measure of the arc (in degrees) and the radius of the curve using Equation 1 below:

$$L_{arc} = \theta\left(\frac{\pi}{180}\right)r \qquad \text{Equation 1}$$

where $L_{arc}$ is the length of the arc, $\theta$ is the angle measure of the arc (in degrees), and r is the radius of the circle. In some instances, the angle measure of intermediate portion 645 may be in the range of 10° to 25°, although other angles are possible. Distal portion 644 may define a curve having a second radius R2 and defining a second radius of curvature. The length of distal portion 644 along central axis 696 may be determined by the measure of the arc (in degrees) and the radius of the curve using Equation 1 above. In some instances, the angle measure of distal portion 644 may be in the range of 90° to 110°, although other angles are possible. It is contemplated that the first radius R1 may be larger than the second radius R2 such that the distal portion 644 has a higher curvature than the intermediate portion 645. This configuration may advance the ocular implant at the correct trajectory relative to Schlemm's canal or other anatomy in the eye into which the ocular implant is to be implanted. For example, the configuration may allow the cannula 608 to be advanced through an incision generally along a major axis of the visible eye and allowing for substantially tangential entry of cannula 608 into Schlemm's canal. It is contemplated that first radius R1 and second radius R2 may be selected to facilitate delivery of implant 650 to other anatomical locations.

Figure 28A:
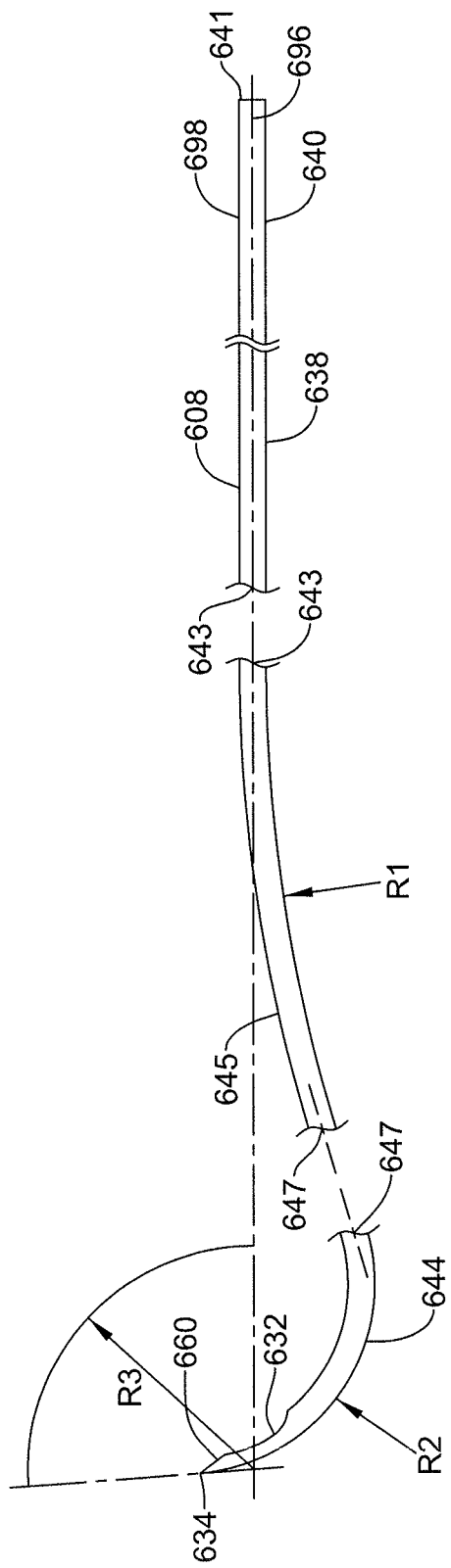
FIG. 28A is an additional side view illustrating the cannula shown in FIG. 25.

FIG. 28A is an additional side view and illustrates a sectioned view of the cannula shown in FIG. 25. For purposes of example, cannula 608 comprises a generally tubular member 698 having a central axis 696. Generally tubular member 698 comprises a proximal end 641, a proximal portion 640, an intermediate portion 645, a distal portion 644, and a distal end 634. Additionally, for example, the central axis 696 of proximal portion 640 is tangential to the tangential line at first point 643 of intermediate portion 645. Further, the tangential line at second point 647 of intermediate portion 645 is tangential to the tangential line of the second point 647 of distal portion 644. The tangential line at distal end 634 of distal portion 644 and the central axis 696 of proximal portion may have third radius R3, for example, having an angle approximately in the range of 90° to 165°.

A method in accordance with this detailed description may include the step of advancing the distal end 634 of cannula 608 through the cornea of a human eye so that distal end 634 is disposed in the anterior chamber of the eye. Cannula 608 may then be used to access Schlemm's canal of the eye, for example, by piercing the wall of Schlemm's canal with the distal end 634 of cannula 608. The beveled edge 665 may be inserted into Schlemm's canal to place at least part of distal opening 632 of cannula 608 in communication with Schlemm's canal. For example, cannula 608 may be advanced until the distal tip 634 and beveled edge 665 of cannula 608 have been inserted into Schlemm's canal up to the proximal extent 667 of beveled edge 665. With the passageway of the cannula 608 placed in fluid communication with the lumen of Schlemm's canal, the ocular implant may be advanced out of a distal port of the cannula 608 and into Schlemm's canal.

In the embodiment of FIG. 29 and further illustrated in FIG. 30, distal portion 644 of cannula 608 defines a trough 654. In some embodiments, trough 654 is configured to receive the entire external cross section of an ocular implant as the ocular implant is being advanced into Schlemm's canal. When this is the case, trough 654 may have a depth dimension that is deeper than a width of the ocular implant. This cannula configuration advantageously prevents the ocular implant from intersecting the layers of the trabecular meshwork as the ocular implant is advanced into Schlemm's canal. Trough 654 may also be configured to allow the proximal portion of the ocular implant to be released from the delivery tool in a manner similar to trough 554 described above.

Referring briefly to FIG. 25B, while not explicitly shown, during advancement of ocular implant 650 interlocking portion 660 of delivery tool 652 and complementary interlocking portion 662 of ocular implant 650 may be engaged with each other so that a proximal end of ocular implant 650 is proximal to the distal end of delivery tool 652. Surface 661 of delivery tool 652 rests against the wall of cannula 608 to prevent interlocking portion 660 of delivery tool 652 and complementary interlocking portion 662 of ocular implant 650 from disengaging one another. When they are connected in this fashion, delivery tool 652 and ocular implant 650 move together as the delivery tool is advanced and retracted relative to cannula 608 by the delivery system mechanism. In some embodiments, the ocular implant 650 has a radius of curvature that is larger than the radius of curvature of the distal portion 644 of cannula 608. This arrangement ensures that the ocular implant will track along trough 654 as the ocular implant is urged in a distal direction by delivery system 600.

Once cannula 608 has been positioned in the desired location, ocular implant 650 may be advanced distally while cannula 608 is held stationary. Elongate opening 632 may provide direct visualization of ocular implant 650 as it is advanced into Schlemm's canal. A configuration allowing direct visualization of the ocular implant has a number of clinical advantages. During a medical procedure, it is often difficult to monitor the progress of the implant by viewing the implant through the trabecular meshwork. For example, blood reflux may push blood into Schlemm's canal obstructing a physician's view the portion of the implant that has entered Schlemm's canal. Ocular implant 650 tracks along trough 654 as it is advanced distally along cannula 608. The trough opening allows the physician to monitor the progress of the implant by viewing the implant structures as they advance through the trough prior to entering Schlemm's canal. The trough opening also allows the physician to identify the position of the proximal end of the ocular implant with respect to the incision made by the cannula to access Schlemm's canal.

Delivery tool 652 may advance ocular implant 650 distally until delivery tool surface 661 and part of the reduced diameter portion 663 have now passed into opening 632, thereby permitting the delivery tool curved portion to move toward its curved at-rest shape so that the delivery tool engagement surface 660 disengages and moves away from its complementary engagement surface 662 on the ocular implant 650. After the disengaging from the ocular implant, cannula 608 and delivery tool 652 can be withdrawn from Schlemm's canal leaving the ocular implant 650 in the fully deployed position. After delivery of ocular implant 650 is complete, the delivery tool 652 and the cannula 608 may be removed from the eye, leaving at least a distal portion of the ocular implant 650 in Schlemm's canal. An inlet portion of ocular implant 650 may be positioned in the anterior chamber of the eye and the remainder of ocular implant 650 in Schlemm's canal. The presence of ocular implant 650 in Schlemm's canal may facilitate the flow of aqueous humor out of the anterior chamber. This flow may include axial flow along Schlemm's canal, flow from the anterior chamber into Schlemm's canal, and flow leaving Schlemm's canal via outlets communicating with Schlemm's canal. When in place within the eye, ocular implant 650 will support the trabecular meshwork and Schlemm's canal tissue and will provide for improved communication between the anterior chamber and Schlemm's canal (via the trabecular meshwork) and between pockets or compartments along Schlemm's canal.

The cannula 608 may further include a pressure sensor 690 disposed within the trough 654. The pressure sensor 690 may be similar in form and function to pressure sensor 180 described above. While the pressure sensor 690 is illustrated as mounted within the trough 654 of the cannula, it is contemplated that the pressure sensor 690 may be mounted at other locations within or on the cannula 608. The pressure sensor 690 may provide an instantaneous pressure reading during implantation of the ocular implant 650 or shortly thereafter. In some instances, the pressure reading obtained from the pressure sensor 690 on the cannula 608 can be compared to a pressure reading obtained from a pressure sensor mounted on the ocular implant 650, if so provided.

The pressure sensor 690 may be a Micro-Electro-Mechanical System (MEMS) pressure sensor. While the pressure sensor 690 has been described as a MEMS pressure sensor, it is contemplated that other pressure sensors may be used in place of, or in addition to, a MEMS pressure sensor. Further, while only a single pressure sensor 690 has been illustrated, the cannula 608 may include more than one pressure sensor 690, as desired. MEMS pressure sensors are often formed by anisotropically etching a recess into a back side of a silicon substrate die, leaving a thin flexible diaphragm. In operation, at least one surface of the diaphragm is exposed to an input pressure (e.g., the ocular pressure). The diaphragm deflects according to the magnitude of the input pressure, which may be detected by one or more electrical components or sense elements (e.g., piezoresistors) positioned on or embedded within the diaphragm. The change in resistance of the piezoresistors is reflected as a change in an output voltage signal from a resistive bridge formed at least in part by the piezoresistors. In some cases, the diaphragm may be made thinner with the addition of support bosses, which may help increase the sensitivity of the diaphragm over a flat plate diaphragm. Circuit elements may be connected so that sensor elements to provide some level of signal processing before providing an output signal to bond pads of the pressure sensor. The signal processing may filter, amplify, linearize, calibrate and/or otherwise process the raw sensor signal produced by the sensor elements (e.g., piezoresistors). While the sense elements have been described as piezoresistors, it is contemplated that the sense elements may be selected to provide a capacitive pressure sensor 690.

The pressure sensor 690 may be further provided with an antenna or inductor to allow the data from the pressure sensor 690 to be wirelessly communicated to a readout device. In some instances, the pressure sensor 690 may use radiofrequency communication protocols, such as, but not limited to cellular communication, ZigBee®, Bluetooth®, WiFi®, IrDA, dedicated short range communication (DSRC), EnOcean®, or any other suitable wireless protocols, as desired to transmit the data from the pressure sensor 690 to another device located outside the body. The data may be transmitted to any number so suitably enabled devices, including, but not limited to, cellular phones, tablet computers, computers, portable handheld devices, such a personal digital assistant (PDA), or a specially designed device. This may allow a physician, patient, or other interested party to monitor the ocular pressure without the use of a tonometer.

Components of ocular device may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, utylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

It is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed is:
1. An ocular implant adapted to reside at least partially in a portion of Schlemm's canal of an eye, the implant comprising:
    a tubular body having an inner surface defining an elongate channel and an outer surface, the tubular body extending in a curved volume whose longitudinal axis forms an arc of a circle; and a plurality of openings adapted to allow aqueous humor to flow within the elongate channel of the tubular body;

a plurality of strut areas formed in the tubular body, each of the strut areas comprising an edge defining one of the plurality of openings;

a pressure sensor disposed on the inner surface of the tubular body adjacent an opening of the plurality of openings, the pressure sensor comprising a diaphragm facing the elongate channel and a piezoresistor disposed on the diaphragm; and the tubular body having a diameter of between 0.005 inches and 0.04 inches.

2. The implant of claim 1, wherein the pressure sensor further comprises a first substrate comprising a layered silicon substrate and a cavity, the diaphragm being disposed over the cavity, and a second substrate comprising a semiconductor wafer.

3. The implant of claim 1, wherein the pressure sensor includes an antenna for transmitting data from the pressure sensor to a remote location.

4. The implant of claim 3, wherein the data is automatically transmitted from the remote location to a second remote device.

5. The implant of claim 1, wherein the strut areas are connected by one or more spine areas.

6. The implant of claim 1, wherein each strut area undulates in a circumferential direction as it extends longitudinally between a first spine area and a second spine area.

7. The implant of claim 1, wherein the implant is formed from shape memory material in a shape approximately equal to the curved volume.

* * * * *